US010106584B2

(12) United States Patent
Chuong et al.

(10) Patent No.: US 10,106,584 B2
(45) **Date of Patent: *Oct. 23, 2018**

(54) RED-SHIFTED OPSIN MOLECULES AND USES THEREOF

(71) Applicant: Massachusetts Institute of Technology, Cambridge, MA (US)

(72) Inventors: Amy Chuong, Ashburn, VA (US); Nathan Klapoetke, Ashburn, VA (US); Brian Yichiun Chow, Cherry Hill, NJ (US); Edward Boyden, Chestnut Hill, MA (US); Xue Han, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/282,251

(22) Filed: Sep. 30, 2016

(65) Prior Publication Data

US 2017/0044219 A1 Feb. 16, 2017

Related U.S. Application Data

(63) Continuation of application No. 14/600,635, filed on Jan. 20, 2015, now Pat. No. 9,500,641, which is a (Continued)

(51) Int. Cl.

*A61K 38/16* (2006.01)
*C07K 14/215* (2006.01)

(Continued)

(52) U.S. Cl.

CPC .......... *C07K 14/215* (2013.01); *A61K 38/164* (2013.01); *A61K 41/0057* (2013.01);

(Continued)

(58) Field of Classification Search

CPC ...... A61K 38/164; C07K 14/215; C12N 5/16; G01N 33/5032; Y10S 530/825

See application file for complete search history.

(56) References Cited

U.S. PATENT DOCUMENTS

| | | |
|---|---|---|
| 5,041,224 A | 8/1991 | Ohyama et al. |
| 6,197,387 B1 | 3/2001 | Fiedler et al. |

(Continued)

FOREIGN PATENT DOCUMENTS

| | | |
|---|---|---|
| WO | 2010056970 A3 | 5/2010 |

OTHER PUBLICATIONS

Baliga, N.S. et al., "Genome sequence of Haloarcula marismortui: A halophilic archaeon from the Dead Sea", Genome Research, 2004, vol. 14, pp. 2221-2234.

(Continued)

*Primary Examiner* — Jeffrey E. Russel

(74) *Attorney, Agent, or Firm* — Pierce Atwood LLP

(57) ABSTRACT

Compositions and methods for altering cell activity and function by expressing a light-activated ion pump polypeptide in a cell and contacting the cell with light that activates the expressed light-activated ion pump polypeptide. In some aspects of the invention, a light-activated ion pump polypeptide is a modified *haloarcula* halorhodopsin polypeptide, for example, a modified Halo 57 polypeptide.

25 Claims, 8 Drawing Sheets

Specification includes a Sequence Listing.

Photocurrent (pA)

0 100 200 300 400 500 600

Halo57

Halo57 Double Mutant

Related U.S. Application Data continuation of application No. 13/295,750, filed on Nov. 14, 2011, now Pat. No. 8,957,028.

(60) Provisional application No. 61/413,431, filed on Nov. 13, 2010.

(51) Int. Cl.

| | |
|---|---|
| ***C12N 5/071*** | (2010.01) |
| ***G01N 33/68*** | (2006.01) |
| ***G01N 33/50*** | (2006.01) |
| ***A61K 41/00*** | (2006.01) |
| *C12N 5/0793* | (2010.01) |
| *C12N 5/16* | (2006.01) |

(52) U.S. Cl.

CPC ....... *G01N 33/5032* (2013.01); *C12N 5/0619* (2013.01); *C12N 5/16* (2013.01); *Y10S 530/825* (2013.01)

(56) References Cited

U.S. PATENT DOCUMENTS

| | | | | |
|---|---|---|---|---|
| 8,401,609 | B2 | 3/2013 | Deisseroth et al. | |
| 8,957,028 | B2 | 2/2015 | Chuong | |
| 9,500,641 | B2 * | 11/2016 | Chuong | C07K 14/215 |
| 2009/0191599 | A1 | 7/2009 | Devroe | |
| 2010/0145418 | A1 | 6/2010 | Zhang et al. | |
| 2010/0234273 | A1 | 9/2010 | Boyden et al. | |
| 2011/0165681 | A1 | 7/2011 | Boyden et al. | |
| 2012/0121542 | A1 | 5/2012 | Chuong et al. | |

OTHER PUBLICATIONS

Boyden, E. et al., “Millisecond-timescale, genetically targeted optical control of neural activity”, Nature Neuroscience, Sep. 2005, vol. 8, pp. 1263-1268.

Busskamp, V. et al., “Genetic Reactivation of Cone Photoreceptors Restores Visual Responses in Retinitis Pigmentosa”, Science., Jul. 23, 2010, vol. 329, pp. 413-417, No. 5990, Epub.

Chow, B.Y. et al., “High-performance genetically targetable optical neural silencing by light-driven proton pumps”, Nature, Jan. 7, 2010, vol. 463, pp. 98-102, and Supplemental Information, “Supplementary Figures and Legends”, www.nature.com/nature, 2010, pp. 1-25.

Chow, B.Y. et al., “Synthetic Physiology Strategies for Adapting Tools from Nature for Genetically Targeted Control of Fast Biological Processes”, Methods Enzymol., 2011, vol. 497, pp. 425-443.

Chuong, A.S. et al., “Development of next-generation optical neural silencers through directed combinatorial optimization”, Society for Neuroscience, Annual Meeting 2010 Abstract, Program #106.2/MMM9.

Chuong, A.S., et al., “Red-Shifted Optical Neuronal Silencing: Optical Hemoglobin Transparency for Long Distance Optogenetic Inhibition”, Society for Neuroscience Annual Meeting, 2010, Nov. 13, 2010. Poster Presentation.

Gradinaru, V. et al., “eNpHR: a Natronomonas halorhodopsin enhanced for optogenetic applications”, Brain Cell Biology, Aug. 2008, vol. 36, pp. 129-139.

Gradinaru, V. et al., “Molecular and Cellular Approaches for Diversifying and Extending Optogenetics”, Cell, Apr. 2, 2010, vol. 141, pp. 154-165.

Hackett, N.R. et al., “Structure-Function Studies on Bacteriorhodopsin”, The Journal of Biological Chemistry, Jul. 5, 1987, vol. 262, No. 19, pp. 9277-9284.

Han, X. and Boyden, E.S., “Multiple-Color Optical Activation, Silencing, and Desynchronization of Neural Activity, with Single-Spike Temporal Resolution” PloS one, Mar. 2007, Issue 3, pp. 1-12.

Han, X. et al., “A high-light sensitivity optical neural silencer: development and application to optogenetic control of non-human primate cortex”, Frontiers in Systems Neuroscience, Apr. 13, 2011, vol. 5, Article 18, pp. 1-8.

Han et al., “Informational lesions: optical perturbation of spike timing and neural synchrony via microbial opsin gene fusions”, Frontiers in Molecular Neuroscience, Aug. 27, 2009, vol. 2, Article 12, pp. 1-9, Epub.

Ihara, K. et al., “*Haloarcula argentinensis* sp. nov. and *Haloarcula mukohataei* sp. nov., Two New Extremely Halophilic Archaea Collected in Argentina”, International Journal of Systematic Bacteriology, Jan. 1997, vol. 47, No. 1, pp. 73-77.

Ihara, K. et al., “Evolution of the Archaeal Rhodopsins: Evolution Rate Changes by Gene Duplication and Functional Differentiation”, J. Mol. Biol., 1999,vol. 285, Article No. jmbi.1998.2286 available online at http://www.idealibrary.com, pp. 163-174.

Javor, Barbara et al., “Box-Shaped Halophilic Bacteria”, Journal of Bacteriology, Sep. 1982, vol. 151, No. 3, pp. 1532-1542.

Klare, J.P. et al., “Microbial Rhodopsins: Scaffolds for Ion Pumps, Channels, and Sensors”, Results Probl Cell Differ, Sep. 27, 2007, vol. 45, pp. 73-122.

Kitajima, T. et al., “Novel Bacterial Rhodopsins from Haloarcula vallismortis”, Biochemical and Biophysical Research Communications,1996, vol. 220, Article No. 0407, pp. 341-345.

Mogi, T. et al., “Structure-Function Studies on Bacteriorhodopsin”, The Journal of Biological Chemistry, Aug. 25, 1989, vol. 264, No. 24, pp. 14197-14201.

Mukohata et al. Halobacterial Rhodopsins. Journal of Biochemistry. 1999. vol. 125, No. 4, pp. 649-657.

Otomo, Jun, “Anion selectivity and pumping mechanism of halorhodopsin”, Biophysical Chemistry, 1995, vol. 56, pp. 137-141.

Otomo, Jun et al., “Bacterial rhodopsins of newly isolated halobacteria”, Journal of General Microbiology, 1992, vol. 138, pp. 1027-1037.

Otomo, J. and Muramatsu, T., “Over-expression of a new photo-active halorhodopsin in Halobacterium salinarium”, Biochimica et Biophysica Acta, 1995, vol. 1240, pp. 248-256.

Rudiger, M. and Oesterhelt, D., “Specific arginine and threonine residues control anion binding and transport in the light-driven chloride pumo halorhodopsin”, The EMBO Journal, 1997, vol. 16, No. 13, pp. 3813-3821.

Tang et al., “Faithful Expression of Multiple Proteins via 2A-Peptide Self-Processing: A Versatile and Reliable Method for Manipulating Brain Circuits”, The Journal of Neuroscience, Jul. 8, 2009, vol. 29, No. 27, pp. 8621-8629.

Zhang, F. et al., “Multimodal fast optical interrogation of neural circuitry” Nature, Apr. 2007, vol. 446, pp. 633-639.

Non-Final Rejection received in U.S. Appl. No. 13/295,750 (dated Aug. 19, 2013) (11 pages).

Non-Final Rejection received in U.S. Appl. No. 13/295,750 (dated Apr. 10, 2014) (12 pages).

Final Rejection received in U.S. Appl. No. 13/295,750 (dated Jan. 29, 2014) (9 pages).

Final Rejection received in U.S. Appl. No. 13/295,750 (dated Aug. 1, 2014) (10 pages).

Non-Final Rejection received in U.S. Appl. No. 14/600,635 (dated Oct. 30, 2015) (10 pages).

Final Rejection received in U.S. Appl. No. 14/600,635 (dated Feb. 16, 2016) (9 pages).

U.S. Appl. No. 13/295,750, filed Nov. 14, 2011, now U.S. Pat. No. 8,957,028 dated Feb. 17, 2015.

U.S. Appl. No. 14/600,635, filed Jan. 20, 2015, now U.S. Pat. No. 9,500,641 dated Nov. 22, 2016.

* cited by examiner

```
Halo57      MTAVSTTATTVLQATQSDVLQ-----EIQSNFLLNSSIWVNIALAGVVILLFVAMGRDLE 55
Gene4       MTAASTTATTVLQATQSDVLQ-----EIQSNFLLNSSIWVNIALAGVVILLFVAMGRDLE 55
Gene58      MTAASTTATTMLQATQSDVLQ-----EIQSNFLLNSSIWVNIALAGVVILLFVAMGRDIE 55
Gene56      ------------------MLQ-----EIQSNFLLNSSIWVNIALAGVVILLFVAMGRDLE 37
Gene55      ---------------------------------------MNIALAGVVILLFVAMGRDLE 21
Gene54      MSAT----TTLLQATQSEAVT-----AIENDVLLSSSLWANVALAGLAILLFVYMGRNVE 51
Halo        MTETLFPVTESAVALQAEVTQRELFEFVLNDPLLASSLYINIALAGLSILLFVFMTRGLD 60
                                                   *:*****: ***** * *.::

Halo57      SPRAKLIWVATMLVPLVSISSYAGLASGLTVGFLQMPPGHALAG----------QEVLSP 105
Gene4       SPRAKLIWVATMLVPLVSISSYAGLASGLTVGFLQMPPGHALAG----------QEVLSP 105
Gene58      SPRAKLIWVATMLVPLVSISSYAGLASGLTVGFLQMPPGHALAG----------QEVLSP 105
Gene56      SPRAKLIWVATMLVPLVSISSYAGLASGLTVGFLQMPPGHALAG----------QEVLSP 87
Gene55      SPRAKLIWVATMLVPLVSISSYAGLASGLTVGFLQMPPGHALAG----------QEVLSP 71
Gene54      APRAKLIWGATLMIPLVSISSYLGLLSGLTVGFIEMPAGHALAG----------SEVMSQ 101
Halo        DPRAKLIAVSTILVPVVSIASYTGLASGLTISVLEMPAGHFAEGSSVMLGGEEVDGVVTM 120
             *****  :*::*:***:** ** ****:..::**.**    *          : *::

Halo57      WGRYLTWTFSTPMILLALGLLADTDIASLFTAITMDIGMCVTGLAAALITSSHLLRWVFY 165
Gene4       WGRYLTWTFSTPMILLALGLLADTDIASLFTAITMDIGMCVTGLAAALITSSHLLRWVFY 165
Gene58      WGRYLTWTFSTPMILLALGLLADTDIASLFTAITMDIGMCVTGLAAALITSSHLLRWVFY 165
Gene56      WGRYLTWTFSTPMILLALGLLADTDIASLFTAITMDIGMCVTGLAAALITSSHLLRWVFY 147
Gene55      WGRYLTWTFSTPMILLALGLLADTDIASLFTAITMDIGMCVTGLAAALITSSHLLRWVFY 131
Gene54      WGRYLTWALSTPMILLALGLLADVDIGDLFVVIAADIGMCVTGLAAALITSSYGLRWAFY 161
Halo        WGRYLTWALSTPMILLALGLLAGSNATKLFTAITFDIAMCVTGLAAALTTSSHLMRWFWY 180
            *******::*************. :  .**..*: **.********** ***: :** :*

Halo57      GISCAFFVAVLYVLLVQWPADAEAAGTSEIFGTLKILTVVLWLGYPILWALGSEGVALLS 225
Gene4       GISCAFFVAVLYVLLVQWPADAEAAGTSEIFGTLKILTVVLWLGYPILWALGSEGVALLS 225
Gene58      GISCAFFVAVLYVLLVQWPADAEAAGTSEIFGTLKILTVVLWLGYPILWALGSEGVALLS 225
Gene56      GISCAFFVAVLYVLLVQWPADAEAAGTSEIFGTLKILTVVLWLGYPILWALGSDGVALLS 207
Gene55      GISCAFFVAVLYVLLVQWPADAEAAGTSEIFGTLKILTVVLWLGYPILWALGSEGVALLS 191
Gene54      LVSCAFFLVVLYAILVEWPQSATAAGTDEIFGTLKALTVVLWLGYPIIWAVGIEGLALVQ 221
Halo        AISCACFLVVLYILLVEWAQDAKAAGTADMFNTLKLLTVVMWLGYPIVWALGVEGIAVLP 240
             :*** *:.*** :**:*. .* **** ::*.**: ****:******:**:* **:*::

Halo57      -VGVTSWGYSGLDILAKYVFAFLLLRWVAANEGTVSGSGMGIGSGGAAPADD- 276
Gene4       -VGVTSWGYSGLDILAKYVFAFLLLRWVAANEGTVSGSGMGIGSGGATPADD- 276
Gene58      -VGVTSWGYSGLDILAKYVFAFLLLRWVAANEGAVSGSGMSIGSGGAAPADD- 276
Gene56      -VGVTSWGYSGLDILAKYVFAFLLLRWVATNEGTVSGSGMGIGSGGAAPADD- 258
Gene55      -VGVTSWGYSGLDILAKYVFAFLLLRWVATNEGTVSGSGMGIGSGGAAPADD- 242
Gene54      SVGLTSWGYSALDIGAKYLFAFLLLRWVAANQDVVGQPSLDTHSEGTAPADD- 273
Halo        -VGVTSWGYSFLDIVAKYIFAFLLLNYLTSNESVVSGSILDVPSASGTPADD- 291
             **:****** *** ***:******.::::*:..*. . :.  * . :****
```

Figure 3

RED-SHIFTED OPSIN MOLECULES AND USES THEREOF

RELATED APPLICATIONS

This application is a continuation of U.S. application Ser. No. 14/600,635, filed Jan. 20, 2015, which is a continuation of U.S. application Ser. No. 13/295,750, filed Nov. 14, 2011, now issued as U.S. Pat. No. 8,957,028, which claims the benefit under 35 U.S.C. § 119(e) of U.S. Provisional application Ser. No. 61/413,431 filed Nov. 13, 2010, the disclosure of each of which is incorporated by reference herein in its entirety.

GOVERNMENT INTEREST

This invention was made with government support under Grant Nos. R01 DA029639, R01 NS067199 and RC1 MH088182 awarded by the National Institutes of Health. The government has certain rights in the invention.

FIELD OF THE INVENTION

The invention, in some aspects relates to compositions and methods for altering cell activity and function and the use of light-activated ion pumps.

BACKGROUND OF THE INVENTION

Altering and controlling cell membrane and subcellular region ion permeability has permitted examination of characteristics of cells, tissues, and organisms. Light-driven pumps and channels have been used to silence or enhance cell activity and their use has been proposed for drug screening, therapeutic applications, and for exploring cellular and subcellular function.

Molecular-genetic methods for preparing cells that can be activated (e.g., depolarized) or inactivated (e.g., hyperpolarized) by specific wavelengths of light have been developed (see, for example, Han, X. and E. S. Boyden, 2007, PLoS ONE 2, e299). It has been identified that the light-activated cation channel channelrhodopsin-2 (ChR2), and the light-activated chloride pump halorhodopsin (Halo/NpHR), when transgenically expressed in cell such as neurons, make them sensitive to being activated by blue light, and silenced by yellow light, respectively (Han, X. and E. S. Boyden, 2007, PLoS ONE 2(3): e299; Boyden, E. S., et. al., 2005, Nat Neurosci. 2005 September; 8(9):1263-8. Epub 2005 Aug. 14.). Previously identified light-activated pumps and channels have been restricted to activation by particular wavelengths of light, thus limiting their usefulness.

SUMMARY OF THE INVENTION

The invention, in part, relates to isolated light-activated ion pump (LAIP) polypeptides and methods of their preparation and use. The invention also includes isolated nucleic acid sequences that encode light-driven ion pumps of the invention as well as vectors and constructs that comprise such nucleic acid sequences. In addition, the invention in some aspects includes expression of light-activated ion pump polypeptides in cells, tissues, and organisms as well as methods for using the light-activated ion pumps to alter cell and tissue function and for use in diagnosis and treatment of disorders.

The invention, in part, also relates to methods for adjusting the voltage potential of cells, subcellular regions, or extracellular regions. Some aspects of the invention include methods of incorporating at least one nucleic acid sequence encoding a light-driven ion pump into at least one target cell, subcellular region, or extracellular region, the ion pump functioning to change transmembrane potential in response to a specific wavelength of light. Exposing an excitable cell that includes an expressed light-driven ion pump of the invention to a wavelength of light that activates the pump, results in hyperpolarizing voltage change in the excitable cell. By contacting a cell that includes a LAIP of the invention with particular wavelengths of light in the red spectrum, the cell is hyperpolarized strongly enough to shift the voltage potential of the excitable cell to a level that silences spike activity of the excitable cell. A plurality of light-activated ion pumps activated by different wavelengths of light may be used to achieve multi-color excitable cell silencing.

Methods and LAIPs of the invention can be used for neural silencing, that is, hyperpolarizing a neuron to prevent it from depolarizing, spiking, or otherwise signaling (e.g., to release neurotransmitters). A LAIP of the invention can be used in conjunction with one or more other light-activated membrane proteins for multi-color neural silencing (e.g., Ace or Mac, and Halo), expressing them in different populations of cells in a tissue or in a dish, and the illuminating them each with different colors of light.

The ability to optically perturb, modify, or control cellular function offers many advantages over physical manipulation mechanisms, such as speed, non-invasiveness, and the ability to easily span vast spatial scales from the nanoscale to macroscale. One such approach is an opto-genetic approach, in which heterologously expressed light-activated membrane polypeptides such as a LAIP of the invention, are used to move ions with various spectra of light.

According to some aspects of the invention, isolated light-activated ion pump polypeptides that when expressed in an excitable cell and contacted with a red light silences the excitable cell, wherein the polypeptide sequence of the light-activated ion pump comprises a wild-type or modified *halomicrobium* or *haloarcula* halorhodopsin polypeptide sequence, are provided. In certain embodiments, the modified *haloarcula* or *halomicrobium* halorhodopsin polypeptide sequence comprises the amino acid sequence of a wild-type *haloarcula* or *halomicrobium* halorhodopsin, respectively, with one, two, or more amino acid modifications. In certain embodiments, the modified *haloarcula* halorhodopsin polypeptide has the amino acid sequence of Halo57 (SEQ ID NO:2); Gene4 (SEQ ID NO:4); Gene58 (SEQ ID NO:6); Gene56 (SEQ ID NO:8); Gene55 (SEQ ID NO:10); and the modified *halomicrobium* halorhodopsin polypeptide has the amino acid sequence of Gene54 (SEQ ID NO:12), with one, two, or more amino acid modifications. In some embodiments, the modified *haloarcula* or *halomicrobium* halorhodopsin polypeptide sequence comprises one or more of: a) a K→R, K→H, or K→Q substitution at an amino acid residue corresponding to amino acid 200 of the amino acid sequence of Halo57 (SEQ ID NO:2); b) a T→S substitution at an amino acid residue corresponding to amino acid 111 of the amino acid sequence of Halo57 (SEQ ID NO:2); c) a T→S substitution at an amino acid residue corresponding to amino acid 203 of the amino acid sequence of Halo57 (SEQ ID NO:2); or d) a K→Q+W→F double substitution at the amino acid residues corresponding to amino acid 200 and 214, respectively, of the amino acid sequence of Halo57 (SEQ ID NO:2). In some embodiments, the modified *halobacterium* halorhodopsin polypeptide sequence comprises a K→R modification and a W→F modification at the amino acid residues corresponding to amino acid 200 and 214, respectively, of the amino acid sequence of Halo57 (SEQ ID NO:2). In certain embodiments, the modified *haloarcula* halorhodopsin polypeptide sequence is the sequence set forth as SEQ ID NO:26. In some embodiments, the light-activated ion pump expressed is activated by contacting the pump with light having a wavelength in the range from about 450 nm to about 690 nm. In some embodiments, the wavelength of the red light is in the range of about 620 nm to about 690 nm.

According to another embodiment, cells that include any embodiment of an aforementioned aspect of the invention are provided. In some embodiments, the light-activated ion pump is activated and the cell hyperpolarized when the light-activated ion pump is contacted with light under suitable conditions for hyperpolarization. In certain embodiments, the light-activated ion pump is activated and the cell silenced when the light-activated ion pump is contacted with red light under suitable conditions for silencing. In some embodiments, the cell is an excitable cell. In some embodiments, the cell is a non-excitable cell. In certain embodiments, the cell is a mammalian cell. In some embodiments, the cell is in vitro, ex vivo, or in vivo. In some embodiments, the cell also includes one, two, three, four, or more additional light-activated ion pumps, wherein at least one, two, three, four, or more of the additional light-activated ion pumps is activated by contact with light having a non-red light wavelength.

According to another aspect of the invention an isolated nucleic acid sequence that encodes any embodiment of an aforementioned isolated light-activated ion pump polypeptide, is provided. In some embodiments, the nucleic acid sequence is a mammalian codon-optimized DNA sequence. In certain embodiments, the light-activated ion pump encoded by the nucleic acid sequence is expressed in the cell.

According to another aspect of the invention, vectors that include any embodiment of an aforementioned nucleic acid sequence are provided. In some embodiments, the nucleic acid sequence is operatively linked to a promoter sequence. In some embodiments, the vector also includes one, two, or more nucleic acid signal sequences operatively linked to the nucleic acid sequence encoding the light-activated ion pump. In certain embodiments, the vector is a plasmid vector, cosmid vector, viral vector, or an artificial chromosome.

According to another aspect of the invention, cells that include any embodiment of an aforementioned vector, are provided. In some embodiments, the cell also includes one, two, three, four, or more additional light-activated ion pumps, wherein at least one, two, three, four, or more of the additional light-activated ion pumps is activated by contact with light having a non-red light wavelength.

According to another aspect of the invention, methods of hyperpolarizing a cell are provided. The methods include expressing in a cell an embodiment of an aforementioned isolated light-activated ion pump polypeptide, and contacting the isolated light-activated ion pump with a light that activates the isolated light-activated ion pump and hyperpolarizes the cell. In some embodiments, the light is a red light that hyperpolarizes and silences the cell. In certain embodiments, the cell is in vivo, ex vivo, or in vitro. In some embodiments, the method also includes delivering to the cell a nucleic acid sequence that encodes the isolated light-activated ion pump. In some embodiments, the nucleic acid sequence is delivered by means of a vector. In some embodiments, the modified *haloarcula* or *halomicrobium* halorhodopsin polypeptide comprises the amino acid sequence of a wild-type *haloarcula* or *halomicrobium* halorhodopsin polypeptide, respectively with one, two, or more amino acid modifications. In certain embodiments, the modified *haloarcula* or *halomicrobium* halorhodopsin polypeptide sequence comprises one or more of: a) a K→R, K→H, or K→Q substitution at an amino acid residue corresponding to amino acid 200 of the amino acid sequence of Halo57 (SEQ ID NO:2); b) a T→S substitution at an amino acid residue corresponding to amino acid 111 of the amino acid sequence of Halo57 (SEQ ID NO:2); c) a T→S substitution at an amino acid residue corresponding to amino acid 203 of the amino acid sequence of Halo57 (SEQ ID NO:2); or d) a K→Q+W→F double substitution at the amino acid residues corresponding to amino acid 200 and 214, respectively, of the amino acid sequence of Halo57 (SEQ ID NO:2). In some embodiments, the modified *haloarcula* or *halomicrobium* halorhodopsin polypeptide sequence comprises a K→R modification and a W→F modification at amino acid residues corresponding to amino acids 200 and 214, respectively, of the amino acid sequence of Halo57 (SEQ ID NO:2). In some embodiments, the modified *haloarcula* halorhodopsin polypeptide sequence is the sequence set forth as SEQ ID NO:26. In certain embodiments, the light-activated ion pump is activated and the cell silenced when the light-activated ion pump is contacted with a red light under suitable conditions for silencing. In some embodiments, the light-activated ion pump is activated by contact with light having a wavelength from about 450 nm to about 690 nm. In certain embodiments, the red light has a wavelength from about 620 nm to about 690 nm. In some embodiments, the cell is a nervous system cell, a neuron, a cardiac cell, a circulatory system cell, a visual system cell, an auditory system cell, a hemoglobin-rich cell, or a muscle cell. In some embodiments, wherein the cell is an excitable cell. In some embodiments, the cell is a non-excitable cell. In certain embodiments, the cell is a mammalian cell. In some embodiments, the cell also includes one, two, three, or more additional light-activated ion pumps, wherein at least one, two, three, four, or more of the additional light-activated ion pumps is activated by contact with light having a non-red light wavelength. In some embodiments, the cell is in a subject and hyperpolarizing the cell diagnoses or assists in a diagnosis of a disorder in the subject. In some embodiments, the cell is in a subject and silencing the cell diagnosis or assists in a diagnosis of a disorder in the subject. In certain embodiments, the cell is in a subject and hyperpolarizing the cell treats a disorder in the subject. In some embodiments, the cell is in a subject and silencing the cell treats a disorder in the subject.

According to yet another aspect of the invention, methods of identifying an effect of a candidate compound on a cell are provided. The methods include contacting a test cell comprising an isolated light-activated ion pump of any embodiment of an aforementioned aspect, with a light under conditions suitable to activate the ion pump and hyperpolarize the test cell; contacting the test cell with a candidate compound; and identifying the presence or absence of a change in the hyperpolarization or in a hyperpolarization-mediated cell characteristic in the test cell contacted with the light and the candidate compound compared to the hyperpolarization or the hyperpolarization-mediated cell characteristic, respectively, in a control cell contacted with the light and not contacted with the candidate compound; wherein a change in the hyperpolarization or the hyperpolarization-mediated cell characteristic in the test cell compared to the control identifies an effect of the candidate compound on the test cell. In some embodiments, the effect of the candidate compound is an effect on the hyperpolarization of the test cell. In some embodiments, the effect of the candidate compound is an effect on a hyperpolarization-mediated cell characteristic in the test cell. In certain embodiments, the hyperpolarization mediated cell characteristic is a hyperpolarization-activated conductance. In some embodiments, the hyperpolarization-activated conductance is the result of a T-type calcium channel activity, a BK channel activity, or an I_h current. In some embodiments, the hyperpolarization mediated-cell characteristic is cell silencing. In some embodiments, the modified *haloarcula* or *halomicrobium* halorhodopsin polypeptide sequence comprises the amino acid sequence of a wild-type *haloarcula* or *halomicrobium* halorhodopsin polypeptide, respectively, with one, two, or more amino acid modifications. In certain embodiments, the modified *haloarcula* or *halomicrobium* halorhodopsin polypeptide sequence comprises one or more of: a) a K→R, K→H, or K→Q substitution at an amino acid residue corresponding to amino acid 200 of the amino acid sequence of Halo57 (SEQ ID NO:2); b) a T→S substitution at an amino acid residue corresponding to amino acid 111 of the amino acid sequence of Halo57 (SEQ ID NO:2); c) a T→S substitution at an amino acid residue corresponding to amino acid 203 of the amino acid sequence of Halo57 (SEQ ID NO:2); or d) a K→Q+W→F double substitution at the amino acid residues corresponding to amino acid 200 and 214, respectively, of the amino acid sequence of Halo57 (SEQ ID NO:2). In some embodiments, the modified *haloarcula* or *halomicrobium* halorhodopsin polypeptide sequence comprises a K→R modification and a W→F modification at the amino acid residues corresponding to amino acid 200 and 214, respectively, of the amino acid sequence of Halo57 (SEQ ID NO:2). In some embodiments, the modified *haloarcula* halorhodopsin polypeptide sequence is the sequence set forth as SEQ ID NO:26. In certain embodiments, the method also includes characterizing the change identified in the hyperpolarization or the hyperpolarization-mediated cell characteristic. In some embodiments, the method also includes contacting the light-activated ion pump with a red light, wherein the red light silences the cell. In some embodiments, the light-activated ion pump is activated by contacting the pump with light having a wavelength from about 450 nm to about 690 nm. In some embodiments, the red-light has a wavelength from about 620 nm to about 690 nm. In certain embodiments, the test cell is a nervous system cell, a neuron, a cardiac cell, a circulatory system cell, a visual system cell, an auditory system cell, a hemoglobin-rich cell, or a muscle cell. In some embodiments, the test cell is an excitable cell. In some embodiments, the test cell is a non-excitable cell. In some embodiments, the test cell is a mammalian cell. In certain embodiments, the cell also includes one, two, three, or more additional light-activated ion pumps, wherein at least one, two, three, four, or more of the additional light-activated ion pumps is activated by contact with light having a non-red light wavelength.

According to another aspect of the invention, methods of treating a disorder in a subject are provided. The methods include administering to a subject in need of such treatment, a therapeutically effective amount of a light-activated ion pump any embodiment of an aforementioned aspect, to treat the disorder. In some embodiments, the light-activated ion pump is administered in the form of a cell, wherein the cell expresses the light-activated ion pump; or in the form of a vector, wherein the vector comprises a nucleic acid sequence encoding the light-activated ion pump and the administration of the vector results in expression of the light-activated ion pump in a cell in the subject. In some embodiments, the method also includes contacting the cell with light and activating the light-activated ion pump in the cell. In certain embodiments, the method also includes contacting the cell with red light and activating and silencing the light-activated ion pump in the cell. In some embodiments, the cell is a nervous system cell, a neuron, a cardiac cell, a circulatory system cell, a visual system cell, an auditory system cell, a hemoglobin-rich cell, or a muscle cell. In some embodiments, the vector further comprises a signal sequence. In some embodiments, the vector further comprises a cell-specific promoter. In certain embodiments, the disorder is a neurological disorder, a visual system disorder, a circulatory system disorder, a musculoskeletal system disorder, or an auditory system disorder.

According to another aspect of the invention, isolated light-activated ion pump polypeptides that when expressed in an excitable cell and contacted with a red light silences the excitable cell are provided and the polypeptide sequence of the light-activated ion pump comprises a modified Halobacteriaceae halorhodopsin polypeptide sequence, and the modified halorhodopsin polypeptide sequence comprises one or more of a) a K→R, K→H, or K→Q substitution at an amino acid residue corresponding to amino acid 200 of the amino acid sequence of Halo57 (SEQ ID NO:2); b) a T→S substitution at an amino acid residue corresponding to amino acid 111 of the amino acid sequence of Halo57 (SEQ ID NO:2); c) a T→S substitution at an amino acid residue corresponding to amino acid 203 of the amino acid sequence of Halo57 (SEQ ID NO:2); or d) a K→Q+W→F double substitution at the amino acid residues corresponding to amino acid 200 and 214, respectively, of the amino acid sequence of Halo57 (SEQ ID NO:2). In some embodiments, the modified halorhodopsin polypeptide sequence comprises a K→R substitution at an amino acid residue corresponding to amino acid 200 of the amino acid sequence of Halo57 (SEQ ID NO:2) and further comprises a W→F substitution at the amino acid residue corresponding to amino acid 214 of the amino acid sequence of Halo57 (SEQ ID NO:2). In some embodiments, the sequence of the light-activated ion pump polypeptide is the sequence set forth as SEQ ID NO:26.

According to another aspect of the invention, cells that include any embodiment of an aforementioned isolated light-activated ion pump polypeptide are provided. In some embodiments, the cell is an excitable cell. In certain embodiments, the cell is a non-excitable cell. In some embodiments, the cell is a mammalian cell. In some embodiments, the cell is in vitro, ex vivo, or in vivo. In certain embodiments, the cell also includes one, two, three, four, or more additional light-activated ion pumps, wherein at least one, two, three, four, or more of the additional light-activated ion pumps is activated by contact with light having a non-red light wavelength.

According to another aspect of the invention, nucleic acid sequences that encode any embodiment of an aforementioned isolated light-activated ion pump polypeptide are provided. According to yet another aspect of the invention, vectors that include any embodiment of an aforementioned nucleic acid sequence are provided. In some embodiments, the vector also includes one, two, or more nucleic acid signal sequences operatively linked to the nucleic acid sequence encoding the light-activated ion pump.

According to another aspect of the invention, cells that include any embodiment of an aforementioned vector are provided. In some embodiments, the cell is an excitable cell, and optionally a mammalian cell. In some embodiments, the cell is a non-excitable cell. In certain embodiments, the cell is in vitro, ex vivo, or in vivo. In some embodiments, the cell also includes one, two, three, four, or more additional light-activated ion pumps, wherein at least one, two, three, four, or more of the additional light-activated ion pumps is activated by contact with light having a non-red light wavelength.

According to yet another aspect of the invention, methods of hyperpolarizing a cell are provided. The methods include contacting a cell comprising any embodiment of an aforementioned isolated light-activated ion pump polypeptide with a light under conditions suitable to activate the ion pump and hyperpolarize the cell. In some embodiments, the light is a red light that hyperpolarizes and silences the cell. In certain embodiments, the method also includes delivering to the cell a nucleic acid sequence that encodes the isolated light-activated ion pump. In some embodiments, the cell is a mammalian cell. In some embodiments, the cell is in a subject and hyperpolarizing the cell diagnoses or assists in a diagnosis of a disorder in the subject. In certain embodiments, the cell is in a subject and silencing the cell diagnosis or assists in a diagnosis of a disorder in the subject. In some embodiments, the cell is in a subject and hyperpolarizing the cell treats a disorder in the subject. In some embodiments, the cell is in a subject and silencing the cell treats a disorder in the subject. In some embodiments, the sequence of the light-activated ion pump polypeptide the sequence set forth as SEQ ID NO:26.

According to another aspect of the invention, methods of identifying an effect of a candidate compound on a cell are provided. The methods include a) contacting a test cell comprising any embodiment of an aforementioned isolated light-activated ion pump polypeptide with a light under suitable conditions to activate the ion pump and hyperpolarize the test cell; b) contacting the test cell with a candidate compound; and c) identifying the presence or absence of a change in the hyperpolarization or in a hyperpolarization-mediated cell characteristic in the test cell contacted with the light and the candidate compound compared to the hyperpolarization or the hyperpolarization-mediated cell characteristic, respectively, in a control cell contacted with the light and not contacted with the candidate compound; wherein a change in the hyperpolarization or the hyperpolarization-mediated cell characteristic in the test cell compared to the control indicates an effect of the candidate compound on the test cell. In certain embodiments, the method also includes characterizing a change identified in the hyperpolarization or the hyperpolarization-mediated cell characteristic. In some embodiments, the method also includes contacting the light-activated ion pump with a red light and silencing the cell. In some embodiments, the sequence of the light-activated ion pump polypeptide the sequence set forth as SEQ ID NO:26.

According to yet another aspect of the invention, methods of treating a disorder in a subject are provided. The methods include, administering to a subject in need of such treatment, a therapeutically effective amount of any embodiment of an aforementioned light-activated ion pump polypeptide to treat the disorder. In some embodiments, the light-activated ion pump is administered in the form of a cell, wherein the cell expresses the light-activated ion pump or in the form of a vector, wherein the vector comprises a nucleic acid sequence encoding the light-activated ion pump and the administration of the vector results in expression of the light-activated ion pump in a cell in the subject. In certain embodiments, the method also includes contacting the cell with light and activating the light-activated ion pump in the cell. In some embodiments, the method also includes contacting the cell with red light and activating and silencing the light-activated ion pump in the cell. In some embodiments, the cell is a nervous system cell, a neuron, a cardiac cell, a circulatory system cell, a visual system cell, an auditory system cell, a hemoglobin-rich cell, an integumentary system cell, or a muscle cell. In some embodiments, the vector further comprises a signal sequence. In certain embodiments, the vector further comprises a cell-specific promoter. In some embodiments, the disorder is a neurological disorder, a visual system disorder, a circulatory system disorder, or an auditory system disorder. In some embodiments, the sequence of the light-activated ion pump polypeptide the sequence set forth as SEQ ID NO:26.

BRIEF DESCRIPTION OF THE DRAWINGS

FIG. 3 is an illustration showing the amino acid sequence alignment of rhodopsin sequences for: Halo57 (SEQ ID NO:2); Gene4 (SEQ ID NO:4); Gene58 (SEQ ID NO:6); Gene56 (SEQ ID NO:8); Gene55 (SEQ ID NO:10); Gene54 (SEQ ID NO:12) and Halo (SEQ ID NO:14).

FIG. 4A shows the trough of hemoglobin absorption and shows results indicating that oxygen-bound hemoglobin absorbs 24 times more light at 593 nm illumination than at 660 nm, near its trough of absorbance. FIG. 4B shows results indicating that Halo57 redshift, which allows illumination at the hemoglobin absorption trough.

FIG. 5B is a histogram showing that the photocurrents for the *Halobacterium salinarum* (strain shark/*Halobacterium halobium* (strain shark) halorhodopsin can be further improved by the K200R+W214F double mutation.

FIG. 6A shows photocurrent results for Halo (wild-type) and Halo that includes the single mutations: (K215R) and (W229F) and the double mutation [(K215R)+(W229F] and shows photocurrent results for Halo57 (wild-type) and Halo57 that includes the single mutations (K200R) and (W214F) and the double mutation [(K200R)+(W214F)]. The position of the Halo sequence mutations correspond to the positions of the mutations in the Halo57 sequence. FIG. 6B shows wildtype-normalized photocurrents for Halo versus Halo57. In FIG. 6B, the first bar of each pair is Halo, and the second bar is Halo57. All of the values were normalized relative to the wildtype (mutant/wildtype). The experiment demonstrated the significantly different effect of the substitutions on Halo and Halo57 photocurrents. The left-most pair of bars shows Halo (left) and Halo57 (right) wild-type normalized to themselves. The second pair of bars from left show that K215R substitution dropped Halo photocurrents but the corresponding substitution in Halo57 (K200R) boosted Halo57 photocurrent by approximately 70%. The third set of bars from left show that W229F (equivalent=W214F in Halo57) lowered both Halo and Halo57, and finally the far right pair of bars shows that the double mutation significantly lowered Halo photocurrent and substantially boosted Halo57 photocurrent.

FIG. 7 provides screen data showing outward photocurrents for Halo57 mutant with different appended cell trafficking signal sequences, measured by whole-cell patch-clamp of cultured neurons under screening illumination conditions (575±25 nm, 14.2 mW/mm$^2$). Data are mean and s.e. Each bar demonstrates the different amounts of photocurrent generated when illuminated with 570/50 nm light.

BRIEF DESCRIPTION OF THE SEQUENCES

Figure 1:
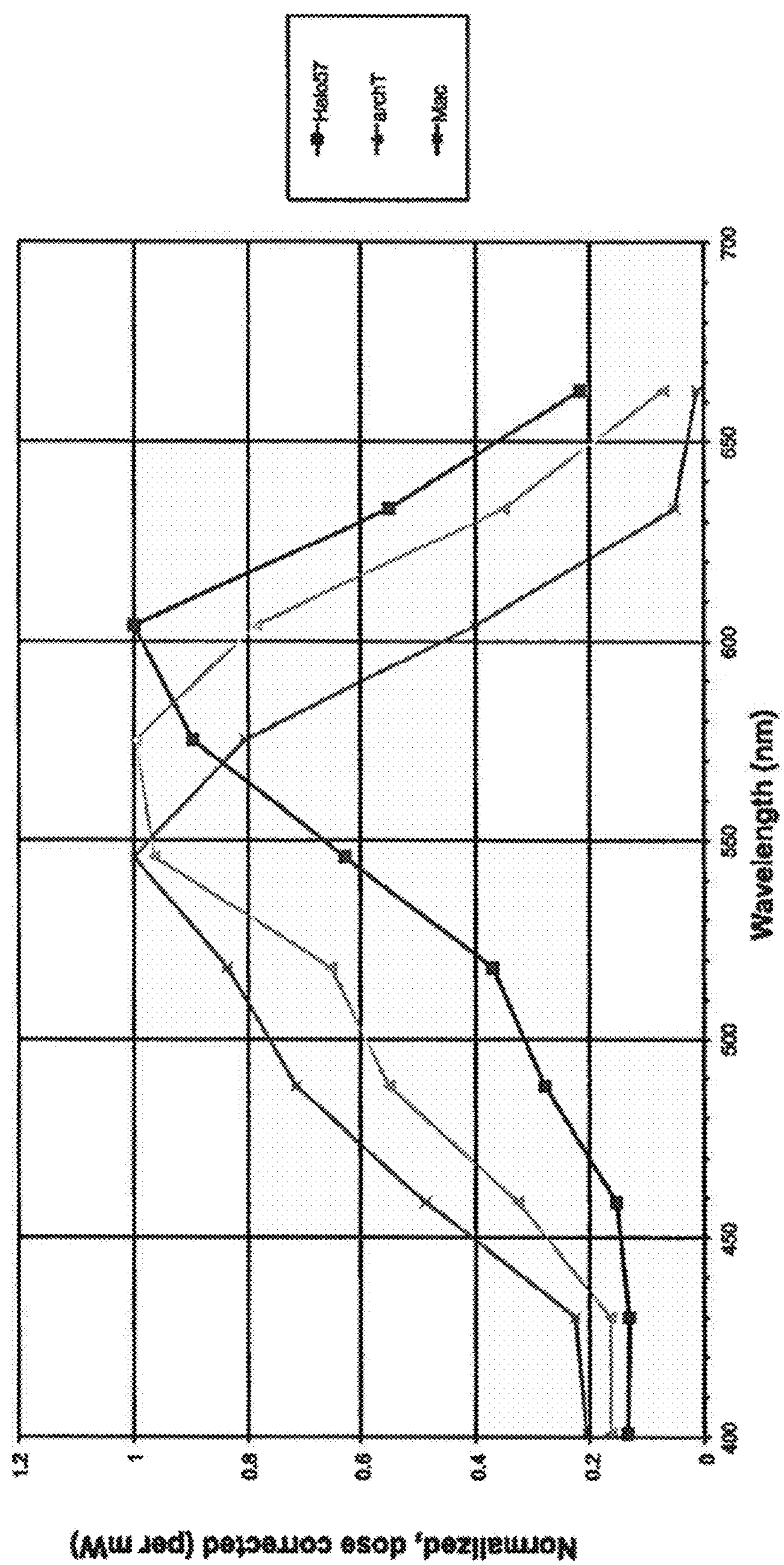
FIG. 1 is a graph showing Photocurrent normalized action spectra for Halo57, ArchT and Mac, demonstrating that Halo57 (the *Halobacterium salinarum* (strain shark)/*Halobacterium halobium* (strain shark) gene for halorhodopsin) is significantly red-light shifted relative to other opsins.

SEQ ID NO: 1 is the mammalian codon-optimized DNA sequence that encodes Halo57, the gene for the *Halobacterium salinarum* (strain shark) halorhodopsin:

atgaccgccgtgagcaccacagccactaccgtgctgcaggccacacagagcgacgtgctgcaggagatccagtccaacttcctgct gaatagctccatctgggtgaacattgctctggccggagtggtcatcctgctgtttgtggccatggggagggatctggaatcccctagag ctaagctgatctgggtggccacaatgctggtgccactggtgtctatttctagttacgctggactggccagtgggctgactgtgggcttcc tgcagatgccacctggacacgctctggccggacaggaggtgctgagcccatggggccggtatctgacatggactttctccactccca tgatcctgctggctctgggactgctggccgacaccgatattgccagcctgttcaccgccatcacaatggacattggcatgtgcgtgaca ggactggccgctgccctgatcactagctcccatctgctgcgctgggtgttctacggaatttcttgtgctttctttgtggccgtgctgtatgt gctgctggtgcagtggccagctgatgctgaggctgctgggaccagtgaaatctttggcactctgaagattctgaccgtggtgctgtgg ctggggtaccctatcctgtgggctctgggctctgagggagtggccctgctgagtgtgggagtgaccagctggggatactccggactg gacatcctggctaaatacgtgttcgcctttctgctgctgagatgggtggctgccaatgaaggcacagtgtctgggagtggaatgggaat cgggtccggaggagctgctccagccgacgat.

SEQ ID NO: 2 is the amino acid sequence of Halo57, the gene for the *Halobacterium salinarum* (strain shark) halorhodopsin:

MTAVSTTATTVLQATQSDVLQEIQSNFLLNSSIWVNIALAGVVILLFVAMGRDLESP

RAKLIWVATMLVPLVSISSYAGLASGLTVGFLQMPPGHALAGQEVLSPWGRYLTWT

FSTPMILLALGLLADTDIASLFTAITMDIGMCVTGLAAALITSSHLLRWVFYGISCAFF

VAVLYVLLVQWPADAEAAGTSEIFGTLKILTVVLWLGYPILWALGSEGVALLSVGV

TSWGYSGLDILAKYVFAFLLLRWVAANEGTVSGSGMGIGSGGAAPADD.

SEQ ID NO: 3 is the mammalian codon-optimized DNA sequence that encodes Gene4, the gene for *Haloarcula marismortui* cruxhalorhodopsin halorhodopsin:

Atgacagccgccagcaccaccgccaccaccgtgctgcaggccacacagtccgacgtgctgcaggagatccagagcaacttcctg ctgaactccagcatctgggtgaacattgccctggccggcgtggtgatcctgctgtttgtggccatgggccgcgacctggaaagcccc cgcgccaagctgatttgggtggccacaatgctggtgcccctggtgtccatcagcagctatgccggactggccagcggactgaccgtg ggatttctgcagatgccccccggccacgccctggccggccaggaggtgctgtccccctggggccggtacctgacatggacattctc cacccctatgatcctgctggccctgggactgctggccgatacagacatcgcctctctgttcaccgccatcaccatggacatcgggatgt -continued gcgtgaccggactggccgccgccctgatcaccagctcccacctgctgcgctgggtgttctacggcatctcttgcgcctttttcgtggcc gtgctgtacgtgctgctggtgcagtggcccgccgacgccgaggccgccggcaccagcgagatcttcggcacactgaagattctgac agtggtgctgtggctgggatacccaatcctgtgggccctgggctctgagggcgtggccctgctgagcgtgggagtgacctcttgggg ctacagcggactggacattctggccaagtacgtgttcgccttcctgctgctgaggtgggtggccgccaatgaaggaacagtgtctggg tccggcatgggcatcggctccgggggcgccacacctgccgacgac.

SEQ ID NO: 4 is the amino acid sequence of Gene4, the gene for *Haloarcula marismortui* cruxhalorhodopsin halorhodopsin:
MTAASTTATTVLQATQSDVLQEIQSNFLLNSSIWVNIALAGVVILLFVAMGRDLESP

RAKLIWVATMLVPLVSISSYAGLASGLTVGFLQMPPGHALAGQEVLSPWGRYLTWT

FSTPMILLALGLLADTDIASLFTAITMDIGMCVTGLAAALITSSHLLRWVFYGISCAFF

VAVLYVLLVQWPADAEAAGTSEIFGTLKILTVVLWLGYPILWALGSEGVALLSVGV

TSWGYSGLDILAKYVFAFLLLRWVAANEGTVSGSGMGIGSGGATPADD.

SEQ ID NO: 5 is the mammalian codon-optimized DNA sequence that encodes Halo58), the gene for *Halobacterium salinarum* (strain port) halorhodopsin:
atgaccgccgcttccaccacagctactaccatgctgcaggccacacagtctgacgtgctgcaggagatccagagtaacttcctgctga atagctccatctgggtgaacattgctctggccggggtggtcatcctgctgtttgtggccatgggcagggatatcgaatctectagagcta agctgatttgggtggccacaatgctggtgccactggtgagcatctctagttacgctgggctggcctccggactgactgtgggattcctg cagatgccacctggacacgctctggccggacaggaggtgctgtctccatggggccggtatctgacatggactttcagtactcccatga tcctgctggctctgggactgctggccgacaccgatattgccagcctgttcaccgccatcacaatggacattggaatgtgcgtgacagg gctggccgctgccctgatcactagctcccatctgctgcgctgggtgttctacggaatttcttgtgctttctttgtggccgtgctgtatgtgct gctggtgcagtggccagctgatgctgaggctgctggcaccagcgaaatctttggaactctgaagattctgaccgtggtgctgtggctg ggtaccctatcctgtgggctctgggaagcgagggagtggccctgctgtccgtgggagtgacatcttggggctacagtggactgga cattctggctaaatacgtgttcgcctttctgctgctgagatgggtggctgccaatgaaggagccgtgtctgggagtggaatgagcatcg ggtccggaggagctgctccagccgacgat.

SEQ ID NO: 6 is the amino acid sequence of Halo58 (also referred to herein as Gene58), the gene for *Halobacterium salinarum* (strain port) halorhodopsin:
MTAASTTATTMLQATQSDVLQEIQSNFLLNSSIWVNIALAGVVILLFVAMGRDIESPR

AKLIWVATMLVPLVSISSYAGLASGLTVGFLQMPPGHALAGQEVLSPWGRYLTWTF

STPMILLALGLLADTDIASLFTAITMDIGMCVTGLAAALITSSHLLRWVFYGISCAFFV

AVLYVLLVQWPADAEAAGTSEIFGTLKILTVVLWLGYPILWALGSEGVALLSVGVT

SWGYSGLDILAKYVFAFLLLRWVAANEGAVSGSGMSIGSGGAAPADD.

SEQ ID NO:7 is the mammalian codon optimized DNA sequence of Gene56, which encodes the *Haloarcula sinaiiensis* (ATCC 33800) halorhodopsin:
atgctgcaggagatccagtctaacttcctgctgaatagctccatctgggtgaacattgctctggccggagtggtcatcctgctgtttgtgg ccatggggagggacctggaaagtectagagctaagctgatctgggtggccaccatgctggtgccactggtgagcatttctagttacgc tggactggcctccggactgacagtgggcttcctgcagatgccacctggacacgctctggccggacaggaggtgctgtctccatggg gccggtatctgacctggacattcagtacacccatgatcctgctggctctgggactgctggccgacactgatattgcttctctgtttactgc catcaccatggacattggcatgtgcgtgactggactggccgctgccctgatcaccagctcccatctgctgcgctgggtgttctacggaa ttagctgtgctttctttgtggccgtgctgtatgtgctgctggtgcagtggccagctgatgctgaggctgctgggacttccgaaatctttgg caccctgaagattctgacagtggtgctgtggctggggtaccctatcctgtgggctctgggctctgagggagtggccctgctgagtgtg ggcgtgacaagctgggggtactccggcctggatatcctggctaaatacgtgttcgcctttctgctgctgagatgggtggccacaaatg aaggcaccgtgagcgggagtggaatgggaatcgggtccggaggagctgctccagccgacgat.

SEQ ID NO: 8 is the amino acid sequence of Gene56, which is a *Haloarcula sinaiiensis* (ATCC 33800) halorhodopsin:
MLQEIQSNFLLNSSIWVNIALAGVVILLFVAMGRDLESPRAKLIWVATMLVPLVSISS -continued

YAGLASGLTVGFLQMPPGHALAGQEVLSPWGRYLTWTFSTPMILLALGLLADTDIA

SLFTAITMDIGMCVTGLAAALITSSHLLRWVFYGISCAFFVAVLYVLLVQWPADAEA

AGTSEIFGTLKILTVVLWLGYPILWALGSEGVALLSVGVTSWGYSGLDILAKYVFAF

LLLRWVATNEGTVSGSGMGIGSGGAAPADD.

SEQ ID NO: 9 is the DNA sequence of Gene55, which encodes *Haloarcula californiae* (ATCC 33799) halorhodopsin:
Atgaacatcgctctggccggagtggtcatcctgctgttcgtggctatgggaagggacctggagtcccctagagctaagctgatctgg gtggccaccatgctggtgccactggtgtctattagctcctacgctggactggccagtgggctgacagtgggctttctgcagatgccacc tggacacgctctggccggacaggaagtgctgagcccatggggccggtatctgacctggacattctccacacccatgatcctgctggc tctgggactgctggccgacactgatattgcttctctgtttactgccatcaccatggacattggcatgtgcgtgactggactggccgctgc cctgatcacctctagtcatctgctgcgctgggtgttctacggaatttcttgtgattattgtggccgtgctgtatgtgctgctggtgcagtg gccagctgatgctgaggctgctgggactagtgaaatctttggcaccctgaagattctgacagtggtgctgtggctggggtaccctatcc tgtgggctctgggcagcgagggagtggccctgctgtccgtgggagtgacatcttgggggtacagtggcctggatattctggctaaata cgtgttcgcattctgctgctgagatgggtggccacaaatgaaggcactgtgagcgggtccggaatgggaatcgggagcggaggag ctgccccagccgacgat.

SEQ ID NO: 10 is the amino acid sequence of Gene55, which is the *Haloarcula californiae* (ATCC 33799) halorhodopsin:
MNIALAGVVILLFVAMGRDLESPRAKLIWVATMLVPLVSISSYAGLASGLTVGFLQ

MPPGHALAGQEVLSPWGRYLTWTFSTPMILLALGLLADTDIASLFTAITMDIGMCVT

GLAAALITSSHLLRWVFYGISCAFFVAVLYVLLVQWPADAEAAGTSEIFGTLKILTV

VLWLGYPILWALGSEGVALLSVGVTSWGYSGLDILAKYVFAFLLLRWVATNEGTVS

GSGMGIGSGGAAPADD.

SEQ ID NO: 11 is the DNA sequence of Gene54, which encodes *Halomicrobium mukohataei* DSM 12286 halorhodopsin:
Atgtccgccaccacaactctgctgcaggctactcagtctgaggctgtgaccgccatcgaaaacgacgtgctgctgagctcctctctgt gggctaatgtggctctggccggcctggctatcctgctgttcgtgtatatgggaaggaacgtggaggctccaagagccaagctgatttg gggagccaccctgatgatcccccctggtgagtattagtagctatctgggactgctgagcggactgacagtgggcttcatcgaaatgcct gctggacacgctctggccggagaggaagtgatgagtcagtggggcaggtacctgacttgggccctgtccaccccaatgatcctgct ggctctgggactgctggccgacgtggatattggggacctgttcgtggtcatcgccgctgatattggaatgtgcgtgacagggctggcc gctgccctgatcacttctatacggcctgcggtgggcctttttatctggtgtatgtgctttctttctggtggtgctgtacgctatcctggtgg agtggccacagagcgccaccgctgctgggacagacgaaattttcggcacactgcgcgccctgactgtggtgctgtggctgggatatc ctatcatttgggctgtgggaatcgagggactggctctggtgcagtccgtgggcctgaccagttggggatacagcgccctggatattgg ggccaaatatctgttcgcttttctgctgctgcggtgggtggctgccaatcaggacgtggtggggcagccctccctggatacccattctg aaggcacagctcctgccgacgat.

SEQ ID NO: 12 is the amino acid sequence of Gene54, which is *Halomicrobium* mukohataei DSM 12286 halorhodopsin:
MSATTTLLQATQSEAVTAIENDVLLSSSLWANVALAGLAILLFVYMGRNVEAPRAK

LIWGATLMIPLVSISSYLGLLSGLTVGFIEMPAGHALAGEEVMSQWGRYLTWALSTP

MILLALGLLADVDIGDLFVVIAADIGMCVTGLAAALITSSYGLRWAFYLVSCAFFLV

VLYAILVEWPQSATAAGTDEIFGTLRALTVVLWLGYPIIWAVGIEGLALVQSVGLTS

WGYSALDIGAKYLFAFLLLRWVAANQDVVGQPSLDTHSEGTAPADD.

SEQ ID NO: 13 is the DNA sequence of Halo, which encodes *Natromonas pharaonis* halorhodopsin:
Atgactgagaccctcccacccgtgactgaaagcgccgtcgctctgcaagcagaggttacccagcgggagctgttcgagttcgtcctc aacgacccccctcctggcttctagcctctacatcaacattgctctggcaggcctgtctatactgctgttcgtcttcatgaccaggggactcg atgaccctagggctaaactgattgcagtgagcacaattctggttcccgtggtctctatcgcttcctacactgggctggcatctggtctcac -continued aatcagtgtcctggaaatgccagctggccactttgccgaagggagttctgtcatgctgggaggcgaagaggtcgatggggttgtcac aatgtggggtcgctacctcacctgggctctcagtacccccatgatcctgctggcactcggactcctggccggaagtaacgccaccaa actcttcactgctattacattcgatatcgccatgtgcgtgaccgggctcgcagctgccctcaccaccagcagccatctgatgagatggtt ttggtatgccatctcttgtgcctgctttctggtggtgctgtatatcctgctggtggagtgggctcaggatgccaaggctgcagggacagc cgacatgtttaatacactgaagctgctcactgtggtgatgtggctgggttaccctatcgtttgggcactcggcgtggagggaatcgcagt tctgcctgttggtgtgacaagctggggctactccttcctggacattgtggccaagtatatttttgcctttctgctgctgaattatctgacttcc aatgagtccgtggtgtccggctccatactggacgtgccatccgccagcggcacacctgccgatgac.

SEQ ID NO: 14 is the amino acid sequence of Halo, which is *Natromonas pharaonis* halorhodopsin:
MTETLPPVTESAVALQAEVTQRELFEFVLNDPLLASSLYINIALAGLSILLFVFMTRGL

DDPRAKLIAVSTILVPVVSIASYTGLASGLTISVLEMPAGHFAEGSSVMLGGEEVDGV

VTMWGRYLTWALSTPMILLALGLLAGSNATKLFTAITFDIAMCVTGLAAALTTSSH

LMRWFWYAISCACELVVLYILLVEWAQDAKAAGTADMENTLKLLTVVMWLGYPI

VWALGVEGIAVLPVGVTSWGYSFLDIVAKYIFAFLLLNYLTSNESVVSGSILDVPSAS

GTPADD.

SEQ ID NO: 15 is the DNA sequence of the 'ss' signal sequence from truncated MHC class I antigen:
gtcccgtgcacgctgctcctgctgttggcagccgccctggctccgactcagacgcgggcc.

SEQ ID NO: 16 is the amino acid sequence of the 'ss' signal sequence from truncated MHC class I antigen:
MVPCTLLLLLAAALAPTQTRA.

SEQ ID NO: 17 is the DNA sequence of a prolactin signal sequence (also referred to herein as "Pr1":
gacagcaaaggttcgtcgcagaaagggtcccgcctgctcctgctgctggtggtgtcaaatctactcttgtgccagggtgtggtctccac
ccccgtc.

SEQ ID NO: 18 is the amino acid sequence of a prolactin signal sequence (also referred to herein as "Pr1":
MDSKGSSQKGSRLLLLLVVSNLLLCQVVS.

SEQ ID NO: 19 is the DNA sequence of the ER export sequence (also referred to herein as ER2":
ttctgctacgagaatgaagtg.

SEQ ID NO: 20 is the amino acid sequence of the ER export sequence (also referred to herein as "ER2":
FCYENEV.

SEQ ID NO: 21 is the DNA sequence of KGC, which is a C terminal export sequence from the potassium channel Kir2.1:
Aaatccagaattacttctgaaggggagtatatccctctggatcaaatagacatcaatgtt.

SEQ ID NO: 22 is the amino acid sequence of KGC, which is a C terminal export sequence from the potassium channel Kir2.1:
KSRITSEGEYIPLDQIDINV.

SEQ ID NO: 23 is the DNA sequence of a Halo-GFP fusion gene:
atgactgagaccctcccacccgtgactgaaagcgccgtcgctctgcaagcagaggttacccagcgggagctgttcgagttcgtcctc aacgacccctcctggcttctagcctctacatcaacattgctctggcaggcctgtctatactgctgttcgtcttcatgaccaggggactcg atgaccctagggctaaactgattgcagtgagcacaattctggttcccgtggtctctatcgcttcctacactgggctggcatctggtctcac aatcagtgtcctggaaatgccagctggccactttgccgaagggagttctgtcatgctgggaggcgaagaggtcgatggggttgtcac aatgtggggtcgctacctcacctgggctctcagtacccccatgatcctgctggcactcggactcctggccggaagtaacgccaccaa actcttcactgctattacattcgatatcgccatgtgcgtgaccgggctcgcagctgccctcaccaccagcagccatctgatgagatggtt ttggtatgccatctcttgtgcctgctttctggtggtgctgtatatcctgctggtggagtgggctcaggatgccaaggctgcagggacagc cgacatgtttaatacactgaagctgctcactgtggtgatgtggctgggttaccctatcgtttgggcactcggcgtggagggaatcgcagt tctgcctgttggtgtgacaagctggggctactccttcctggacattgtggccaagtatatttttgcctttctgctgctgaattatctgacttcc -continued aatgagtccgtggtgtccggctccatactggacgtgccatccgccagcggcacacctgccgatgaccgaccggtagtagcagtgag caagggcgaggagctgttcaccggggtggtgcccatcctggtcgagctggacggcgacgtaaacggccacaagttcagcgtgtcc ggcgagggcgagggcgatgccacctacggcaagctgaccctgaagttcatctgcaccaccggcaagctgcccgtgccctggccca ccctcgtgaccaccctgacctacggcgtgcagtgcttcagccgctaccccgaccacatgaagcagcacgacttcttcaagtccgccat gcccgaaggctacgtccaggagcgcaccatcttcttcaaggacgacggcaactacaagacccgcgccgaggtgaagttcgagggc gacaccctggtgaaccgcatcgagctgaagggcatcgacttcaaggaggacggcaacatcctggggcacaagctggagtacaact acaacagccacaacgtctatatcatggccgacaagcagaagaacggcatcaaggtgaacttcaagatccgccacaacatcgaggac ggcagcgtgcagctcgccgaccactaccagcagaacacccccatcggcgacggccccgtgctgctgcccgacaaccactacctga gcacccagtccgccctgagcaaagaccccaacgagaagcgcgatcacatggtcctgctggagttcgtgaccgccgccgggatcac tctcggcatggacgagctgtacaagtaa.

SEQ ID NO: 24 is the amino acid sequence of a Halo-GFP fusion polypeptide:
MTETLPPVTESAVALQAEVTQRELFEFVLNDPLLASSLYINIALAGLSILLFVFMTRGL

DDPRAKLIAVSTILVPVVSIASYTGLASGLTISVLEMPAGHFAEGSSVMLGGEEVDGV

VTMWGRYLTWALSTPMILLALGLLAGSNATKLFTAITFDIAMCVTGLAAALTTSSH

LMRWFWYAISCACELVVLYILLVEWAQDAKAAGTADMENTLKLLTVVMWLGYPI

VWALGVEGIAVLPVGVTSWGYSFLDIVAKYIFAFLLLNYLTSNESVVSGSILDVPSAS

GTPADDRPVVAVSKGEELFTGVVPILVELDGDVNGHKFSVSGEGEGDATYGKLTLK

FICTTGKLPVPWPTLVTTLTYGVQCFSRYPDHMKQHDFFKSAMPEGYVQERTIFFKD

DGNYKTRAEVKFEGDTLVNRIELKGIDEKEDGNILGHKLEYNYNSHNVYIMADKQK

NGIKVNFKIRHNIEDGSVQLADHYQQNTPIGDGPVLLPDNHYLSTQSALSKDPNEKR

DHMVLLEFVTAAGITLGMDELYK.

SEQ ID NO: 25 is the amino acid sequence of a Halo-GFP fusion polypeptide
MTETLPPVTESAVALQAEVTQRELFEFVLNDPLLASSLYINIALAGLSILLFVFMTRGL

DDPRAKLIAVSTILVPVVSIASYTGLASGLTISVLEMPAGHFAEGSSVMLGGEEVDGV

VTMWGRYLTWALSTPMILLALGLLAGSNATKLFTAITFDIAMCVTGLAAALTTSSH

LMRWEYAISCACELVVLYILLVEWAQDAKAAGTADMENTLKLLTVVMWLGYPIV

WALGVEGIAVLPVGVTSWGYSFLDIVAKYIFAFLLLNYLTSNESVVSGSILDVPSASG

TPADDRPVVAVSKGEELFTGVVPILVELDGDVNGHKFSVSGEGEGDATYGKLTLKFI

CTTGKLPVPWPTLVTTLTYGVQCFSRYPDHMKQHDFFKSAMPEGYVQERTIFFKDD

GNYKTRAEVKFEGDTLVNRIELKGIDEKEDGNILGHKLEYNYNSHNVYIIVIADKQKN

GIKVNFKIRHNIEDGSVQLADHYQQNTPIGDGPVLLPDNHYLSTQSALSKDPNEKRD

HMVLLEFVTAAGITLGMDELYK.

SEQ ID NO: 26 is the amino acid sequence of Halo57 with K200R and W214F mutations.
MTAVSTTATTVLQATQSDVLQEIQSNFLLNSSIWVNIALAGVVILLFVAMGRDLESP

RAKLIWVATMLVPLVSISSYAGLASGLTVGFLQMPPGHALAGQEVLSPWGRYLTWT

FSTPMILLALGLLADTDIASLFTAITMDIGMCVTGLAAALITSSHLLRWVFYGISCAFE

VAVLYVLLVQWPADAEAAGTSEIFGTLRILTVVLWLGYPILFALGSEGVALLSVGVT

SWGYSGLDILAKYVFAFLLLRWVAANEGTVSGSGMGIGSGGAAPADD.

SEQ ID NO: 27 is an amino acid sequence of a prolactin signal sequence:
DSKGSSQKGSRLLLLLVVSNLLLCQGVVSTPV.

DETAILED DESCRIPTION

The invention in some aspects relates to the expression in cells of light-driven ion pump polypeptides that can be activated by contact with one or more pulses of light, which results in strong hyperpolarization and silencing of the cell. Light-activated pumps of the invention, also referred to herein as light-activated ion pumps (LAIPs) can be expressed in specific cells, tissues, and/or organisms and used to control cells in vivo, ex vivo, and in vitro in response to pulses of light of a suitable wavelength.

When expressed in a cell (e.g., an excitable or non-excitable cell), a LAIP of the invention can be activated by contacting the cell with a light having a wavelength between about 450 nm and 690 nm (e.g., using a single photon process—multiphoton may be higher). Although activation can occur across the range of wavelengths from 450 nm through 690 nm, the strength of the hyperpolarization in the excitable cell (e.g., the magnitude of the voltage deflection) differs depending on the wavelength of light in the range. Contact with light having a wavelength from about 450 nm to below about 600 nm can hyperpolarize an excitable cell that includes an LAIP of the invention but the strength of the hyperpolarization may be insufficient to silence the cell. The strength of the hyperpolarization can be tuned by contacting a LAIP of the invention with a desired wavelength of light. For example, for a weaker hyperpolarization, a LAIP-containing cell or tissue may be contacted with a light having a wavelength at the lower end of the 450 nm to 690 nm wavelength range. To have a stronger hyperpolarization effect, the cell may be contacted with a light having a longer wavelength light. Thus, the strength of hyperpolarization can be tuned using various wavelengths of light.

Contact with a light in the red spectrum more strongly hyperpolarizes the excitable cell and the hyperpolarization by light in the red spectrum range of wavelengths is sufficient to silence the excitable cell. For example, contact with light in a wavelength range such as between 620 nm and 690 nm, 640 nm and 690 nm, 660 nm and 670 nm, 660 nm and 690 nm, 670 nm and 690 nm, or 680 nm and 690 nm hyperpolarizes the cell at a level sufficient to silence the cell. Exemplary wavelengths of light that may be used to silence a cell expressing a LAIP of the invention, include wavelengths from at least about 620 nm, 625 nm, 630 nm, 635 nm, 640 nm, 645 nm, 650 nm, 655 nm, 660 nm, 665 nm, 670 nm, 675 nm, 680 nm, 685 nm, to about 690 nm, including all wavelengths therebetween. Red-light cell silencing may be obtained in excitable cells in which one or more LAIPs of the invention are expressed.

As used herein, the terms “silence” or “silenced” used in the context of cells means that an excitable cell in which the ability to initiate action potential (also referred to as a spike) is substantially reduced or eliminated in the cell. For example, for initiation of an action potential, a cell at a baseline voltage of about −65 mV receives an input signal that shifts cell’s voltage up by up to approximately 15, 20, 30, or 40 millivolts (mV). When the change in voltage is sufficient to reach the cell’s spike initiation voltage threshold an action potential (e.g. a spike) results. When a cell is hyperpolarized by activating a LAIP of the invention with light, the cell voltage becomes more negative than the baseline level, and an incoming signal may or may not be sufficient to raise the cell’s voltage sufficiently to reach the threshold and trigger an action potential in the cell. Thus, at wavelengths of light at the low end of the 450 nm to 690 nm wavelength range, a cell can be hyperpolarized but may not be silenced. It has been discovered that by contacting a cell expressing a LAIP of the invention with a red light, the cell’s voltage may drop to a level that prevents an input signal from raising the cell voltage to the to the threshold necessary to trigger an action potential, and the cell is silenced.

It will be understood that resting voltages and voltages changes initiated by light contact may differ depending on whether the cell expressing an LAIP of the invention is in vitro, in vivo, and may also on the type of cell and its normal resting voltage. For example, in cells in vivo, there may be feedback mechanisms that can limit the voltage deflection, even though the cell is still silenced. Thus, changes in voltages may be assessed based on differences, not as absolute values, in part because not all excitable cells have the same resting membrane potential. For example, cardiac cells are far more hyperpolarized than cortical neurons, which are more hyperpolarized than Purkinje neurons, which are more hyperpolarized than HEK and CHO cells. One skilled in the art will recognize how to assess voltages changes and cell silencing using standard methods.

In some embodiments, the presence of LAIPs in one, two, three, or more (e.g. a plurality) of cells in a tissue or organism, can result in silencing of the single cell or the plurality of cells by contacting the LAIPs with red light of suitable wavelength. Upon activation with a suitable wavelength for cell silencing, LAIPs of the invention may be up to 90%, 95%, or 100% effective in silencing a cell or plurality of cells in which LAIPs are expressed.

In exemplary implementations, the invention comprises methods for preparing and using genes encoding LAIPs of the invention that have now been identified. The invention, in part, also includes isolated nucleic acids comprising sequences that encode LAIPs of the invention as well as vectors and constructs that comprise such nucleic acid sequences. In some embodiments the invention includes expression of polypeptides encoded by the nucleic acid sequences, in cells, tissues, and organisms. Also included in some aspects of the invention are methods of combinatorial optimization of genes encoding LAIPs through novel gene classes, targeted protein site-directed mutagenesis, and potent protein trafficking sequences. The resultant gene products, when expressed in genetically targeted cells, allow the powerful hyperpolarization of cellular voltage in response to pulses of light. These pumps can be genetically-expressed in specific cells (e.g., using a virus or other vector) and then used to control cells in intact organisms (including humans) as well as in in vitro and ex vivo cells in response to pulses of light.

The magnitude of the current that can be pumped into cells expressing the pumps encoded by sequences of the invention upon exposure to low light powers of long-wavelength visible light is significantly improved from existing pumps (e.g., Halo/NpHR). The ion pumps of the invention have a red-shifted activation spectra that is unique from the activation spectra of other light-activated pumps and channels (e.g. Halo/NpHR, arch, Mac, ChR2, etc.) (see for example, FIG. 1).

It has been identified that LAIPs of the invention are activated and silence cells at different wavelengths than some previously identified light-activated ion pumps. Thus LAIPs of the invention can be used in either alone, using a selective light spectrum for activation and/or cell silencing and can also be used in combination with other light-activated ion pumps that utilize different wavelength of light for activation and/or cell silencing, thus allowing two, three, four, or more different wavelengths of light to be used to hyperpolarize and/or silence different sets of cells in a tissue or organism by expressing pumps with different activation spectra and/or different silencing spectra in different cells and then illuminating the tissue and/or organism with the appropriate wavelengths of light to hyperpolarize and/or silence the cells.

Figure 2:
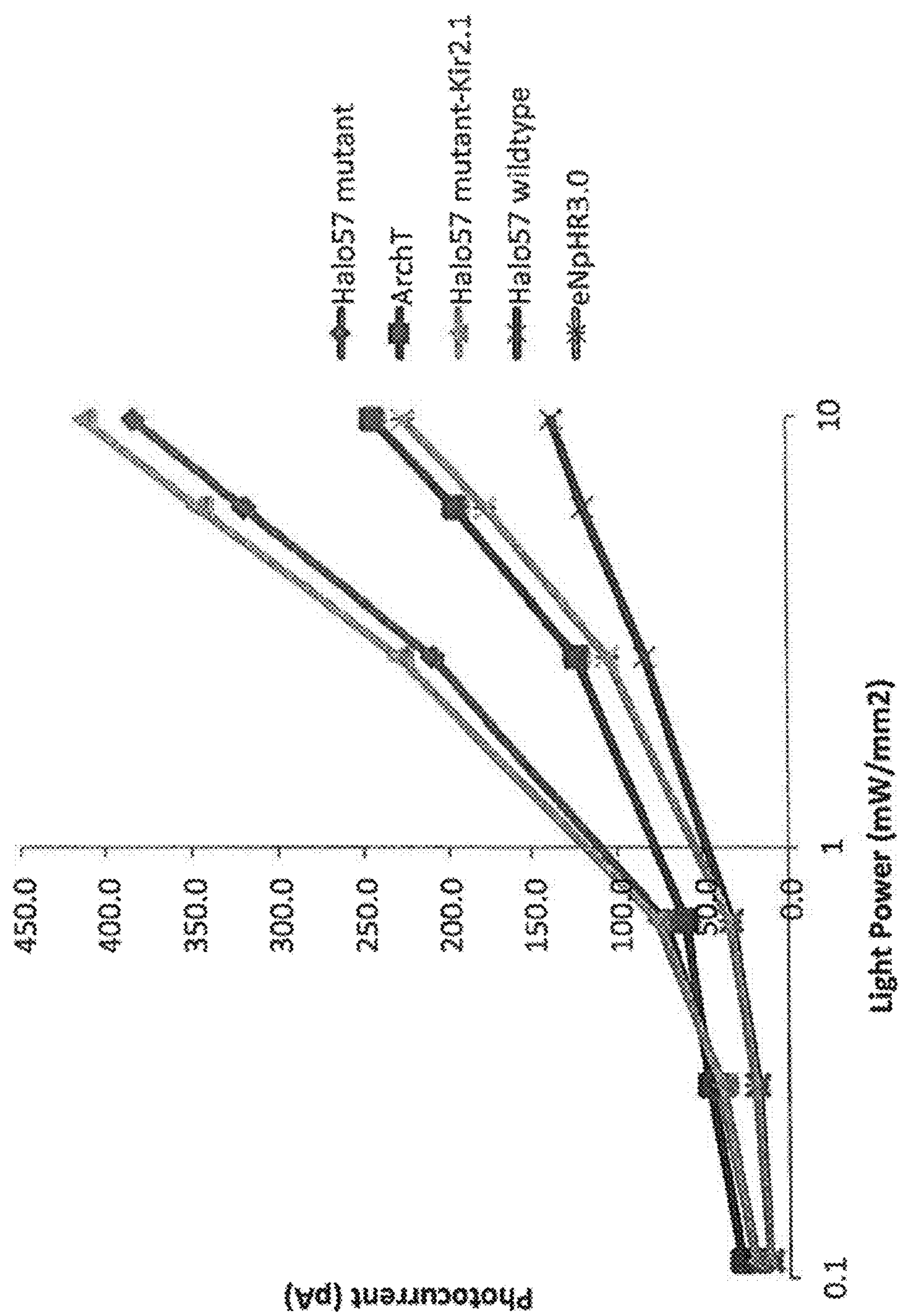
FIG. 2 is a graph of light power versus photocurrent for various LAIPs and other molecules. The figure demonstrates the higher photocurrent achieved by Halo57 mutant and Halo57 mutant-Kir2.1 than others tested.

Use of ion pumps as described herein, permits multiple colors of light to be used to alter the physiology of different sets of cells in the same tissue, by expressing polypeptide ion pumps with different activation spectra genetically in different cells, and then illuminating the cells and/or tissue with different colors of light. Additionally, the low light power requirement allows the silencing of large tissue volumes, and allows long distance optical silencing, which may be used to advantage when targeting organs or tissues that are difficult to surgically access. Additionally, low light power requirement prevents tissue damage from light-caused heating. FIG. 2 shows light power levels of various LAIPs of the invention.

Specific ranges of wavelengths of light useful to activate ion pumps of the invention are provided and described herein. It will be understood that a light of appropriate wavelength for activation and will have a power and intensity appropriate for activation. It is well known in the art that light pulse duration, intensity, and power are parameters that can be altered when activating a pump with light. Thus, one skilled in the art will be able to adjust power, intensity appropriately when using a wavelength taught herein to activate a LAIP of the invention. A benefit of a red-light activated LAIP of the invention, may be the ability to "tune" its response using an appropriate illumination variables (e.g., wavelength, intensity, duration, etc.) to activate the channel. Methods of adjusting illumination variables and assessing voltage changes in cells are well-known in the art and representative methods can be found in publications such as: Chow et al. Nature 2010, Jan. 7; 463(7277):98-102; Han et al. Front Mol Neurosci. 2009; 2:12. Epub 2009 Aug. 27; Tang et al. J Neurosci. 2009 Jul. 8; 29(27):8621-9, each of which is incorporated herein by reference. Thus, it is possible to utilize a narrow range of one or more illumination characteristics to activate a LAIP of the invention. This may be useful to illuminate a LAIP that is co-expressed with one or more other light activated pumps that can be illuminated with a different set of illumination parameters for their activation. Thus, permitting controlled activation of a mixed population of light-activated pumps.

Taxonomy and Sequence Sources

In particular, the present invention includes, in part, the expression and use of a novel class of LAIPs to hyperpolarize excitable cells and can also be expressed and used to alter ion transport into non-excitable cells. In some non-limiting embodiments of the invention one or more newly identified LAIPs may be expressed in cells. Some LAIPs of the invention have amino acid sequences derived from halorhodopsins that are naturally expressed in the genus *Haloarcula* or *halomicrobium*, or other members of the Halobacteriaceae family. *Haloarcula, Halomicrobium*, and other members of the Halobacteriaceae family are extreme halophilic archaeons and are found in saline environment such as saline lakes, salterns, and some soils. Halorhodopsins of the *haloarcula* genus are also known as cruxhalorhodopsins. Some embodiments of the invention include isolated nucleic acid and/or amino acid halorhodopsin sequences, for example, from *haloarcula* or *halomicrobium* or other halobacteriaceae sequences, which may be wild-type or modified sequences, and methods for their use.

Microbial halorhodopsins of the *haloarcula* genus, include, but are not limited to the *Halobacterium salinarum* (strain shark), which is also referred to as *Halobacterium halobium* (strain shark) gene for halorhodopsin, the *Halobacterium salinarum* (strain port), which is also referred to as *Halobacterium halobium* (strain port) gene for halorhodopsin, and the *Haloarcula marismortui* ATCC 43049 gene for halorhodopsin. One skilled in the art will be able to identify additional Halobacteriaceae halorhodopsin sequences with sufficient amino acid sequence homology to halorhodopsin sequences such as Halo57, Gene4, Gene58, set forth herein, to be able to apply methods of the invention using the additional halorhodopsin sequences.

LAIPs of the invention are transmembrane polypeptides that use light energy to move ions and protons into the cell in which they are expressed, thus altering the cell's membrane potential. A non-limiting example of an ion that can be moved into a cell the using a LAIP of the invention is a chloride ion, potassium ion, and/or a sodium ion. LAIPs of the invention can be activated by light, either sustained light or light pulses and can inhibit or eliminate initiation of action potentials in the cells in which they are expressed.

The wild-type and modified Halobacteriaceae halorhodopsin nucleic acid and amino acid sequences used in aspects and methods of the invention are "isolated" sequences. As used herein, the term "isolated" used in reference to a polynucleotide, nucleic acid sequence or polypeptide sequence of a halorhodopsin, it means a polynucleotide, nucleic acid sequence, or polypeptide sequence that is separate from its native environment and present in sufficient quantity to permit its identification or use. Thus, an isolated polynucleotide, nucleic acid sequence, or polypeptide sequence of the invention is a polynucleotide, nucleic acid sequence, or polypeptide sequence that is not part of, or included in its native host. For example, a nucleic acid or polypeptide sequence may be naturally expressed in a cell or organism of a member of the *haloarcula* genus, but when the sequence is not part of or included in a *haloarcula* cell or organism it is considered to be isolated. Similarly, a nucleic acid or polypeptide sequence may be naturally expressed in a cell or organism of a member of the *halomicrobium* genus, but the sequence is not part of or included in a *halomicrobium* cell or organism, it is considered to be isolated. Thus, a nucleic acid or polypeptide sequence of a *haloarcula, halomicrobium*, or other halorhodopsin that is present in a vector, in a heterologous cell, tissue, or organism, etc., is an isolated sequence. The term "heterologous" as used herein, means a cell, tissue or organism that is not the native cell, tissue, or organism. The terms, "protein", "polypeptides", and "peptides" are used interchangeably herein.

LAIP Sequences Including Modified Sequences

A LAIP of the invention may comprise a wild-type polypeptide sequence or may be a modified polypeptide sequence. As used herein the term "modified" or "modification" in reference to a nucleic acid or polypeptide sequence refers to a change of one, two, three, four, five, six, or more amino acids in the sequence as compared to the wild-type sequence from which it was derived. For example, a modified polypeptide sequence may be identical to a wild-type polypeptide sequence except that it has one, two, three, four, five, or more amino acid substitutions, deletions, insertions, or combinations thereof. In some embodiments of the invention a modified sequence may include one, two, three, four, or more amino acid substitutions in a wild-type halorhodopsin sequence.

It will be understood that sequences of LAIPs of the invention may be derived from various members of the *haloarcula* genus, the *halomicrobium*, or from other rhodopsin sequences that correspond, at least in part, to *haloarcula* and *halomicrobium* sequences disclosed herein. For example, SEQ ID NO:2, the wild-type amino acid sequence of the halorhodopsin polypeptide referred to herein as Halo57 is shown in FIG. 3. Amino acid sequences of additional exemplary LAIP polypeptides of the invention are also shown in FIG. 3, which shows sequences aligned with Halo57 and with each other. Using standard sequence alignment methods one of ordinary skill in the art is able to align rhodopsin sequences (including, but not limited to *haloarcula* halorhodopsin, *halomicrobium* halorhodopsin, and other halobacteriaceae halorhodopsin sequences) to determine the correspondence of a residue in one sequence with a residue in an aligned sequence. Thus, as a non-limiting example, one skilled in the art can ascertain that the Ala residue at position 104 in the Gene56 sequence set forth as SEQ ID NO:9; corresponds to the Ala residue at position 88 in the Gene55 sequence set forth as SEQ ID NO:10 and that both correspond to the Ala residue at position 122 in the Halo57 sequence set forth as SEQ ID NO:2.

Routine sequence alignment methods and techniques can be used to align two or more substantially similar rhodopsin sequences, including but not limited to sequences from *haloarcula* rhodopsin, *halomicrobium* halorhodopsin, etc., thus providing a means by which a corresponding location of a modification made in one LAIP sequence can be identified in another rhodopsin sequence. For example, the corresponding position(s) of modifications such as A122D, K200R, W214F in the Halo57 sequence set forth as SEQ ID NO:2 can be identified in aligned sequences. Similarly, the corresponding position(s) of modifications such as A137D, K215R, W229F in the Halo sequence set forth as SEQ ID NO:14 can be identified in aligned sequences. The substituted Halo57 sequence can be aligned with one or more *haloarcula* halorhodopsin sequences or with one or more other rhodopsin sequence that are substantially similar in amino acid sequence to Halo57 as set forth herein, to identify corresponding positions for the substitutions in the aligned sequences. LAIP polypeptides having one or more substitutions or other modifications can be identified and tested for characteristics including, but not limited to: expression, cell localization, activation and silencing in response to contact with light using methods disclosed herein.

A LAIP polypeptide of the invention may include amino acid variants (e.g., polypeptides having a modified sequence) of the naturally occurring wild-type sequences, as set forth herein. Modified LAIP polypeptide sequences may be at least about 75%, 80%, 85%, 90%, 95%, 96%, 97%, 98%, 99%, or 100% homologous to the polypeptide sequence of a LAIP disclosed herein, such as Halo57, Gene4, Gene58, etc. Homology in this context means sequence similarity or identity. Such sequence homology can be determined using standard techniques known in the art. LAIPs of the present invention include the LAIP polypeptide and nucleic acid sequences provided herein and variants that are more than about 50%, 55%, 60%, 65%, 70%, 75%, 80%, 85%, 90%, 95%, 96%, 97%, or 98% homologous to a provided sequence.

LAIPs polypeptide of the invention may be shorter or longer than the LAIP polypeptide sequences set forth herein. Thus, in a preferred embodiment, included within the definition of LAIP polypeptides are full-length polypeptides or functional fragments thereof. In addition, nucleic acids of the invention may be used to obtain additional coding regions, and thus additional protein sequences, using techniques known in the art.

In some aspects of the invention, substantially similar Halobacteriaceae halorhodopsin polypeptide sequences may have at least 80%, 85%, 90%, 91%, 92%, 93%, 94%, 95%, 96%, 97%, 98%, or 99% or 100% similarity to a halorhodopsin sequence disclosed herein, non-limiting examples of which include as Halo57, Gene58, Gene4, and Gene 56, etc. Art-known alignment methods and tools can be used to align substantially similar sequences permitting positional identification of amino acids that may be modified as described herein to prepare a LAIP of the invention.

Sequence modifications can be in one or more of three classes: substitutions, insertions or deletions. These modified sequences, (which may also be referred to as variants) ordinarily are prepared by site specific mutagenesis of nucleic acids in the DNA encoding a LAIP polypeptide, using cassette or PCR mutagenesis or other techniques known in the art, to produce DNA encoding the modified LAIP, and thereafter expressing the DNA in recombinant cell culture. Amino acid sequence variants are characterized by the predetermined nature of the variation, a feature that sets them apart from naturally occurring allelic or interspecies variation of the LAIPs of the invention. Modified LAIPs generally exhibit the same qualitative biological activity as the naturally occurring analogue, although variants can also be selected which have modified characteristics.

A site or region for introducing an amino acid sequence modification may be predetermined, and the mutation per se need not be predetermined. For example, to optimize the performance of a mutation at a given site, random mutagenesis may be conducted at the target codon or region and the expressed modified LAIP screened for the optimal combination of desired activity. Techniques for making substitution mutations at predetermined sites in DNA having a known sequence are well known, for example, M13 primer mutagenesis and PCR mutagenesis.

Amino acid substitutions are typically of single residues; and insertions usually will be on the order of from about 1 to 20 amino acids, although considerably larger insertions may be tolerated. Deletions may range from about 1 to about 20 residues, although in some cases deletions may be much larger.

Substitutions, deletions, insertions or any combination thereof may be used to arrive at a final modified LAIP of the invention. Generally these changes are done on a few amino acids to minimize the alteration of the molecule. However, larger changes may be tolerated in certain circumstances.

Variants of LAIPs set forth herein, may exhibit the same qualitative light-activated ion pump activity as one or more of the sequences set forth herein, such as Halo57, Gene4, Gene57, but may show some altered characteristics such as altered photocurrent, stability, speed, compatibility, and toxicity, or a combination thereof. For example, the polypeptide can be modified such that it has an increased photocurrent and/or has less toxicity than another LAIP polypeptide.

A LAIP polypeptide of the invention can incorporate unnatural amino acids as well as natural amino acids. An unnatural amino acid can be included in a LAIP of the invention to enhance a characteristic such as photocurrent, stability, speed, compatibility, or to lower toxicity, etc.

In some embodiments, the invention includes the use of targeted site-directed mutagenesis at specific amino acid residues of halorhodopsins, including but not limited to residues that correspond to A122D, K200R, and W215F of the amino acid sequence set forth as Halo57 (SEQ ID NO:2). Specific point mutations have been identified that alone, or in combination of two or more have been demonstrated to be particularly effective at altering photocurrent amplitude in LAIPs of the invention. In particular, the A122D, K200R and W214F mutations to cruxhalorhodopsins and additionally, the *Natromonas pharaonis* halorhodopsin, have been found boost effective light sensitivity and photocurrent amplitude to hyperpolarize excitable cells. Substitutions, including but not limited to: K200R, T111S, K200H, K200Q, T203S, [K200Q+W214F], [K200H+W214F], (amino acid numbered in reference to the Halo57 sequence set forth here as SEQ ID NO:2) all were found to substantially boost photocurrent. Thus, mutations that correspond to a K200R substitution, a T111S substitution, a K200H substitution, a K200Q substitution, a T203S substitution, a K200Q+W214F double substitution, or a K200H+W214F double substitution, can be made in Halo57 sequence and/or in a Halobacteriaceae halorhodopsin sequence that is substantially similar to Halo57 to prepare a LAIP of the invention. Substitutions at the K200 position appear to be beneficial and to increase photocurrent required to hyperpolarize cells. Additional substitutions at the K200 position including, but not limited to: K200D and K2005 (number in reference to the Halo57 amino acid sequence provided herein) are also contemplated in embodiments of the invention. Also, substitutions at the W214 position appear to be beneficial and to increase photocurrent required to hyperpolarize cells, including, but not limited to a W214Y substitution, a W214L substitution. Additional substitutions at the W214 position (number in reference to the Halo57 amino acid sequence provided herein) are also contemplated in embodiments of the invention. The amino acid sequence of Halo57 with the double substitution K200R+W214F is set forth as SEQ ID NO:26.

Another aspect of the invention provides nucleic acid sequences that code for a LAIP of the invention. It would be understood by a person of skill in the art that the LAIP polypeptides of the present invention can be coded for by various nucleic acids. Each amino acid in the protein is represented by one or more sets of 3 nucleic acids (codons). Because many amino acids are represented by more than one codon, there is not a unique nucleic acid sequence that codes for a given protein. It is well understood by those of skill in the art how to make a nucleic acid that can code for LAIP polypeptides of the invention by knowing the amino acid sequence of the protein. A nucleic acid sequence that codes for a polypeptide or protein is the "gene" of that polypeptide or protein. A gene can be RNA, DNA, or other nucleic acid than will code for the polypeptide or protein.

It is understood in the art that the codon systems in different organisms can be slightly different, and that therefore where the expression of a given protein from a given organism is desired, the nucleic acid sequence can be modified for expression within that organism. Thus, in some embodiments, a LAIP polypeptide of the invention is encoded by a mammalian-codon-optimized nucleic acid sequence, which may in some embodiments be a human-codon optimized nucleic acid sequence. An aspect of the invention provides a nucleic acid sequence that codes for a LAIP that is optimized for expression with a mammalian cell. A preferred embodiment comprises a nucleic acid sequence optimized for expression in a human cell.

Delivery of LAIPs

Delivery of a LAIP polypeptide to a cell and/or expression of a LAIP in a cell can be done using art-known delivery means.

In some embodiments of the invention a LAIP polypeptide of the invention is included in a fusion protein. It is well known in the art how to prepare and utilize fusion proteins that comprise a polypeptide sequence. In certain embodiments of the invention, a fusion protein can be used to deliver a LAIP to a cell and can also in some embodiments be used to target a LAIP of the invention to specific cells or to specific cells, tissues, or regions in a subject. Targeting and suitable targeting sequences for deliver to a desired cell, tissue or region can be performed using art-known procedures.

It is an aspect of the invention to provide a LAIP polypeptide of the invention that is non-toxic, or substantially non-toxic in cells in which it is expressed. In the absence of light, a LAIP of the invention does not significantly alter cell health or ongoing electrical activity in the cell in which it is expressed.

In some embodiments of the invention, a LAIP of the invention is genetically introduced into a cellular membrane, and reagents and methods are provided for genetically targeted expression of LAIP polypeptides, including Halo57, Gene4, Gene58, etc. Genetic targeting can be used to deliver LAIP polypeptides to specific cell types, to specific cell subtypes, to specific spatial regions within an organism, and to sub-cellular regions within a cell. Genetic targeting also relates to the control of the amount of LAIP polypeptide expressed, and the timing of the expression.

Some embodiments of the invention include a reagent for genetically targeted expression of a LAIP polypeptide, wherein the reagent comprises a vector that contains the gene for the LAIP polypeptide.

As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert LAIP polypeptides into dividing and non-dividing cells and can insert LAIP polypeptides to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein.

In certain embodiments of the invention, a vector may be a *lentivirus* comprising the gene for a LAIP of the invention, such as Halo57, Gene4, Gene58, or a variant thereof. A *lentivirus* is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a LAIP polypeptide in a wide variety of cell types—thus a promoter for a gene that is widely expressed in a variety of cell types, for example a "housekeeping gene" can be used to express a LAIP polypeptide in a variety of cell types. Non-limiting examples of general promoters are provided elsewhere herein and suitable alternative promoters are well known in the art.

In certain embodiments of the invention, a promoter may be an inducible promoter, examples of which include, but are not limited to tetracycline-on or tetracycline-off, or tamoxifen-inducible Cre-ER.

Methods of Use of LAIPs of the Invention

Figure 4A:
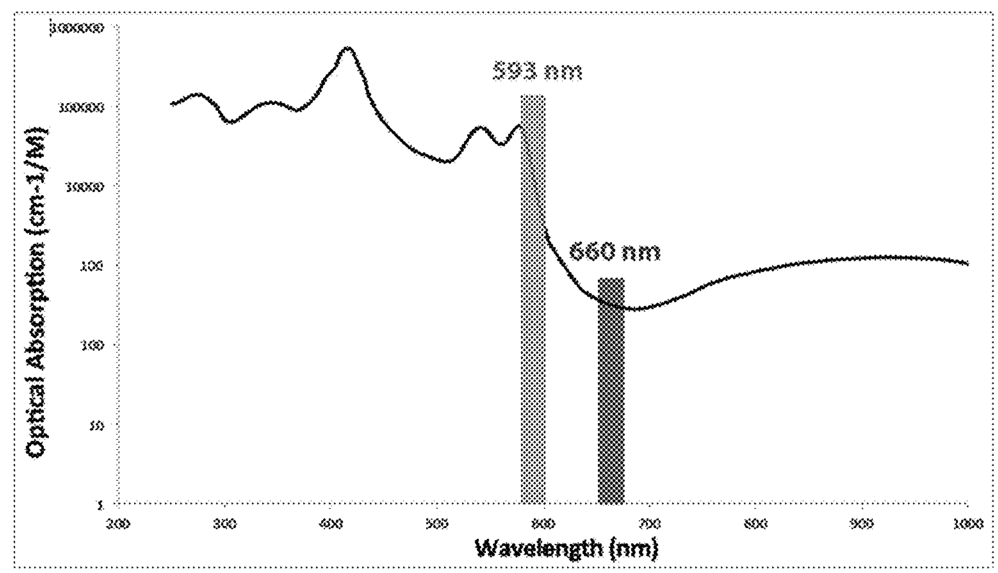
FIG. 4A and FIG. 4B present two graphs of results relating to hemoglobin absorption.
Figure 4B:
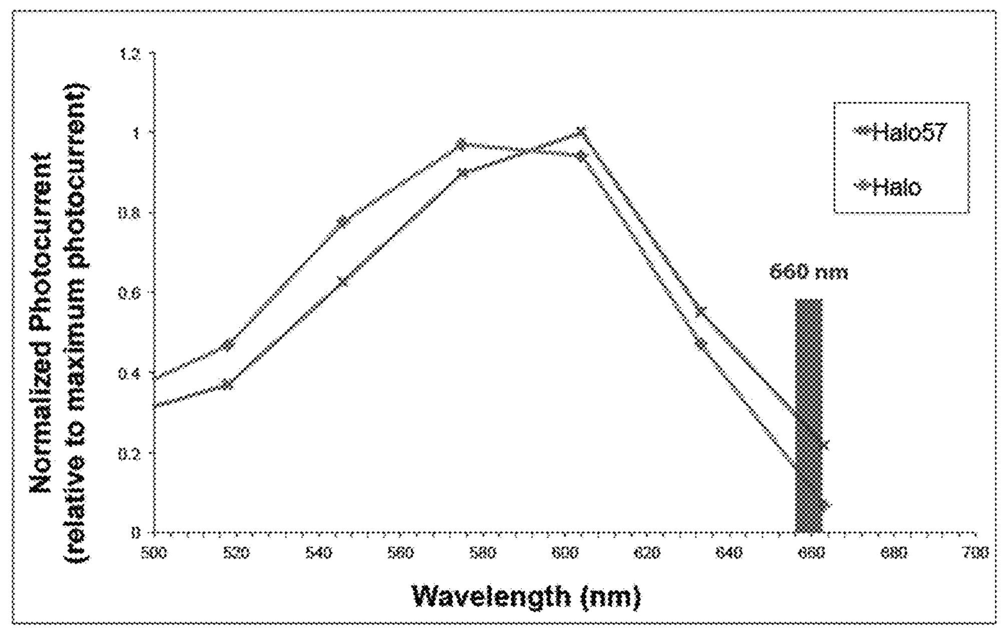

LAIPs of the invention are well suited for targeting hemoglobin-rich tissues, such as the heart, cardiac system, arterial walls, or high capillary density due to the fact that they have unique activation spectra that prevents optical attenuation from oxygenated hemoglobin or pure hemoglobin absorption. FIG. 4A illustrates a trough of hemoglobin absorption and shows results indicating that oxygen-bound hemoglobin absorbs 24 times more light at 593 nm illumination than at 660 nm, near its trough of absorbance. FIG. 4B shows results indicating that Halo57 redshift, which allows illumination at the hemoglobin absorption trough.

Further, their low levels of hyperpolarization and lack of silencing at blue light wavelengths is well suited for optogenetic applications in subjects or patients where blue-light illumination is unavoidable, such as photodynamic "blue-light" therapy for actinic keratosis and acne patients, or the blue light boxes used to induce melatonin production for sufferers of seasonal affective disorder (SAD).

Working operation of a prototype of this invention was demonstrated by genetically expressing light-activated ion pump molecules of the invention in excitable cells, illuminating the cells with suitable wavelengths of light, and demonstrating rapid hyperpolarization of the cells in response to the light, as well as rapid release from hyperpolarization upon cessation of light. Depending on the particular implementation, methods of the invention allow light control of cellular functions in vivo, ex vivo, and in vitro.

In some aspects of the invention, the newly identified light-activated ion pumps are chloride pumps, which can be used to modify the transmembrane potential of cells (and/or their sub-cellular regions, and their local environment). For example, the use of inwardly rectifying chloride pumps will hyperpolarize cells by moving negatively charged chloride ions from the extracellular environment into the cytoplasm, and the red light sensitivity of light-activated ion pumps of the invention, with respect to cell silencing, is highly advantageous due to the low light power requirement, as well as the fact that the pumps can be used in conjunction with other optically sensitive molecules with different action spectra to control multiple cell types with reduced interference from cross-excitation.

In non-limiting examples of methods of the invention, microbial rhodopsins are used in mammalian cells without need for any kind of chemical supplement, and in normal cellular environmental conditions and ionic concentrations. For example, members of the *haloarcula* class, such as the *Halobacterium salinarum* (strain shark)/*Halobacterium halobium* (strain shark) gene for halorhodopsin, the *Halobacterium salinarum* (strain port)/*Halobacterium halobium* (strain port) gene for halorhodopsin, the *Haloarcula marismortui* ATCC 43049 gene for cruxhalorhodopsin, the *Halomicrobium mukohataei* DSM 12286 gene for cruxhalorhodopsin, the *Haloarcula californiae* ATCC 33799 gene for cruxhalorhodopsin, and the *Haloarcula sinaiiiensis* ATCC 33800 gene for cruxhalorhodopsin have been used in exemplary implementations of the invention. The polypeptides encoded by these genes, e.g., in humanized or mouse-optimized form, allow hyperpolarizations significantly larger than what has been discovered before at red-light wavelengths.

Figure 5A:
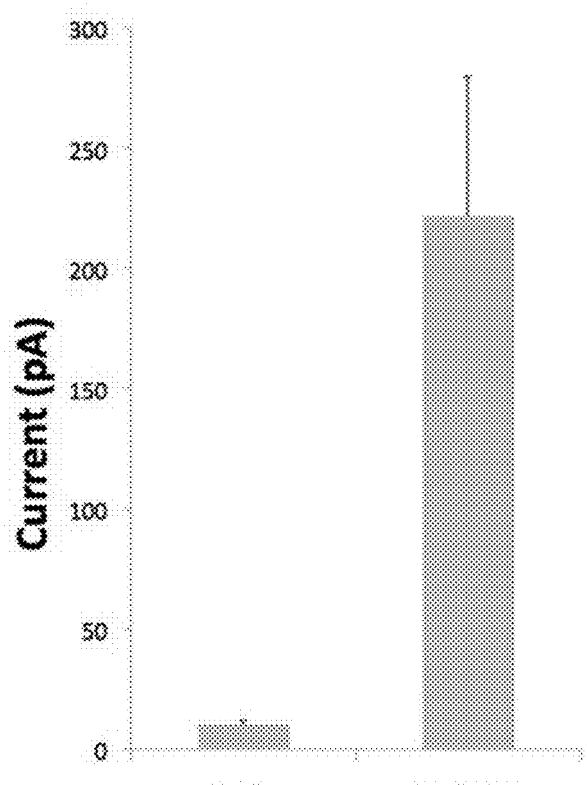
FIG. 5A and FIG. 5B present two histograms showing (photo)current for Halo, Halo57 and single and double mutants of Halo57. Screen data shows outward photocurrents (FIG. 5A) and wildtype-normalized photocurrents (FIG. 5B) for Halo and Halo57 mutants, measured by whole-cell patch-clamp of HEK293FT cells under screening illumination conditions (575±25 nm, 3.7 mW/mm2). Data are mean and s.e. The FIG. 5A histogram illustrates that Halo57 (the *Halobacterium salinarum* (strain shark/*Halobacterium halobium* (strain shark) gene for halorhodopsin) produced orders of magnitude more photocurrent than Halo when illuminated at 660 nm (7 $mW/mm^2$).
Figure 5B:
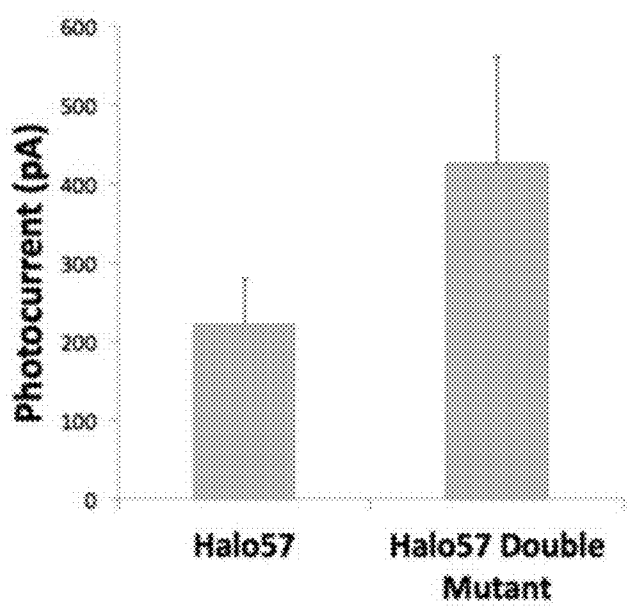

In exemplary implementations of this invention, the *Halobacterium salinarum* (strain shark)/*Halobacterium halobium* (strain shark) gene for halorhodopsin, the *Halobacterium salinarum* (strain port)/*Halobacterium halobium* (strain port) gene for halorhodopsin, and the *Haloarcula marismortui* ATCC 43049 gene for cruxhalorhodopsin have demonstrably improved photocurrent generation at red wavelengths, with significantly lower power requirements. For example, the *Halobacterium salinarum* (strain shark)/*Halobacterium halobium* (strain shark) gene for halorhodopsin (also referred to herein as Halo57) produces 2.9× more photocurrent than the gene product (*N. pharaonis* halorhodopsin, also denoted as "NpHR" or "Halo") at 4 $mW/mm^2$ yellow light illumination and 44× the photocurrent at 7 $mW/mm^2$ red light illumination (see FIG. 5A), respectively (yellow light wavelength=575±25 nm, red light wavelength=660 nm. FIG. 5B shows that photocurrents for Halo57 can be further improved by inclusion of a K200R+W214F double mutation.

As used herein, the term "ion pump" means an integral membrane polypeptide that is capable of moving ions across the membrane of a cell. In general, an ion pump comprises one or more proteins located in a cell membrane. Ion pumps may actively transport ions across the membrane against a concentration gradient using ATP. General functions of ion pumps may include, but are not limited to maintaining osmotic balance in a cell or conducting nerve impulses. Many ion pumps do not express well in a cell and/or their expression may be toxic to the cell and reduce cell health. Thus it was necessary to prepare and screen numerous halorhodopsin light-activated ion pump polypeptides including numerous pumps having one, two, or more specific mutations to identify light-activated ion pumps of the invention that can be expressed in cells without significantly reducing cell health and viability.

Light-activated ion pumps of the invention have been found to be suitable for expression and use in mammalian cells without need for any kind of chemical supplement, and in normal cellular environmental conditions and ionic concentrations. LAIPs of the invention have been found to differ from previously identified pumps in that the LAIPs activate at a wavelengths of light ranging from about 450 nm to about 690 nm, but they also are specifically sensitive to red light and a cell that expresses a LAIP of the invention will be silenced with the LAIP of the invention is contacted with a red light.

Cells and Subjects

A cell used in methods and with sequences of the invention may be an excitable cell or a non-excitable cell. A cell in which a LAIP of the invention may be expressed and may be used in methods of the invention include prokaryotic and eukaryotic cells. Useful cells include but are not limited to mammalian cells. Examples of cells in which a LAIP of the invention may be expressed are excitable cells, which include cells able to produce and respond to electrical signals. Examples of excitable cell types include, but are not limited to neurons, muscles, cardiac cells, and secretory cells (such as pancreatic cells, adrenal medulla cells, pituitary cells, etc.). LAIPs of the invention may also be expressed in non-excitable cells and may function therein, when activated by red light, to alter the ion conductance in the non-excitable cells. For example, an LAIP of the invention may permit chloride transport may across a membrane of a non-excitable cell. LAIPs and methods of the invention may include use of excitable or non-excitable cells in methods of candidate compound assessment, diagnosis, and treatment. Examples of non-excitable cells to which LAIPs of the invention and methods using LAIP of the invention include, but are not limited to cells of the lung, pancreas, liver, intestine, skin, etc.

Non-limiting examples of cells that may be used in methods of the invention include nervous system cells, cardiac cells, circulatory system cells, visual system cells, auditory system cells, hemoglobin-rich cells, secretory cells, endocrine cells, or muscle cells. In some embodiments, a cell used in conjunction with the invention may be a healthy normal cell, which is not known to have a disease, disorder or abnormal condition. In some embodiments, a cell used in conjunction with methods and pumps of the invention may be an abnormal cell, for example, a cell that has been diagnosed as having a disorder, disease, or condition, including, but not limited to a degenerative cell, a neurological disease-bearing cell, a cell model of a disease or condition (e.g., cystic fibrosis, blindness, hearing loss, cardiac disease, etc.), an injured cell, etc. In some embodiments of the invention, a cell may be a control cell.

LAIPs of the invention may be expressed in cells from culture, cells in solution, cells obtained from subjects, and/or cells in a subject (in vivo cells). LAIPs may be expressed and activated in cultured cells, cultured tissues (e.g., brain slice preparations, etc.), and in living subjects, etc. As used herein, a the term "subject" may refer to a human, non-human primate, cow, horse, pig, sheep, goat, dog, cat, rodent, fly or any other vertebrate or invertebrate organism.

Controls and Candidate Compound Testing

LAIPs of the invention and methods using LAIPs of the invention can be utilized to assess changes in cells, tissues, and subjects in which they are expressed. Some embodiments of the invention include use of LAIPs of the invention to identify effects of candidate compounds on cells, tissues, and subjects. Results of testing a LAIP of the invention can be advantageously compared to a control.

As used herein a control may be a predetermined value, which can take a variety of forms. It can be a single cut-off value, such as a median or mean. It can be established based upon comparative groups, such as cells or tissues that include the LAIP and are contacted with light, but are not contacted with the candidate compound and the same type of cells or tissues that under the same testing condition are contacted with the candidate compound. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention.

As a non-limiting example of use of a LAIP to identify a candidate therapeutic agent or compound, a LAIP of the invention may be expressed in an excitable cell in culture or in a subject and the excitable cell may be contacted with a light that activates the LAIP and with a candidate therapeutic compound. In one embodiment, a test cell that includes a LAIP of the invention can be contacted with a light that hyperpolarizes and/or silences the cell and also contacted with a candidate compound. The cell, tissue, and/or subject that include the cell can be monitored for the presence or absence of a change that occurs in the test conditions versus the control conditions. For example, in a cell, a change may be a change in the hyperpolarization or in a hyperpolarization-mediated cell characteristic in the test cell versus a control cell, and a change in hyperpolarization or the hyperpolarization-mediated cell characteristic in the test cell compared to the control may indicate that the candidate compound has an effect on the test cell or tissue that includes the cell. In some embodiments of the invention, a hyperpolarization mediated cell characteristic may be a hyperpolarization-activated conductance, which may, for example, be the result of a T-type calcium channel activity, BK channel activity, or an I_h current. As known in the art, T-type calcium channels are a type of high-voltage calcium channels, BK channels, also referred to as "big potassium" channels are high-conductance potassium channels, and an I_h current is a current that flows through hyperpolarization-activated cyclic-nucleotide gated (HCN) channels. Means of assessing T-type calcium channel activity, BK channel activity, I_h currents, and other hyperpolarization mediated cell characteristics are known in the art. In certain embodiments, a hyperpolarization-mediated-cell characteristic is cell silencing.

Candidate-compound identification methods of the invention that are performed in a subject, may include expressing a LAIP in the subject, contacting the subject with a light under suitable conditions to activate the LAIP and hyperpolarize the cell, and administering to the subject a candidate compound. The subject is then monitored to determine whether any change occurs that differs from a control effect in a subject. Thus, for example, a brain region may be silenced using a LAIP of the invention and a candidate compound may be administered to the brain and the effect of the compound determined by comparing the results with those of a control.

Methods of identifying effects of candidate compounds using LAIPs of the invention may also include additional steps and assays to further characterizing an identified change in the cell, tissue, or subject when the cell is contacted with the candidate compound. In some embodiments, testing in a cell, tissue, or subject can also include one or more cells that has a LAIP of the invention, and that also has one, two, three, or more additional different light-activated ion pumps, wherein at least one, two, three, four, or more of the additional light-activated ion pumps is activated by contact with light having a non-red light wavelength.

In a non-limiting example of a candidate drug identification method of the invention, cells that include a LAIP of the invention are hyperpolarized, thus activating endogenous hyperpolarization-activated conductances (such as T-type calcium channels, BK channels, and I_h currents), and then drugs are applied that modulate the response of the cell to hyperpolarization (determined for example using patch clamping methods or other suitable art-known means). Such methods enable new kinds of drug screening using just light to activate the pumps of interest, and using just light to read out the effects of a drug on the pumps and pump-containing cells of interest.

In some embodiments, LAIP polypeptides of the invention can be used in test systems and assays for assessing membrane protein trafficking and physiological function in heterologously expressed systems and the use of use of light-activated pumps to hyperpolarize a cell that has high intracellular chloride concentrations, such as young adult-born neurons. LAIPs of the invention can also be used test compounds to treat diseases or conditions such as cystic fibrosis, blindness, pain, seizures, degenerative disease, developmental disease, etc.

Methods of Treating

Some aspects of the invention include methods of treating a disorder or condition in a cell, tissue, or subject using LAIPs of the invention. Treatment methods of the invention may include administering to a subject in need of such treatment, a therapeutically effective amount of a LAIP of the invention to treat the disorder. It will be understood that a treatment may be a prophylactic treatment or may be a treatment administered following the diagnosis of a disease or condition. A treatment of the invention may reduce or eliminate a symptom or characteristic of a disorder, disease, or condition or may eliminate the disorder, disease, or condition itself. It will be understood that a treatment of the invention may reduce or eliminate progression of a disease, disorder or condition and may in some instances result in the regression of the disease, disorder, or condition. A treatment need to entirely eliminate the disease, disorder, or condition to be effective.

Administration of a LAIP of the invention may include administration pharmaceutical composition that includes a cell, wherein the cell expresses the light-activated ion pump. Administration of a LAIP of the invention may include administration of a pharmaceutical composition that includes a vector, wherein the vector comprises a nucleic acid sequence encoding the light-activated ion pump and the administration of the vector results in expression of the light-activated ion pump in a cell in the subject.

An effective amount of a LAIP is an amount that increases LAIP in a cell, tissue or subject to a level that is beneficial for the subject. An effective amount may also be determined by assessing physiological effects of administration on a cell or subject, such as a decrease in symptoms following administration. Other assays will be known to one of ordinary skill in the art and can be employed for measuring the level of the response to a treatment. The amount of a treatment may be varied for example by increasing or decreasing the amount of the LAIP administered, by changing the therapeutic composition in which the LAIP is administered, by changing the route of administration, by changing the dosage timing and so on. The effective amount will vary with the particular condition being treated, the age and physical condition of the subject being treated; the severity of the condition, the duration of the treatment, the nature of the concurrent therapy (if any), the specific route of administration, and the like factors within the knowledge and expertise of the health practitioner. For example, an effective amount may depend upon the location and number of cells in the subject in which the LAIP is to be expressed. An effective amount may also depend on the location of the tissue to be treated.

Effective amounts will also depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of a composition to increase the level of a LAIP (alone or in combination with other therapeutic agents) be used, that is, the highest safe dose according to sound medical judgment. It will be understood by those of ordinary skill in the art, however, that a patient may insist upon a lower dose or tolerable dose for medical reasons, psychological reasons or for virtually any other reasons.

A LAIP of the invention may be administered using art-known methods. The manner and dosage administered may be adjusted by the individual physician or veterinarian, particularly in the event of any complication. The absolute amount administered will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compositions that deliver LAIPs of the invention may be administered alone, in combination with each other, and/or in combination with other drug therapies, or other treatment regimens that are administered to subjects. A pharmaceutical composition used in the foregoing methods preferably contain an effective amount of a therapeutic compound that will increase the level of a LAIP polypeptide to a level that produces the desired response in a unit of weight or volume suitable for administration to a subject.

The dose of a pharmaceutical composition that is administered to a subject to increase the level of LAIP in cells of the subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The amount and timing of activation of a LAIP of the invention (e.g., light wavelength, length of light contact, etc.) that has been administered to a subject can also be adjusted based on efficacy of the treatment in a particular subject. Parameters for illumination and activation of LAIPs that have been administered to a subject can be determined using art-known methods and without requiring undue experimentation.

Various modes of administration will be known to one of ordinary skill in the art that can be used to effectively deliver a pharmaceutical composition to increase the level of LAIP in a desired cell, tissue or body region of a subject. Methods for administering such a composition or other pharmaceutical compound of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., Remington's Pharmaceutical Sciences, 18th edition, 1990) provide modes of administration and formulations for delivery of various pharmaceutical preparations and formulations in pharmaceutical carriers. Other protocols which are useful for the administration of a therapeutic compound of the invention will be known to one of ordinary skill in the art, in which the dose amount, schedule of administration, sites of administration, mode of administration (e.g., intra-organ) and the like vary from those presented herein.

Administration of a cell or vector to increase LAIP levels in a mammal other than a human; and administration and use of LAIPs of the invention, e.g. for testing purposes or veterinary therapeutic purposes, is carried out under substantially the same conditions as described above. It will be understood by one of ordinary skill in the art that this invention is applicable to both human and animals. Thus this invention is intended to be used in husbandry and veterinary medicine as well as in human therapeutics.

In some aspects of the invention, methods of treatment using a LAIP of the invention are applied to cells including but not limited to a nervous system cell, a neuron, a cardiac cell, a circulatory system cell, a visual system cell, an auditory system cell, a hemoglobin-rich cell, a muscle cell, or an endocrine cell. Disorders and conditions that may be treated using methods of the invention include, injury, brain damage, degenerative neurological conditions, and may include treatment of diseases and conditions such as Parkinson's disease, Alzheimer's disease, seizure, vision loss, (e.g., retinitis pigmentosa, etc.), hearing loss, cystic fibrosis, pain, etc. Methods of treatment that utilize light activated pumps and channels are known in the art. See, for example. Busskamp, V. et al., *Science*. 2010 Jul. 23; 329(5990):413-7. Epub 2010 Jun. 24, incorporated herein by reference.

Disorders, Diseases, and Conditions

In some aspects of the invention, hemoglobin rich cell types and tissues are targeted using LAIPs of the invention. These comprise the heart, liver, erythrocytes, kidneys, blood vessel walls, or other tissue types with a high surrounding concentration of arteries, veins, or capillaries. Such targeting may be used to advantage for medical treatments, since a high concentration of blood vessels often renders these regions difficult to surgically access. Additionally, the optogenetic control of cardiac and circulatory tissues may be used as a non-pharmacological alternative for the optical control of blood pressure through the vasodilation and vasoconstriction of arteries and veins.

In certain embodiments, methods and LAIPs of the invention may be used to silence large tissue volumes or whole-brain optical silencing as an alternative to methods such as deep brain stimulation (DBS). In some embodiments, methods and LAIPs of the invention may be used to target tissues which are physically difficult to non-destructively access, such as regions of the brain.

In some embodiments, methods and LAIPs of the invention may be used for the long-term treatment for neural disorders with overactive neural behavior, such as epilepsy or muscular spasticity. The low light power requirement means it is well-suited for repeated, long term use since the cumulative effect of surrounding tissue illumination and irradiance would be dramatically lessened.

In some embodiments methods and LAIPs of the invention may be used for neural silencing, as an alternative for blue-light sensitive opsins such as Mac and Halo, where blue-light illumination might cause undesirable opsin behavior. This alternative is particularly advantageous for patients who undergo blue light illumination for another condition, such as the photodynamic "blue-light" therapy used to treat acne and actinic keratosis, or the blue light boxes which are used to address seasonal affective disorder (SAD).

In some embodiments, methods and LAIPs of the invention may be used for the treatment of inner ear hearing or balance disorders. Its low light power requirement for optical stimulation is of great use for cochlear implant alternatives, since stray heat from light irradiance will cause hair cells to fire. Additionally, current cochlear implants are problematic due to the fact that the operation required to access the cochlear hair cells is physically destructive and destroys the patient's residual hearing. The large tissue volume silencing properties which the LAIPs possess allow a minimally invasive stimulation of the hair cells, and reduce the destruction of auditory tissue.

In some embodiments, methods and LAIPs of the invention may be used for the treatment of visual system disorders, for example to treat vision reduction or loss. A LAIP of the invention may be administered to a subject who has a vision reduction or loss and the expressed LAIPs can function as light-sensitive cells in the visual system, thereby permitting a gain of visual function in the subject.

Exemplary treatment methods of the invention may also include use of LAIPs for deep brain silencers or deep brain inhibitors (hereby termed DBSi or DBI, respectively) in the mammalian brain. Deep brain silencing may be used in conjunction with deep brain stimulation, for example, to limit adverse side effects created by electrical stimulation that affects all cell types.

LAIPs of the invention are useful in methods, including, but not limited to prosthetic applications such as gene therapy+device applications in which excitable cells (heart cells, neuron, muscle cells, endocrine cells, etc.) can be silenced, in order to produce long-term cell silencing for neural prosthetics and treatments of disease, which are well suited for the treatment of epilepsy, Parkinson's, neuromuscular conditions and other disorders; drug screening applications including, but not limited to, hyperpolarizing cells, thus activating endogenous hyperpolarization-activated conductances (such as T-type calcium channels, BK channels, and I_h currents), and then applying drugs that modulate the response of the cell to hyperpolarization (using a calcium or voltage-sensitive dye); diagnostics applications, such as, but not limited to, sensitizing samples of tissues from patients to light, or converting them into other cell types (e.g., stem cells) and then sensitizing those to light; and the collection of optical energy, e.g. solar energy, using light-activated pumps expressed in cell lines.

The present invention in some aspects, includes preparing nucleic acid sequences and polynucleotide sequences; expressing in excitable cells polypeptides encoded by the prepared nucleic acid and polynucleotide sequences; illuminating the cells with suitable light, and demonstrating rapid hyperpolarization of the cells in response to light, as well as rapid release from hyperpolarization upon cessation of light. The ability to controllably alter hyperpolarization with light has been demonstrated. The present invention enables light-control of cellular functions in vivo, ex vivo, and in vitro, and the red-light activated ion pumps of the invention and their use, have broad-ranging applications for drug screening, treatments, and research applications, some of which are describe herein.

In some instantiations of this invention, sensitizing chromophores (such as chlorophyll or salinixanthin) are used to broaden or shift the absorbance spectrum of the molecule, and are particularly advantageous for multi-color silencing, tuning the absorbance for optimality with specific optical apparatus (e.g. narrow excitation LEDs and lasers, long wavelength absorption for better transmission through tissue, etc.), or the creation of harmful UV oxidized species.

This invention may be used to advantage to enhance the functional performance of the heterologously expressed ion pumps in mammalian cells via site-directed mutagenesis, such as the A122D single mutation of Halo and the K200R+W214F double mutant of the *Halobacterium salinarum* (strain shark)/*Halobacterium halobium* (strain shark) gene for halorhodopsin.

In illustrative implementations of this invention, the ability to optically perturb, modify, or control cellular function offers many advantages over physical manipulation mechanisms. These advantages comprise speed, non-invasiveness, and the ability to easily span vast spatial scales from the nanoscale to macroscale.

The reagents use in the present invention (and the class of molecules that they represent), allow, at least: significantly larger currents than any previous reagent under red-light illumination; different spectra from older molecules (opening up multi-color control of cells); and greater light sensitivity and tissue penetration depth for optical silencing, making it possible to silence much larger tissue volumes, or silence a target region at a significantly greater distance from the optical stimulus.

EXAMPLES

Example 1

Studies were performed to prepare sequences and to express light-activated ion pumps in cells, tissues, and subjects. Non-limiting exemplary methods are set forth below. Art-known methods that may be applied to light-activated pump molecules and for their use are disclosed in publications such as US Published Application No. 2010/0234273, US Published Application No. 2011/0165681, Chow B Y, et. al. *Methods Enzymol.* 2011; 497:425-43; Chow, B Y, et al. *Nature* 2010 Jan. 7; 463(7277):98-102, the content of each of which is incorporated by reference herein.

Plasmid Construction and Site Directed Mutagenesis.

Opsins were mammalian codon-optimized, and synthesized by Genscript (Genscript Corp., NJ). Opsins were fused in frame, without stop codons, ahead of GFP (using BamHI and AgeI) in a lentiviral vector containing the CaMKII promoter, enabling direct neuron transfection, HEK cell transfection (expression in HEK cells is enabled by a ubiquitous promoter upstream of the lentiviral cassette), and *lentivirus* production and transfection.

Amino acid sequences of various opsins are shown in FIG. 3.

The 'ss' signal sequence from truncated MHC class I antigen corresponded to amino acid sequence (M)VPCTLLLLLAAALAPTQTRA (SEQ ID NO:16), DNA sequence gtcccgtgcacgctgctcctgctgttggcagccgccctggctccgactcagacgcgggcc (SEQ ID NO:15). The 'Prl' Prolactin signal sequence corresponded to amino acid sequence MDSKGSSQKGSRLLLLLVVSNLLLCQVVS (SEQ ID NO:18), or may be the amino acid sequence DSKGSSQKGSRLLLLLVVSNLLLCQGVVSTPV (SEQ ID NO:27); DNA sequence gacagcaaaggttcgtcgcagaaagggtcccgcctgctcctgctgctggtggtgtcaaatctactcttgtgccagggtgtggtctccac ccccgtc (SEQ ID NO:17). The 'ER2' ER export sequence corresponded to amino acid sequence FCYENEV (SEQ ID NO:20), DNA sequence ttctgctacgagaatgaagtg (SEQ ID NO:19). The "KGC-ER2" sequence corresponded to amino acid sequence KSRITSEGEYIPLDQIDINV and FCYENEV (SEQ ID NO:22 and SEQ ID NO:20, respectively); DNA sequences set forth as SEQ ID NO:21 and SEQ ID NO:19, respectively).

Halo point mutants A137D, K215R, W229F, A137D+K215R, A137D+W229F, K215R+W229F, A137D+K215R+W229F,) numbered in reference to the Halo sequence set forth herein as SEQ ID NO:14), for HEK cell testing were generated using the QuikChange kit (Stratagene) on the Halo-GFP fusion gene, corresponding to amino acid sequence set forth herein as SEQ ID NO: 24 or SEQ ID NO:25 and having DNA sequence set forth herein as SEQ ID NO:23 inserted between BamHI and EcoRI sites in the pcDNA3.1 backbone [Invitrogen, (Life Technologies Corporation, Carlsbad, Calif.)]. All other point mutants for HEK cell testing were generated using the QuikChange kit [Stratagene, (Agilent Technologies, Santa Clara, Calif.)] on the opsin-GFP fusion gene inserted between BamHI and AgeI sites in a modified version of the pEGFP-N3 backbone [Invitrogen, (Life Technologies Corporation, Carlsbad, Calif.)]. All constructs were verified by sequencing. Note that mutations in the corresponding positions in the Halo57 sequence set forth herein as SEQ ID NO:2 are as follows: A122D; K200R; W214F, A122D+K200R; A122D+W214F; K200R+W214F; A122D+K200R+W214F, and such mutants were prepared and tested, in Halo57 and in other sequences set forth herein, such as for example, Gene4, Gene55, Gene56, etc., at their corresponding amino acid positions.

Neuron Culture, Transfection, Infection, and Imaging

All procedures involving animals were in accordance with the National Institutes of Health Guide for the care and use of laboratory animals and approved by the Massachusetts Institute of Technology Animal Care and Use Committee. Swiss Webster or C57 mice (Taconic, Hudson, N.Y. or The Jackson Laboratory, Bar Harbor, Mass.) were used. For hippocampal cultures, hippocampal regions of postnatal day 0 or day 1 mice were isolated and digested with trypsin (1 mg/ml) for ~12 min, and then treated with Hanks solution supplemented with 10-20% fetal bovine serum and trypsin inhibitor (Sigma-Aldrich, St. Louis, Mo.). Tissue was then mechanically dissociated with Pasteur pipettes, and centrifuged at 1000 rpm at 4° C. for 10 min. Dissociated neurons were plated at a density of approximately four hippocampi per 20 glass coverslips, coated with Matrigel (BD Biosciences, Sparks, Md.). For cortical cultures, dissociated mouse cortical neurons (postnatal day 0 or 1) were prepared as previously described, and plated at a density of 100-200 k per glass coverslip coated with Matrigel (BD Biosciences, Sparks, Md.). Cultures were maintained in Neurobasal Medium supplemented with B27 [Invitrogen, (Life Technologies Corporation, Carlsbad, Calif.)] and glutamine. Hippocampal and cortical cultures were used interchangeably; no differences in reagent performance were noted.

Neurons were transfected at 3-5 days in vitro using calcium phosphate [Invitrogen, (Life Technologies Corporation, Carlsbad, Calif.)]. GFP fluorescence was used to identify successfully transfected neurons. Alternatively, neurons were infected with 0.1-3 μl of *lentivirus* or adeno-associated virus (AAV) per well at 3-5 days in vitro.

HEK 293FT Cell Culture and Transfection

HEK 293FT cells [Invitrogen, (Life Technologies Corporation, Carlsbad, Calif.)] were maintained between 10-70% confluence in D10 medium (Cellgro, Manassas, Va.) supplemented with 10% fetal bovine serum [Invitrogen, (Life Technologies Corporation, Carlsbad, Calif.)], 1% penicillin/streptomycin (Cellgro, Manassas, Va.), and 1% sodium pyruvate (Biowhittaker, Walkersville, Md.)). For recording, cells were plated at 5-20% confluence on glass coverslips coated with Matrigel (BD Biosciences, Sparks, Md.). Adherent cells were transfected approximately 24 hours post-plating either with TransLT 293 lipofectamine transfection kits (Minis, Madison, Wis.) or with calcium phosphate transfection kits [Invitrogen, (Life Technologies Corporation, Carlsbad, Calif.)], and recorded via whole-cell patch clamp between 36-72 hours post-transfection.

*Lentivirus* Preparation

HEK293FT cells [Invitrogen, (Life Technologies Corporation, Carlsbad, Calif.)] were transfected with the lentiviral plasmid, the viral helper plasmid pΔ8.74, and the pseudotyping plasmid pMD2.G. The supernatant of transfected HEK cells containing virus was then collected 48 hours after transfection, purified, and then pelleted through ultracentrifugation. *Lentivirus* pellet was resuspended in phosphate buffered saline (PBS) and stored at −80° C. until further usage in vitro or in vivo. The estimated final titer is approximately $10^9$ infectious units/mL.

Virus Injection in the Adult Mouse.

All procedures were in accordance with the National Institutes of Health Guide for the Care and Use of Laboratory Animals and approved by the Massachusetts Institute of Technology Committee on Animal Care or the Boston University Institutional Animal Care and Use Committee. Under isoflurane anesthesia, *lentivirus* or adeno-associated virus (AAV) was injected through a craniotomy made in the mouse skull, into the motor cortex (1.75 mm anterior, 1.5 mm lateral, and 1.75 mm deep, relative to bregma. Custom-fabricated plastic headplates were affixed to the skull, and the craniotomy was protected with agar and dental acrylic.

In Vitro Whole Cell Patch Clamp Recording & Optical Stimulation

Whole cell patch clamp recordings were made using a Multiclamp 700B amplifier, a Digidata 1440 digitizer, and a PC running pClamp (Molecular Devices, Sunnyvale, Calif.). Neurons were bathed in room temperature Tyrode containing 125 mM NaCl, 2 mM KCl, 3 mM $CaCl_2$, 1 mM $MgCl_2$, 10 mM HEPES, 30 mM glucose, 0.01 mM NBQX and 0.01 mM GABAzine. The Tyrode pH was adjusted to 7.3 with NaOH and the osmolarity was adjusted to 300 mOsm with sucrose. HEK cells were bathed in a Tyrode bath solution identical to that for neurons, but lacking GABAzine and NBQX. Borosilicate glass pipettes (Warner Instruments, Hamden, Conn.) with an outer diameter of 1.2 mm and a wall thickness of 0.255 mm were pulled to a resistance of 3-9 MΩ with a P-97 Flaming/Brown micropipette puller (Sutter Instruments, Novato, Calif.) and filled with a solution containing 125 mM K-gluconate, 8 mM NaCl, 0.1 mM $CaCl_2$, 0.6 mM MgCl2, 1 mM EGTA, 10 mM HEPES, 4 mM Mg-ATP, and 0.4 mM Na-GTP. The pipette solution pH was adjusted to 7.3 with KOH and the osmolarity was adjusted to 298 mOsm with sucrose. Access resistance was 5-30 MΩ, monitored throughout the voltage-clamp recording. Resting membrane potential was ~−60 mV for neurons and ~−30 mV for HEK 293FT cells in current-clamp recording.

Photocurrents were measured with 500 ms light pulses in neurons voltage-clamped at −60 mV, and in HEK 293FT cells voltage-clamped at −30 mV. Light-induced membrane hyperpolarizations were measured with 500 ms light pulses in cells current-clamped at their resting membrane potential. Light pulses for all wavelengths except 660 nm and action spectrum characterization experiments were delivered with a DG-4 optical switch with 300 W xenon lamp (Sutter Instruments, Novato, Calif.), controlled via TTL pulses generated through a Digidata signal generator. Green light was delivered with a 575±25 nm bandpass filter (Chroma, Bellows Falls, Vt.) and a 575±7.5 nm bandpass filter (Chroma, Bellows Falls, Vt.). Action spectra were taken with a Till Photonics Polychrome V, 150 W Xenon lamp, 15 nm monochromator bandwidth.

Data was analyzed using Clampfit (Molecular Devices, Sunnyvale, Calif.) and MATLAB (Mathworks, Inc., Natick, Mass.).

In Vivo Rodent Electrophysiology, Optical Stimulation, and Data Analysis.

Recordings were made in the cortex of headfixed awake mice after virus injection, using glass microelectrodes of 5-20 MΩ impedance filled with PBS, containing silver/silver-chloride wire electrodes. Signals were amplified with a Multiclamp 700B amplifier and digitized with a Digidata 1440, using pClamp software (Molecular Devices, Sunnyvale, Calif.). A 100 mW red laser (SDL-593-050T, Shanghai Dream Laser (Shanghai Dream Lasers Technology Co, Ltd, ShangHai, China) was coupled to a 200 micron-diameter optical fiber. The laser was controlled via TTL pulses generated through Digidata. Laser light power was measured with an 818-SL photodetector (Newport Corporation, Irvine, Calif.). An optical fiber was attached to the recording glass electrode, with the tip of the fiber ~600 μm laterally away from and ~500 μm above the tip of the electrode (e.g., ~800 microns from the tip), and guided into the brain with a Sutter manipulator at a slow rate of ~1.5 μm/s to minimize deformation of the cortical surface.

Data was analyzed using MATLAB (Mathworks, Inc., Natick, Mass.). Spikes were detected and sorted offline using Wave_clus see: vis.caltech.edu/~rodri/Wave_clus/Wave_clus home). Neurons suppressed during light were identified by performing a paired t-test, for each neuron, between the baseline firing rate during the 5 second period before light onset vs. during the period of 5 second light illumination, across all trials for that neuron, thresholding at the $p<0.05$ significance level. Instantaneous firing rate histograms were computed by averaging the instantaneous firing rate for each neuron, across all trials, with a histogram time bin of 20 ms duration. To determine the latency between light onset and the neural response, a 20 ms-long sliding window was swept through the electrophysiology data and the earliest 20 ms period that deviated from baseline firing rate was looked for, as assessed by performing a paired t-test for the firing rate during each window vs. during the baseline period, across all trials for each neuron. Latency was defined as the time from light onset to the time at which firing rate was significantly different from baseline for the following 120 ms. The time for after-light suppression to recover back to baseline was calculated similarly.

Opsin-fluorophore cassettes were cloned into an AAV backbone using restriction sites BamHI/EcoRI or AAV-FLEX backbone using KpnI/BsrGI sites. The plasmids were amplified and sent to the University of North Carolina Chapel Hill Virus Core facility for viral production.

Example 2

Mutation Preparation and Functional Assessment

Methods

Using methods set forth in Example 1, a K→R substitution was made at the position corresponding to amino acid 200 of Halo57 (SEQ ID NO:2) and the substituted sequence expressed and tested in a cell.

Using methods set forth in Example 1, a W→F substitution was made at the position corresponding to amino acid 214 of Halo57 (SEQ ID NO:2) and the substituted sequence expressed and tested in a cell.

Using methods set forth in Example 1, a double mutant that included a K→R substitution and a W→F substitution made at the positions corresponding to amino acid 200 and 214, respectively, of Halo57 (SEQ ID NO:2) was made and the substituted sequence expressed in a cell and photocurrent measured.

Using methods set forth in Example 1, mutations were made in the sequence of the *Natromonas pharaonis* halorhodopsin (also referred to herein as Halo). Mutations included a single substitution K215R, a single substitution W229F, and double substitution of [K215R+W229F]. The substituted sequences were expressed in cells and the photocurrent measured. Photocurrent was used as a measure of the ion currents in a cell when illuminated by light in voltage-clamp mode. Because a cell's hyperpolarization is induced by the light-activated ion influx, photocurrent is directly correlated to the degree of cell polarization.

Results

Figure 6A:
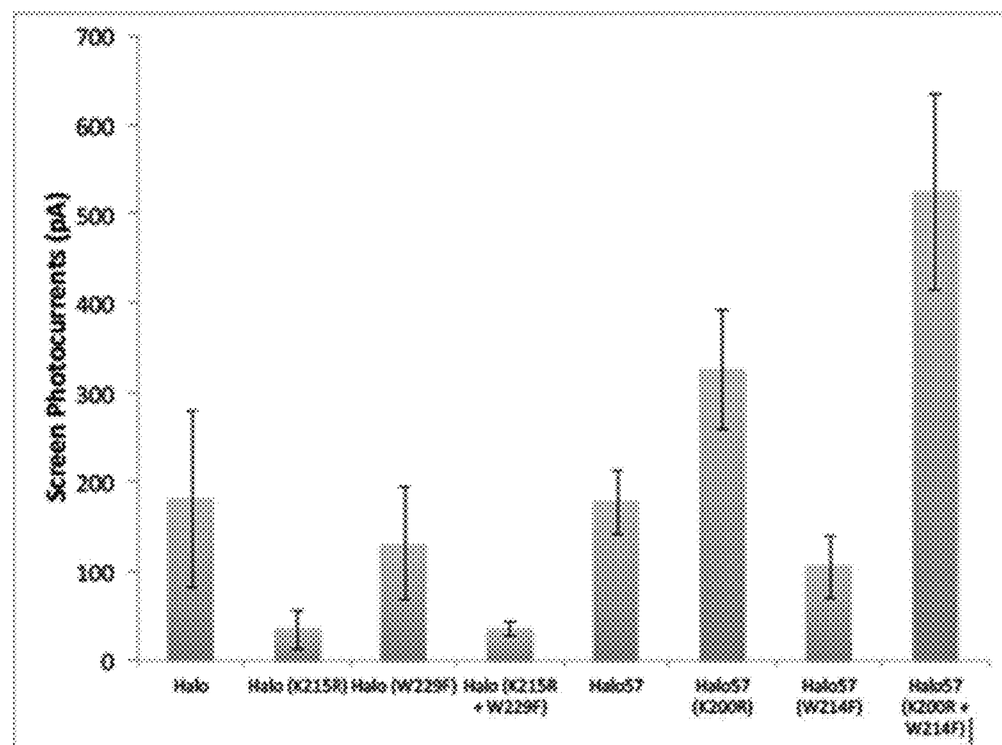
FIG. 6A and FIG. 6B include two histograms showing Halo versus Halo57 photocurrent comparisons.

Results, shown in FIG. 6A, showed that the photocurrent of the Halo57 mutant that included the single substitution K200R was increased as compared to the photocurrent of the wild-type Halo57 LAIP. The photocurrent of the mutant that included the single substitution W214F showed a decrease in the photocurrent compared to the wild-type Halo57 LAIP. The double substitution of K200R+W214F resulted in a synergistic effect on the photocurrent, with the resulting photocurrent significantly greater than either the wild-type Halo57 LAIP or either of the single substitutions.

Figure 6B:
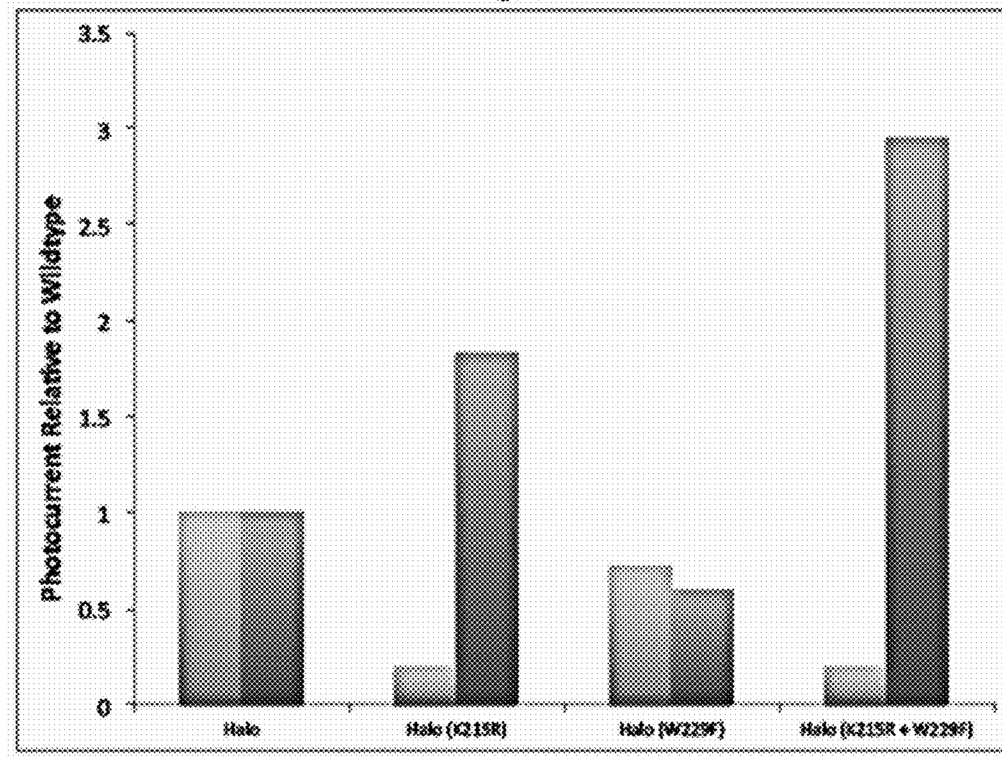

Results of the experiments, shown in FIG. 6B, showed results comparing the effects of mutations on Halo versus Halo57. For each pair of bars, the bar on the left is Halo and the bar on the right is Halo57. The mutation number below the bars represents the mutation positions relative to the Halo sequence. The corresponding amino acid residues in the Halo57 sequence (SEQ ID NO:2) are Halo57 K200R substitution corresponds to Halo K215R substitution and the Halo57 W214F substitution corresponds to Halo W229F substitution.

The results showed that inclusion of the Halo57 K200R and Halo K215R substitution increased photocurrent significantly more in Halo57 than in Halo. The Halo57 W214F and Halo W229F substitution both reduced the photocurrent compared to the Halo57 and Halo wild-type photocurrent, respectively. The Halo57 K200R+W214F and Halo K215R+W229F had very different effects. In Halo57, the K200R+W214F double substitution resulted in a synergistic effect boosting the photocurrent significantly over the wild-type level or that of either single substitution. In contrast, in Halo, the K215R+W229F double substitution resulted in a very low photocurrent, which was significantly lower than even the Halo wild-type photocurrent level. In FIG. 6B, the first bar of each pair is Halo, and the second bar is Halo57. All of the values were normalized relative to the wild-type (mutant/wildtype). The experiment demonstrated the significantly different impact of the substitutions on Halo and Halo57 photocurrents. The left-most pair of bars shows Halo (left) and Halo57 (right) wild-type normalized to themselves (i.e., 1). The second pair of bars from left show that K215R dropped Halo photocurrents but the corresponding substitution in Halo57 (K200R) boosted Halo57 by approximately 70%. The third pair of bars from left show that W229F (equivalent=W214F in Halo57) lowered both Halo and Halo57, and finally the far right pair of bars shows that the double mutation significantly lowered Halo photocurrent and substantially boosted Halo57 photocurrent.

Example 3

Methods

Trafficking of LAIP sequences was examined using various signal and export sequences. Using methods set forth in Example 1, various signal and export sequences were included in vectors along with the LAIP sequence of Halo57 with a K200R+W214F double substitution. Included were the following single sequences or combined sequences:

"ss", having a nucleic acid sequence set forth herein as SEQ ID NO:15 encoding the amino acid sequence set forth herein as SEQ ID NO:16.

"ER2", having a nucleic acid sequence set forth herein as SEQ ID NO:19 encoding the amino acid sequence set forth herein as SEQ ID NO:20.

"ss-prl", having the nucleic acid sequences set forth herein as SEQ ID NO:15 and SEQ ID NO:17 encoding the amino acid sequence set forth herein as SEQ ID NO:16 and SEQ ID NO:18.

"ss-ER2", having the nucleic acid sequences set forth herein as SEQ ID NO:15 and SEQ ID NO:19 encoding the amino acid sequence set forth herein as SEQ ID NO:16 and SEQ ID NO:20.

"Prl-ER2", having the nucleic acid sequences set forth herein as SEQ ID NO:17 and SEQ ID NO:19 encoding the amino acid sequence set forth herein as SEQ ID NO:18 and SEQ ID NO:20.

"ss-prl-ER2, including the nucleic acid sequences set forth herein as SEQ ID NO:15, SEQ ID NO:17, and SEQ ID NO:19, encoding the amino acid sequence set forth herein as SEQ ID NO:16, SEQ ID NO:18, and SEQ ID NO:20.

"Kir2.1 (KGC-ER2), having the nucleic acid sequences set forth herein as SEQ ID NO:21 and SEQ ID NO:19 encoding the amino acid sequence set forth herein as SEQ ID NO:22 and SEQ ID NO:20.

A control LAIP having no trafficking or export sequences was also tested. The photocurrent was determined for each of the above LAIP constructs.

Results

Figure 7:
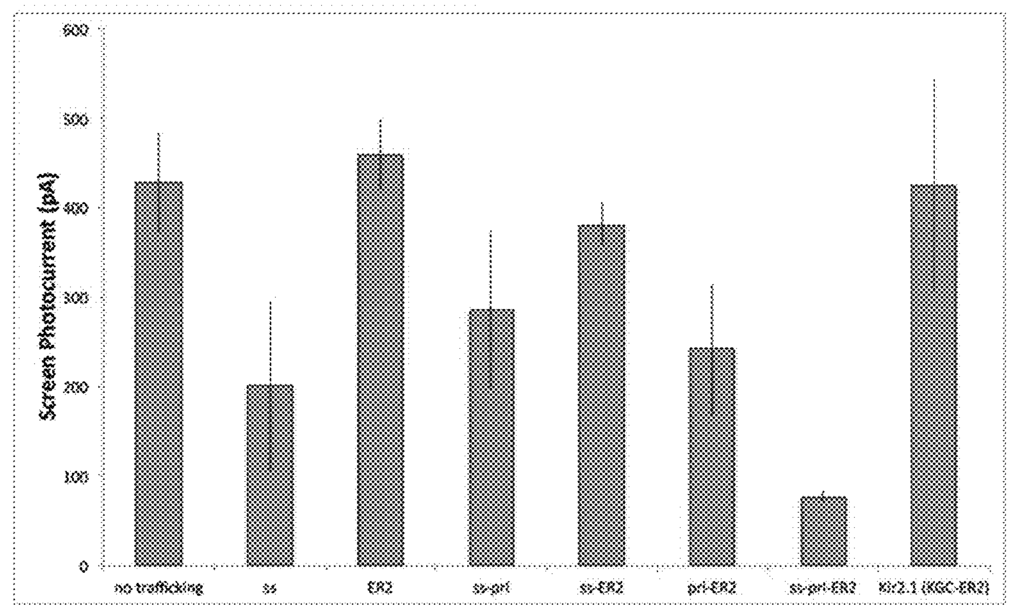
FIG. 7 is a histogram showing the photocurrent effects obtained using signal sequences to boost membrane trafficking of light-activated ion pumps of the invention, as assessed in primary hippocampal mouse neuron culture via whole-cell patch claim.

The results illustrated in FIG. 7 show the photocurrent effects obtained using signal sequences to boost membrane trafficking of light-activated ion pumps of the invention, as assessed in primary hippocampal mouse neuron culture via whole-cell patch claim. Each bar demonstrates the different amounts of photocurrent generated when illuminated with 570/50 nm light.

Example 4

Figure 8:
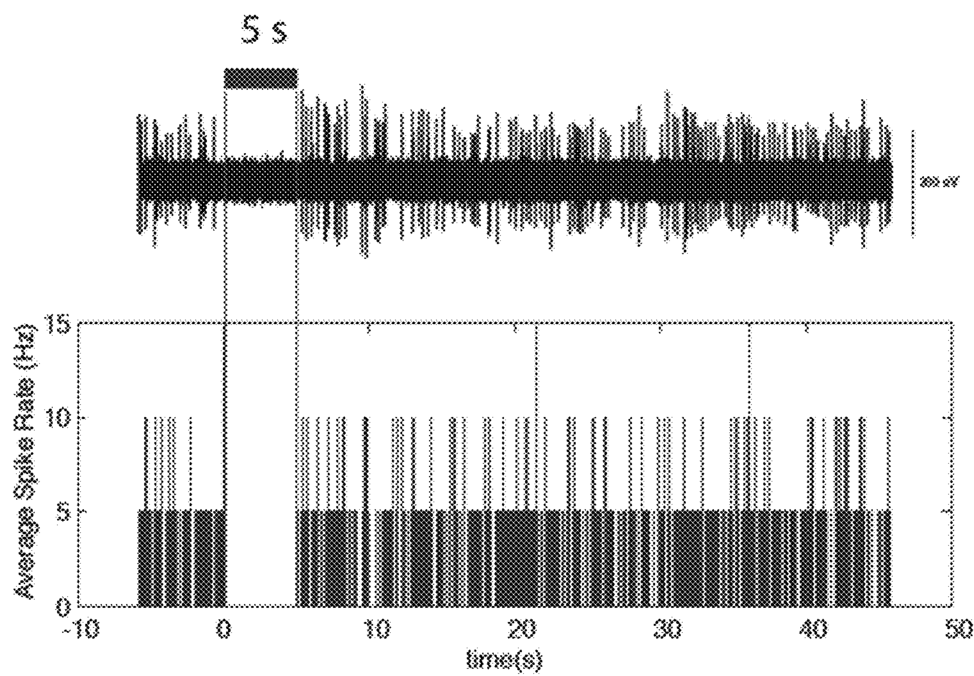
FIG. 8 is an image of traces showing the average spike rate of a cell that includes a heterologous light-activated ion pump of the invention. The figure illustrates results of an in vivo implementation contacting the light-activated ion pump with a light at 655 nm. The top trace is an extracellular recording showing the cell silencing during the five seconds of light contact, and the bottom trace shows the average reduction in spike frequency over a total of seven trials.

Cell silencing was examined using LAIPs. Silencing using red light was tested in an LAIP Halo57 with a double substitution K200R+W214F expressed in a cell. Methods of preparation, expression and measurement were as set forth in Example 1 with average spike rates determined. FIG. 8 shows the average spike rate of a cell that includes a LAIP having the sequence of Halo57 set forth herein as SEQ ID NO:2 with a double substitution K200R+W214F. The amino acid sequence of Halo57 with the K200R+W214F substitution is set forth herein as SEQ ID NO:26. FIG. 8 shows results of an in vivo implementation contacting the light-activated ion pump with a light at 655 nm. The top trace is an extracellular recording showing the cell silencing during the five seconds of light contact, and the bottom trace shows the average reduction in spike frequency over a total of seven trials.

Example 5

Methods

Studies were performed to examine effects of mutagenesis of residues in Halo57 delivered using vectors that also included combinations of signal and export sequences. The efficacy of the combinations were tested using methods described in Example 1. The photocurrents of (1) Halo, (2) Halo57 with the ss-prl-ER2 sequence (see Example 4), (3)

Halo57 having the double substitution K200R+W214F, and with the ss-prl-ER2 sequence; and (4) Halo57 having the double substitution K200R+W214F and with the Kir2.1 sequence were determined. The sequence of ss-prl-ER2 includes nucleic acid sequences set forth herein as SEQ ID NO:15, SEQ ID NO:17, and SEQ ID NO:19, encoding the amino acid sequence set forth herein as SEQ ID NO:16, SEQ ID NO:18, and SEQ ID NO:20. The sequence of Kir2.1 includes nucleic acid sequences set forth herein as SEQ ID NO:21 and SEQ ID NO:19 encoding the amino acid sequence set forth herein as SEQ ID NO:22 and SEQ ID NO:20.

Results

Figure 9:
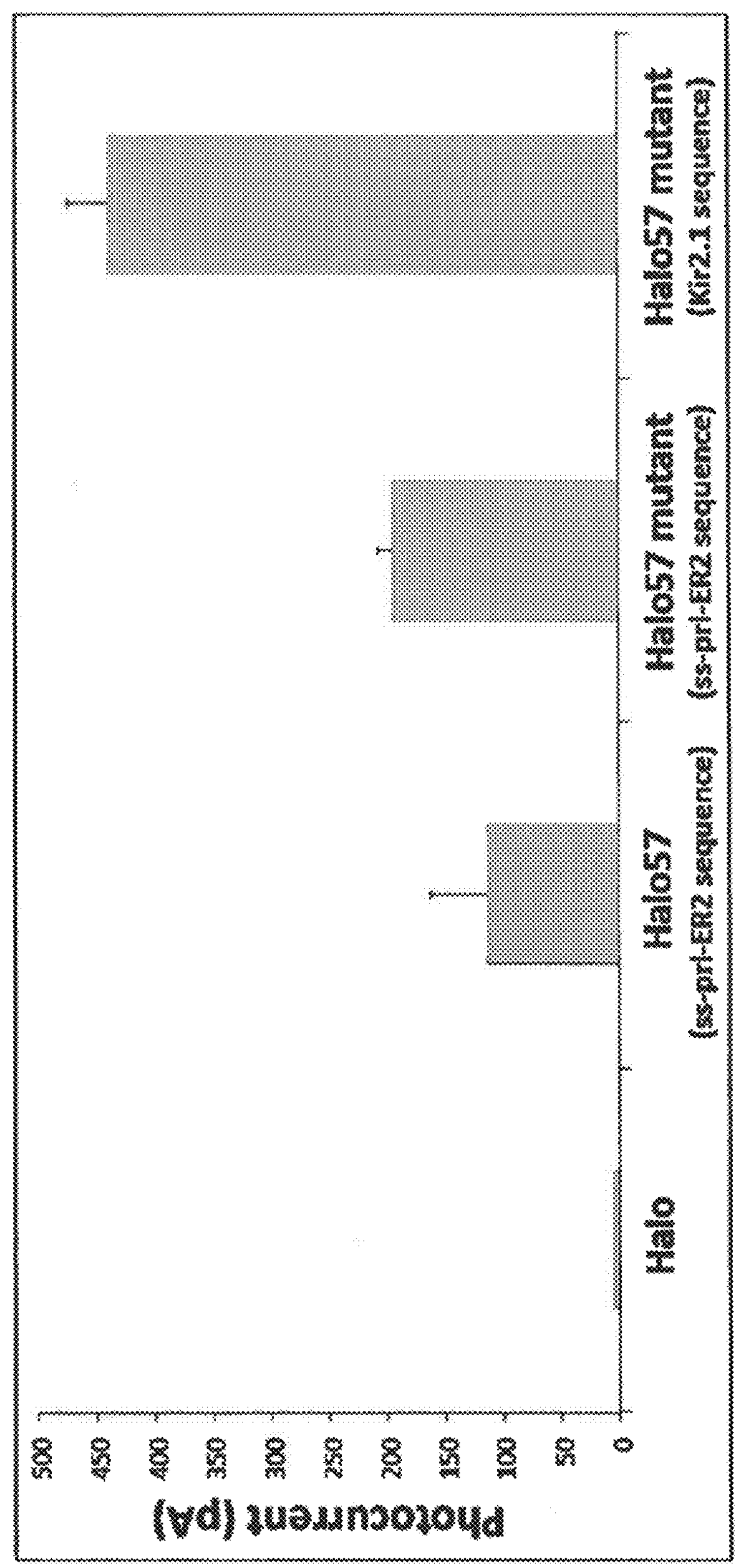
FIG. 9 shows a histogram illustrating effects of mutagenesis of residues in Halo57. The mutation is a double substitution K200R+W214F. The results shown are from combined trafficking and mutation studies. A combination of protein trafficking enhancements with directed mutagenesis resulted in extremely powerful red-light drivable neural silencers. The expressed "ss" sequence includes the amino acid sequence set forth as SEQ ID NO:16. The "ER2" sequence included the amino acid sequence set forth herein as SEQ ID NO: 20. The "ss-prl" sequence included the amino acid sequences of SEQ ID NO:16 and the prolactin signal sequence set forth herein as SEQ ID NO:18. The "ss-ER2" sequence included the amino acid sequence of SEQ ID NO:16 and SEQ ID NO: 20. The "prl-ER2" sequence included the amino acid sequence of SEQ ID NO: 18 and SEQ ID NO:20. The "ss-prl-ER2" sequence included the amino acid sequence of SEQ ID NO:16 and SEQ ID NO: 18; and SEQ ID NO:20. The "Kir2.1" sequence included the amino acid sequence of SEQ ID NO:22 and SEQ ID NO:20.

Results shown in FIG. 9 illustrate effects of mutagenesis of residues in Halo57. The results shown are from combined trafficking and mutation studies. A combination of protein trafficking enhancements with directed mutagenesis resulted in extremely powerful red-light drivable neural silencers as seen for the Halo57 and Halo57 mutants.

Example 6

LAIPs of the invention were prepared and tested using methods set forth in Example 1. Various mutated sequences were prepared, expressed in cells, and tested using methods described in Example 1. In particular, the A122D, K200R and W214F mutations to cruxhalorhodopsins and additionally, the *Natromonas pharaonis* halorhodopsin, were found boost effective light sensitivity and photocurrent amplitude to hyperpolarize excitable cells.

Numerous substitutions and combinations of substitutions were made in *haloarcula* and *halomicrobium*, and other members of the Halobacteriaceae family. Single and multiple substitutions that were made to the sequences, which were then expressed and tested in cells. Substitutions included: K200R, T111S, K200H, K200Q, T203S, [K200Q+W214F], [K200H+W214F], and were made in sequences including Halo57, Gene4, Gene58, Gene 55, Gene55, and Gene54, with the amino acid identification based on alignment of the sequences with Halo57, with amino acids that corresponded to the Halo57 substituted amino acids, substituted in the other, aligned sequences. The mutation position information above is given in reference to Halo57 sequence set forth here as SEQ ID NO:2. Each of the tested mutations was found to boost photocurrent compared to the photocurrent of a non-substituted Halo57 LAIP.

Example 7

Genes described under (a), (b) and (c) were expressed in cells using methods provided below.

Genes

The *Halobacterium salinarum* (strain shark) gene for halorhodopsin referred to herein as Halo57 and having the amino acid sequence set forth herein as SEQ ID NO:2 and a human codon-optimized DNA sequence set forth herein as SEQ ID NO:1;

b) The gene for *Halobacterium salinarum* (strain port) referred to herein as Halo58 and having the amino acid sequence set forth herein as SEQ ID NO:4 and a mammalian codon-optimized DNA sequence set forth herein as SEQ ID NO:3; and c) The gene for *Haloarcula marismortui* cruxhalorhodopsin referred to herein as Gene4 and having the amino acid sequence set forth herein as SEQ ID NO:6 and having a mammalian codon-optimized DNA sequence set forth herein as SEQ ID NO:5 are expressed in cells as follows.

Methods (1) The opsin gene was cloned into a lentiviral or adeno-associated virus (AAV) packaging plasmid, or another desired expression plasmid. In some tests GFP was cloned downstream of the preferred gene, eliminating the stop codon of the opsin gene, thus creating a fusion protein. In some tests no fluorophore was included. In some tests a fusion protein is not utilized and an IRES-GFP.

(2) The viral or expression plasmid was prepared that contained either a strong general promoter, a cell-specific promoter, or a strong general promoter followed by one or more logical elements (such as a lox-stop-lox sequence, which would be removed by Cre recombinase selectively expressed in cells in a transgenic animal, or in a second virus, thus enabling the strong general promoter to then drive the gene).

(3) When a viral plasmid was used, the viral vector was synthesized using the viral plasmid.

(4) If using a virus, as appropriate for gene therapy (over 600 people have been treated with AAV carrying various genetic payloads to date, in 48 separate clinical trials, without a single adverse event), the virus is injected using a small needle or cannula into the area of interest, thus delivering the gene encoding the opsin fusion protein into the cells of interest. If using another expression vector, the vector is directly electroporated or injected into the cell or organism (for acutely expressing the opsin, or making a cell line, or a transgenic mouse or other animal).

(5) Products prepared using sections 1-4 were illuminated with light. Peak illumination wavelength in some experiments was 604 nm when incident intensity was defined in photons/second.

(6) To illuminate two different populations of cells (e.g., in a single tissue) with two different colors of light, one population is first targeted with a *haloarcula* such as the *Halobacterium salinarum* (strain shark)/*Halobacterium halobium* (strain shark) gene for halorhodopsin, and the other population is targeted with a blue-shifted opsin such as Mac (3), using two different viruses (e.g., with different coat proteins or promoters) or two different plasmids (e.g., with two different promoters). Then, after the molecule expresses, the tissue is illuminated with 450±25 nm, 475±25 nm, or 500±25 nm light to preferentially hyperpolarizing the Mac-expressing cells, and the tissue is illuminated with 660±25 nm light to preferentially hyperpolarize the *Halobacterium salinarum* (strain shark)/*Halobacterium halobium* (strain shark) halorhodopsin-expressing cells. The above wavelengths illustrate typical modes of operation, but are not meant to constrain the protocols that can be used. Either narrower or broader wavelengths, or differently-centered illumination spectra, can be used. For prosthetic uses, the devices used to deliver light may be implanted. For drug screening, a xenon lamp or LED can be used to deliver the light.

Discussion

According to principles of this invention, the performance of the above said example compositions of matter may be altered by site-directed mutagenesis, such as the A137D single mutation, the K215R single mutation, and the W229F single mutation to Halo, and the A122D single mutation to the *haloarcula* class, the K200R single mutation to the *haloarcula* class, and the K200R+W214F double mutation to the *haloarcula* class (see FIG. 3). Also, according to principles of this invention, the performance of the above may be altered by appending N-terminal and C-terminal peptide sequences to affect cellular trafficking, such as the N-terminal prolactin endoplasmic sorting sequence (denoted as 'PRL') (amino acid sequence: MDSKGSSQKG-SRLLLLLVVSNLLLCQVVS (SEQ ID NO:18); DNA sequence: gacagcaaaggttcgtcgcagaaagggtcccgcctgctcctgct-gctggtggtgtcaaatctactcttgtgccagggtgtggtctccac ccccgtc; (SEQ ID NO:17), or the MHC class I antigen signal sequence (denoted as "ss") (amino acid sequence: MVPCTLLLLLAAALAPTQTRA (SEQ ID NO:16); DNA sequence: gtcccgtgcacgctgctcctgctgttggcagccgccctggctc-cgactcagacgcgggcc (SEQ ID NO:15), or the C terminal Kir2.1 signal sequence (denoted as "ER2") (amino acid sequence: FCYENEV (SEQ ID NO:20); DNA sequence: ttctgctacgagaatgaagtg (SEQ ID NO:19)), or the C terminal Kir2.1 signal sequence (denoted as "KGC") (amino acid sequence: KSRITSEGEYIPLDQIDINV (SEQ ID NO:22); DNA sequence: aaatccagaattacttctgaaggggagtatatccctctggat-caaatagacatcaatgtt (SEQ ID NO:21)), or combinations thereof, as exemplified by the ss-Prl-Arch (i.e. ss::prl::Arch fusion) molecule (Genbank accession #GU045597), or ss-Prl-Arch-GFP (Genbank accession #GU045599).

In some studies, this invention uses light-activated chloride pumps to hyperpolarize neurons. *Haloarcula*-derived cruxhalorhodopsins are red-light-drivable, which allows hyperpolarization of cells with a color of light heretofore not predominately used in biotechnology for hyperpolarization of cells. By using the *Halobacterium salinarum* (strain shark)/*Halobacterium halobium* (strain shark) gene for halorhodopsin in conjunction with presently existing tools such as Mac, hyperpolarization of two different populations of cells in the same tissue or in the same culture dish becomes possible with substantially less cross-excitation interference seen with less red light driven opsins such as the presently existing Halo. This simultaneous, two-color inactivation, is particularly promising for complex tissues such as the brain. Multi-color perturbation is not limited to only two colors, nor must the perturbation be of the same physiological function.

According to principles of this invention, the performance of the above said molecules or classes of molecules are tuned for optimal use, particularly in context of their use in conjunction with other molecules or optical apparatus. For example, in order to achieve optimal contrast for multiple-color silencing, one may either improve or decrease the performance of one molecule with respect to one another, by the appendage of trafficking enhancing sequences or creation of genetic variants by site-directed mutagenesis, directed evolution, gene shuffling, or altering codon usage.

In some studies, the *haloarcula* genus is used. These have been identified as particularly efficacious light-activated chloride pumps because they express particularly well in mammalian membranes and perform robustly under mammalian physiological conditions.

Example 8

Aspects of the invention include compositions of matter that have been reduced to practice, as described below:

Plasmids encoding for the above genes, have been prepared and used to deliver genes into cells, where the genes have been expressed. As an exemplary vector, lentiviruses carrying payloads encoding for the above genes have been prepared and used to deliver genes into cells resulting in expression of the LAIP in the cells. In addition, adeno-associated viruses carrying payloads encoding for the above genes have been prepared and used to deliver genes into cells, resulting in the expression of the LAIP in the cells. Cells have been prepared that express the LAIP genes set forth in Example 7 and those of FIG. 3. Animals have been prepared that include cells that express the LAIP genes set forth in Example 7, and those of FIG. 3.

It is to be understood that the methods, compositions, and apparatus which have been described above are merely illustrative applications of the principles of the invention. Numerous modifications may be made by those skilled in the art without departing from the scope of the invention.

Although the invention has been described in detail for the purpose of illustration, it is understood that such detail is solely for that purpose and variations can be made by those skilled in the art without departing from the spirit and scope of the invention which is defined by the following claims.

The contents of all literature references, patents, and published patent applications cited throughout this application are incorporated herein by reference in their entirety.

We claim:

1. An isolated polynucleotide comprising a nucleic acid sequence that encodes a light-activated ion pump polypeptide that when expressed in a mammalian excitable cell and contacted with a red light silences the excitable cell, wherein the encoded polypeptide comprises an amino acid sequence set forth herein as SEQ ID NO: 2 with one, two, or more amino acid sequence modifications, wherein the encoded polypeptide has at least 70% amino acid identity to the sequence set forth as SEQ ID NO: 2, and wherein the encoded light-activated ion pump polypeptide includes one of: (i) K→R substitution at the amino acid residue corresponding to amino acid 200 of SEQ ID NO: 2 or (ii) a K→R and a W→F substitution at the amino acid residues corresponding to amino acids 200 and 214, respectively, of SEQ ID NO: 2, and wherein the isolated polynucleotide is not present as part of a human organism.

2. The isolated polynucleotide of claim 1, wherein the amino acid sequence of the encoded light-activated ion pump polypeptide is the sequence set forth as SEQ ID NO: 26.

3. A vertebrate cell comprising a nucleic acid sequence that encodes a light-activated ion pump polypeptide that when expressed in a mammalian excitable cell and contacted with a red light silences the excitable cell and wherein the encoded polypeptide comprises an amino acid sequence set forth here in as SEQ ID NO: 2, with one, two, or more amino acid sequence modifications, and wherein the encoded polypeptide has at least 70% amino acid identity to the sequence set forth as SEQ ID ON: 2, and wherein the encoded polypeptide comprises one or more of:

a) a K→R, K→H, or K→Q substitution at an amino acid residue corresponding to amino acid 200 of the amino acid sequence of Halo57 (SEQ ID NO: 2);

b) a T→S substitution at an amino acid residue corresponding to amino acid 111 of the amino acid sequence of Halo57 (SEQ ID NO: 2);

c) a T→S substitution at an amino acid residue corresponding to amino acid 203 of the amino acid sequence of Halo57 (SEQ ID NO: 2); and d) a K→Q+W→F double substitution at the amino acid residues corresponding to amino acid 200 and 214, respectively, of the amino acid sequence of Halo57 (SEQ ID NO: 2), and wherein the vertebrate cell is not present as part of a human organism.

4. The vertebrate cell of claim 3, wherein the encoded polypeptide has the amino acid sequence of Gene4 (SEQ ID NO: 4), Gene58 (SEQ ID NO: 6), Gene56 (SEQ ID NO: 8), Gene55 (SEQ ID NO: 10), or SEQ ID NO: 2, and comprises one or more of:

a) a K→R, K→H, or K→Q substitution at an amino acid residue corresponding to amino acid 200 of the amino acid sequence of Halo57 (SEQ ID NO: 2);

b) a T→S substitution at an amino acid residue corresponding to amino acid 111 of the amino acid sequence of Halo57 (SEQ ID NO: 2);

c) a T→S substitution at an amino acid residue corresponding to amino acid 203 of the amino acid sequence of Halo57 (SEQ ID NO: 2); and d) a K→Q+W→F double substitution at the amino acid residues corresponding to amino acid 200 and 214, respectively, of the amino acid sequence of Halo57 (SEQ ID NO: 2).

5. A vertebrate cell comprising the isolated polynucleotide of claim 1, wherein the vertebrate cell is not present as part of a human organism.

6. The vertebrate cell of claim 5, wherein the cell is a nervous system cell, a cardiac cell, a circulatory system cell, a visual system cell, an auditory system cell, a hemoglobin-rich cell, or a muscle cell.

7. The vertebrate cell of claim 5, wherein the cell is one or more of: a neuron, an excitable cell, and a mammalian cell.

8. The vertebrate cell of claim 5, wherein the cell further comprises one, two, three, four, or more additional polynucleotides encoding light-activated ion pumps, wherein at least one of the additional encoded light-activated ion pumps is activated by contact with light having a non-red light wavelength.

9. The isolated polynucleotide of claim 1, wherein the encoded light-activated ion pump polypeptide has at least 80% amino acid identity to the sequence set forth as SEQ ID NO: 2.

10. The isolated polynucleotide of claim 1, wherein the encoded light-activated ion pump polypeptide has at least 90% amino acid identity to the sequence set forth as SEQ ID NO: 2.

11. The isolated polynucleotide of claim 1, wherein the encoded light-activated ion pump polypeptide has at least 95% amino acid identity to the sequence set forth as SEQ ID NO: 2.

12. A vector comprising the isolated polynucleotide sequence of claim 1.

13. The vector of claim 12, further comprising a polynucleotide encoding a cell trafficking signal polypeptide.

14. A method of hyperpolarizing a cell, the method comprising, a) delivering to a cell, a polynucleotide encoding a light-activated ion pump polypeptide that when expressed in an excitable cell and contacted with a red light silences the excitable cell, wherein the encoded polypeptide of the light-activated ion pump polypeptide comprises an amino acid sequence set forth as SEQ ID NO: 2 with one, two, or more amino acid sequence modifications, and wherein the encoded polypeptide has at least 70% amino acid identity to the sequence set forth as SEQ ID NO: 2;

b) expressing the encoded light-activated ion pump polypeptide in the cell; and c) contacting the expressed light-activated ion pump polypeptide with a light that activates the light-activated ion pump polypeptide and hyperpolarizes the cell.

15. A method of treating a disorder in a subject, the method comprising:

a) administering to a subject in need of such treatment, a therapeutically effective amount of a polynucleotide encoding a light-activated ion pump polypeptide that when expressed in an excitable cell and contacted with a red light silences the excitable cell, wherein the encoded polypeptide comprises an amino acid sequence set forth as SEQ ID NO: 2 with one, two, or more amino acid sequence modifications, and wherein the encoded polypeptide has at least 70% amino acid identity to the sequence set forth as SEQ ID NO: 2;

b) expressing the encoded light-activated ion pump polypeptide in an excitable cell in the subject; and c) contacting the encoded light-activated ion pump polypeptide with a light that activates the encoded light-activated ion pump polypeptide and hyperpolarizes the cell, to treat the disorder.

16. A method of identifying an effect of a candidate compound on a vertebrate cell, the method comprising, a) delivering to a test cell, a polynucleotide encoding a light-activated ion pump polypeptide that when expressed in an excitable cell and contacted with a red light silences the excitable cell, wherein the encoded polypeptide comprises an amino acid sequence set forth as SEQ ID NO: 2 with one, two, or more amino acid sequence modifications, and wherein the encoded polypeptide has at least 70% amino acid identity to the sequence set forth as SEQ ID NO: 2;

b) expressing the encoded light-activated ion pump polypeptide in the test cell;

c) contacting the test cell with a light under conditions suitable to activate the expressed light-activated ion pump and hyperpolarize the test cell;

d) contacting the test cell with a candidate compound; and e) identifying the presence or absence of a change in the hyperpolarization or in a hyperpolarization-mediated cell characteristic in the test cell contacted with the light and the candidate compound compared to the hyperpolarization or the hyperpolarization-mediated cell characteristic, respectively, in a control cell contacted with the light and not contacted with the candidate compound, wherein a change in the hyperpolarization or the hyperpolarization-mediated cell characteristic in the test cell compared to the control cell identifies an effect of the candidate compound on the test cell.

17. The isolated polynucleotide of claim 1, wherein the encoded light-activated ion pump polypeptide has at least 98% amino acid identity to the sequence set forth as SEQ ID NO: 2.

18. The vertebrate cell of claim 3, wherein the encoded polypeptide has at least 85% amino acid identity to the sequence set forth as SEQ ID NO: 2.

19. The vertebrate cell of claim 3, wherein the encoded polypeptide has at least 95% amino acid identity to the sequence set forth as SEQ ID NO: 2.

20. The method of claim 14, wherein the encoded polypeptide has at least 85% amino acid identity to the sequence set forth as SEQ ID NO: 2.

21. The method of claim 14, wherein the encoded polypeptide has at least 95% amino acid identity to the sequence set forth as SEQ ID NO: 2.

22. The method of claim 15, wherein the encoded polypeptide has at least 85% amino acid identity to the sequence set forth as SEQ ID NO: 2.

23. The method of claim 15, wherein the encoded polypeptide has at least 95% amino acid identity to the sequence set forth as SEQ ID NO: 2.

24. The method of claim 16, wherein the encoded polypeptide has at least 85% amino acid identity to the sequence set forth as SEQ ID NO: 2.

25. The method of claim 16, wherein the encoded polypeptide has at least 95% amino acid identity to the sequence set forth as SEQ ID NO: 2.

* * * * *

SEQUENCE LISTING

```
<160> NUMBER OF SEQ ID NOS: 27

<210> SEQ ID NO 1
<211> LENGTH: 828
<212> TYPE: DNA
<213> ORGANISM: Artificial Sequence
<220> FEATURE:
<223> OTHER INFORMATION: Mammalian-codon optimized sequence

<400> SEQUENCE: 1

atgaccgccg tgagcaccac agccactacc gtgctgcagg ccacacagag cgacgtgctg     60

caggagatcc agtccaactt cctgctgaat agctccatct gggtgaacat tgctctggcc    120

ggagtggtca tcctgctgtt tgtggccatg gggagggatc tggaatcccc tagagctaag    180

ctgatctggg tggccacaat gctggtgcca ctggtgtcta tttctagtta cgctggactg    240

gccagtgggc tgactgtggg cttcctgcag atgccacctg gacacgctct ggccggacag    300

gaggtgctga gcccatgggg ccggtatctg acatggactt tctccactcc catgatcctg    360

ctggctctgg gactgctggc cgacaccgat attgccagcc tgttcaccgc catcacaatg    420
```

```
gacattggca tgtgcgtgac aggactggcc gctgccctga tcactagctc ccatctgctg    480

cgctgggtgt tctacggaat ttcttgtgct ttctttgtgg ccgtgctgta tgtgctgctg    540

gtgcagtggc cagctgatgc tgaggctgct gggaccagtg aaatctttgg cactctgaag    600

attctgaccg tggtgctgtg gctggggtac cctatcctgt gggctctggg ctctgaggga    660

gtggccctgc tgagtgtggg agtgaccagc tggggatact ccggactgga catcctggct    720

aaatacgtgt tcgccttttct gctgctgaga tgggtggctg ccaatgaagg cacagtgtct    780

gggagtggaa tgggaatcgg gtccggagga gctgctccag ccgacgat                 828
```

<210> SEQ ID NO 2
<211> LENGTH: 276
<212> TYPE: PRT
<213> ORGANISM: Halobacterium salinarum

<400> SEQUENCE: 2

```
Met Thr Ala Val Ser Thr Thr Ala Thr Thr Val Leu Gln Ala Thr Gln
1               5                   10                  15

Ser Asp Val Leu Gln Glu Ile Gln Ser Asn Phe Leu Leu Asn Ser Ser
            20                  25                  30

Ile Trp Val Asn Ile Ala Leu Ala Gly Val Val Ile Leu Leu Phe Val
        35                  40                  45

Ala Met Gly Arg Asp Leu Glu Ser Pro Arg Ala Lys Leu Ile Trp Val
    50                  55                  60

Ala Thr Met Leu Val Pro Leu Val Ser Ile Ser Ser Tyr Ala Gly Leu
65                  70                  75                  80

Ala Ser Gly Leu Thr Val Gly Phe Leu Gln Met Pro Pro Gly His Ala
                85                  90                  95

Leu Ala Gly Gln Glu Val Leu Ser Pro Trp Gly Arg Tyr Leu Thr Trp
            100                 105                 110

Thr Phe Ser Thr Pro Met Ile Leu Leu Ala Leu Gly Leu Leu Ala Asp
        115                 120                 125

Thr Asp Ile Ala Ser Leu Phe Thr Ala Ile Thr Met Asp Ile Gly Met
    130                 135                 140

Cys Val Thr Gly Leu Ala Ala Ala Leu Ile Thr Ser Ser His Leu Leu
145                 150                 155                 160

Arg Trp Val Phe Tyr Gly Ile Ser Cys Ala Phe Phe Val Ala Val Leu
                165                 170                 175

Tyr Val Leu Leu Val Gln Trp Pro Ala Asp Ala Glu Ala Ala Gly Thr
            180                 185                 190

Ser Glu Ile Phe Gly Thr Leu Lys Ile Leu Thr Val Val Leu Trp Leu
        195                 200                 205

Gly Tyr Pro Ile Leu Trp Ala Leu Gly Ser Glu Gly Val Ala Leu Leu
    210                 215                 220

Ser Val Gly Val Thr Ser Trp Gly Tyr Ser Gly Leu Asp Ile Leu Ala
225                 230                 235                 240

Lys Tyr Val Phe Ala Phe Leu Leu Leu Arg Trp Val Ala Ala Asn Glu
                245                 250                 255

Gly Thr Val Ser Gly Ser Gly Met Gly Ile Gly Ser Gly Gly Ala Ala
            260                 265                 270

Pro Ala Asp Asp
        275
```

<210> SEQ ID NO 3
<211> LENGTH: 828

```
<212> TYPE: DNA
<213> ORGANISM: Artificial Sequence
<220> FEATURE:
<223> OTHER INFORMATION: Mammalian-codon optimized sequence

<400> SEQUENCE: 3

atgacagccg ccagcaccac cgccaccacc gtgctgcagg ccacacagtc cgacgtgctg     60

caggagatcc agagcaactt cctgctgaac tccagcatct gggtgaacat tgccctggcc    120

ggcgtggtga tcctgctgtt tgtggccatg ggccgcgacc tggaaagccc ccgcgccaag    180

ctgatttggg tggccacaat gctggtgccc ctggtgtcca tcagcagcta tgccggactg    240

gccagcggac tgaccgtggg atttctgcag atgccccccg gccacgccct ggccggccag    300

gaggtgctgt ccccctgggg ccggtacctg acatggacat tctccacccc tatgatcctg    360

ctggccctgg gactgctggc cgatacagac atcgcctctc tgttcaccgc catcaccatg    420

gacatcggga tgtgcgtgac cggactggcc gccgccctga tcaccagctc ccacctgctg    480

cgctgggtgt tctacggcat ctcttgcgcc tttttcgtgg ccgtgctgta cgtgctgctg    540

gtgcagtggc ccgccgacgc cgaggccgcc ggcaccagcg agatcttcgg cacactgaag    600

attctgacag tggtgctgtg gctgggatac ccaatcctgt gggccctggg ctctgagggc    660

gtggccctgc tgagcgtggg agtgacctct tggggctaca gcggactgga cattctggcc    720

aagtacgtgt tcgccttcct gctgctgagg tgggtggccg ccaatgaagg aacagtgtct    780

gggtccggca tgggcatcgg ctccgggggc gccacacctg ccgacgac                 828


<210> SEQ ID NO 4
<211> LENGTH: 276
<212> TYPE: PRT
<213> ORGANISM: Haloarcula marismortui

<400> SEQUENCE: 4

Met Thr Ala Ala Ser Thr Thr Ala Thr Thr Val Leu Gln Ala Thr Gln
1               5                   10                  15

Ser Asp Val Leu Gln Glu Ile Gln Ser Asn Phe Leu Leu Asn Ser Ser
            20                  25                  30

Ile Trp Val Asn Ile Ala Leu Ala Gly Val Val Ile Leu Leu Phe Val
        35                  40                  45

Ala Met Gly Arg Asp Leu Glu Ser Pro Arg Ala Lys Leu Ile Trp Val
    50                  55                  60

Ala Thr Met Leu Val Pro Leu Val Ser Ile Ser Ser Tyr Ala Gly Leu
65                  70                  75                  80

Ala Ser Gly Leu Thr Val Gly Phe Leu Gln Met Pro Pro Gly His Ala
                85                  90                  95

Leu Ala Gly Gln Glu Val Leu Ser Pro Trp Gly Arg Tyr Leu Thr Trp
            100                 105                 110

Thr Phe Ser Thr Pro Met Ile Leu Leu Ala Leu Gly Leu Leu Ala Asp
        115                 120                 125

Thr Asp Ile Ala Ser Leu Phe Thr Ala Ile Thr Met Asp Ile Gly Met
    130                 135                 140

Cys Val Thr Gly Leu Ala Ala Ala Leu Ile Thr Ser Ser His Leu Leu
145                 150                 155                 160

Arg Trp Val Phe Tyr Gly Ile Ser Cys Ala Phe Phe Val Ala Val Leu
                165                 170                 175

Tyr Val Leu Leu Val Gln Trp Pro Ala Asp Ala Glu Ala Ala Gly Thr
            180                 185                 190
```

```
Ser Glu Ile Phe Gly Thr Leu Lys Ile Leu Thr Val Val Leu Trp Leu
        195                 200                 205

Gly Tyr Pro Ile Leu Trp Ala Leu Gly Ser Glu Gly Val Ala Leu Leu
    210                 215                 220

Ser Val Gly Val Thr Ser Trp Gly Tyr Ser Gly Leu Asp Ile Leu Ala
225                 230                 235                 240

Lys Tyr Val Phe Ala Phe Leu Leu Leu Arg Trp Val Ala Ala Asn Glu
                245                 250                 255

Gly Thr Val Ser Gly Ser Gly Met Gly Ile Gly Ser Gly Gly Ala Thr
            260                 265                 270

Pro Ala Asp Asp
        275


<210> SEQ ID NO 5
<211> LENGTH: 828
<212> TYPE: DNA
<213> ORGANISM: Artificial Sequence
<220> FEATURE:
<223> OTHER INFORMATION: Mammalian-codon optimized sequence

<400> SEQUENCE: 5

atgaccgccg cttccaccac agctactacc atgctgcagg ccacacagtc tgacgtgctg      60

caggagatcc agagtaactt cctgctgaat agctccatct gggtgaacat tgctctggcc     120

ggggtggtca tcctgctgtt tgtggccatg ggcagggata tcgaatctcc tagagctaag     180

ctgatttggg tggccacaat gctggtgcca ctggtgagca tctctagtta cgctgggctg     240

gcctccggac tgactgtggg attcctgcag atgccacctg gacacgctct ggccggacag     300

gaggtgctgt ctccatgggg ccggtatctg acatggactt tcagtactcc catgatcctg     360

ctggctctgg gactgctggc cgacaccgat attgccagcc tgttcaccgc catcacaatg     420

gacattggaa tgtgcgtgac agggctggcc gctgccctga tcactagctc ccatctgctg     480

cgctgggtgt tctacggaat ttcttgtgct ttctttgtgg ccgtgctgta tgtgctgctg     540

gtgcagtggc cagctgatgc tgaggctgct ggcaccagcg aaatctttgg aactctgaag     600

attctgaccg tggtgctgtg gctggggtac cctatcctgt gggctctggg aagcgaggga     660

gtggccctgc tgtccgtggg agtgacatct tggggctaca gtggactgga cattctggct     720

aaatacgtgt tcgccttttct gctgctgaga tgggtggctg ccaatgaagg agccgtgtct     780

gggagtggaa tgagcatcgg gtccggagga gctgctccag ccgacgat                  828


<210> SEQ ID NO 6
<211> LENGTH: 276
<212> TYPE: PRT
<213> ORGANISM: Halobacterium salinarum

<400> SEQUENCE: 6

Met Thr Ala Ala Ser Thr Thr Ala Thr Thr Met Leu Gln Ala Thr Gln
1               5                   10                  15

Ser Asp Val Leu Gln Glu Ile Gln Ser Asn Phe Leu Leu Asn Ser Ser
            20                  25                  30

Ile Trp Val Asn Ile Ala Leu Ala Gly Val Val Ile Leu Leu Phe Val
        35                  40                  45

Ala Met Gly Arg Asp Ile Glu Ser Pro Arg Ala Lys Leu Ile Trp Val
    50                  55                  60

Ala Thr Met Leu Val Pro Leu Val Ser Ile Ser Ser Tyr Ala Gly Leu
65                  70                  75                  80
```

```
Ala Ser Gly Leu Thr Val Gly Phe Leu Gln Met Pro Pro Gly His Ala
                85                  90                  95

Leu Ala Gly Gln Glu Val Leu Ser Pro Trp Gly Arg Tyr Leu Thr Trp
            100                 105                 110

Thr Phe Ser Thr Pro Met Ile Leu Leu Ala Leu Gly Leu Leu Ala Asp
        115                 120                 125

Thr Asp Ile Ala Ser Leu Phe Thr Ala Ile Thr Met Asp Ile Gly Met
    130                 135                 140

Cys Val Thr Gly Leu Ala Ala Ala Leu Ile Thr Ser Ser His Leu Leu
145                 150                 155                 160

Arg Trp Val Phe Tyr Gly Ile Ser Cys Ala Phe Phe Val Ala Val Leu
                165                 170                 175

Tyr Val Leu Leu Val Gln Trp Pro Ala Asp Ala Glu Ala Ala Gly Thr
            180                 185                 190

Ser Glu Ile Phe Gly Thr Leu Lys Ile Leu Thr Val Val Leu Trp Leu
        195                 200                 205

Gly Tyr Pro Ile Leu Trp Ala Leu Gly Ser Glu Gly Val Ala Leu Leu
    210                 215                 220

Ser Val Gly Val Thr Ser Trp Gly Tyr Ser Gly Leu Asp Ile Leu Ala
225                 230                 235                 240

Lys Tyr Val Phe Ala Phe Leu Leu Leu Arg Trp Val Ala Ala Asn Glu
                245                 250                 255

Gly Ala Val Ser Gly Ser Gly Met Ser Ile Gly Ser Gly Gly Ala Ala
            260                 265                 270

Pro Ala Asp Asp
        275

<210> SEQ ID NO 7
<211> LENGTH: 774
<212> TYPE: DNA
<213> ORGANISM: Artificial Sequence
<220> FEATURE:
<223> OTHER INFORMATION: Mammalian-codon optimized sequence

<400> SEQUENCE: 7

atgctgcagg agatccagtc taacttcctg ctgaatagct ccatctgggt gaacattgct     60

ctggccggag tggtcatcct gctgtttgtg gccatgggga gggacctgga aagtcctaga    120

gctaagctga tctgggtggc caccatgctg gtgccactgg tgagcatttc tagttacgct    180

ggactggcct ccggactgac agtgggcttc ctgcagatgc cacctggaca cgctctggcc    240

ggacaggagg tgctgtctcc atggggccgg tatctgacct ggacattcag tacacccatg    300

atcctgctgg ctctgggact gctggccgac actgatattg cttctctgtt tactgccatc    360

accatggaca ttggcatgtg cgtgactgga ctggccgctg ccctgatcac cagctcccat    420

ctgctgcgct gggtgttcta cggaattagc tgtgctttct ttgtggccgt gctgtatgtg    480

ctgctggtgc agtggccagc tgatgctgag gctgctggga cttccgaaat ctttggcacc    540

ctgaagattc tgacagtggt gctgtggctg gggtacccta tcctgtgggc tctgggctct    600

gagggagtgg ccctgctgag tgtgggcgtg acaagctggg ggtactccgg cctggatatc    660

ctggctaaat acgtgttcgc ctttctgctg ctgagatggg tggccacaaa tgaaggcacc    720

gtgagcggga gtggaatggg aatcgggtcc ggaggagctg ctccagccga cgat          774

<210> SEQ ID NO 8
<211> LENGTH: 258
<212> TYPE: PRT
```

<213> ORGANISM: Haloarcula sinaiiensis

<400> SEQUENCE: 8

```
Met Leu Gln Glu Ile Gln Ser Asn Phe Leu Leu Asn Ser Ser Ile Trp
1               5                   10                  15

Val Asn Ile Ala Leu Ala Gly Val Val Ile Leu Leu Phe Val Ala Met
            20                  25                  30

Gly Arg Asp Leu Glu Ser Pro Arg Ala Lys Leu Ile Trp Val Ala Thr
        35                  40                  45

Met Leu Val Pro Leu Val Ser Ile Ser Ser Tyr Ala Gly Leu Ala Ser
    50                  55                  60

Gly Leu Thr Val Gly Phe Leu Gln Met Pro Pro Gly His Ala Leu Ala
65                  70                  75                  80

Gly Gln Glu Val Leu Ser Pro Trp Gly Arg Tyr Leu Thr Trp Thr Phe
                85                  90                  95

Ser Thr Pro Met Ile Leu Leu Ala Leu Gly Leu Leu Ala Asp Thr Asp
            100                 105                 110

Ile Ala Ser Leu Phe Thr Ala Ile Thr Met Asp Ile Gly Met Cys Val
        115                 120                 125

Thr Gly Leu Ala Ala Ala Leu Ile Thr Ser Ser His Leu Leu Arg Trp
    130                 135                 140

Val Phe Tyr Gly Ile Ser Cys Ala Phe Phe Val Ala Val Leu Tyr Val
145                 150                 155                 160

Leu Leu Val Gln Trp Pro Ala Asp Ala Glu Ala Ala Gly Thr Ser Glu
                165                 170                 175

Ile Phe Gly Thr Leu Lys Ile Leu Thr Val Val Leu Trp Leu Gly Tyr
            180                 185                 190

Pro Ile Leu Trp Ala Leu Gly Ser Glu Gly Val Ala Leu Leu Ser Val
        195                 200                 205

Gly Val Thr Ser Trp Gly Tyr Ser Gly Leu Asp Ile Leu Ala Lys Tyr
    210                 215                 220

Val Phe Ala Phe Leu Leu Leu Arg Trp Val Ala Thr Asn Glu Gly Thr
225                 230                 235                 240

Val Ser Gly Ser Gly Met Gly Ile Gly Ser Gly Gly Ala Ala Pro Ala
                245                 250                 255

Asp Asp
```

<210> SEQ ID NO 9
<211> LENGTH: 726
<212> TYPE: DNA
<213> ORGANISM: Artificial Sequence
<220> FEATURE:
<223> OTHER INFORMATION: Mammalian-codon optimized sequence

<400> SEQUENCE: 9

```
atgaacatcg ctctggccgg agtggtcatc ctgctgttcg tggctatggg aagggacctg      60

gagtccccta gagctaagct gatctgggtg gccaccatgc tggtgccact ggtgtctatt     120

agctcctacg ctggactggc cagtgggctg acagtgggct ttctgcagat gccacctgga     180

cacgctctgg ccggacagga agtgctgagc ccatggggcc ggtatctgac ctggacattc     240

tccacaccca tgatcctgct ggctctggga ctgctggccg acactgatat tgcttctctg     300

tttactgcca tcaccatgga cattggcatg tgcgtgactg gactggccgc tgccctgatc     360

acctctagtc atctgctgcg ctgggtgttc tacggaattt cttgtgcttt ctttgtggcc     420

gtgctgtatg tgctgctggt gcagtggcca gctgatgctg aggctgctgg gactagtgaa     480
```

```
atctttggca ccctgaagat tctgacagtg gtgctgtggc tggggtaccc tatcctgtgg    540

gctctgggca gcgagggagt ggccctgctg tccgtgggag tgacatcttg gggtacagt    600

ggcctggata ttctggctaa atacgtgttc gcctttctgc tgctgagatg ggtggccaca    660

aatgaaggca ctgtgagcgg gtccggaatg ggaatcggga gcggaggagc tgccccagcc    720

gacgat                                                              726


<210> SEQ ID NO 10
<211> LENGTH: 242
<212> TYPE: PRT
<213> ORGANISM: Haloarcula californiae

<400> SEQUENCE: 10

Met Asn Ile Ala Leu Ala Gly Val Val Ile Leu Leu Phe Val Ala Met
1               5                   10                  15

Gly Arg Asp Leu Glu Ser Pro Arg Ala Lys Leu Ile Trp Val Ala Thr
            20                  25                  30

Met Leu Val Pro Leu Val Ser Ile Ser Ser Tyr Ala Gly Leu Ala Ser
        35                  40                  45

Gly Leu Thr Val Gly Phe Leu Gln Met Pro Pro Gly His Ala Leu Ala
    50                  55                  60

Gly Gln Glu Val Leu Ser Pro Trp Gly Arg Tyr Leu Thr Trp Thr Phe
65                  70                  75                  80

Ser Thr Pro Met Ile Leu Leu Ala Leu Gly Leu Leu Ala Asp Thr Asp
                85                  90                  95

Ile Ala Ser Leu Phe Thr Ala Ile Thr Met Asp Ile Gly Met Cys Val
            100                 105                 110

Thr Gly Leu Ala Ala Ala Leu Ile Thr Ser Ser His Leu Leu Arg Trp
        115                 120                 125

Val Phe Tyr Gly Ile Ser Cys Ala Phe Phe Val Ala Val Leu Tyr Val
    130                 135                 140

Leu Leu Val Gln Trp Pro Ala Asp Ala Glu Ala Ala Gly Thr Ser Glu
145                 150                 155                 160

Ile Phe Gly Thr Leu Lys Ile Leu Thr Val Val Leu Trp Leu Gly Tyr
                165                 170                 175

Pro Ile Leu Trp Ala Leu Gly Ser Glu Gly Val Ala Leu Leu Ser Val
            180                 185                 190

Gly Val Thr Ser Trp Gly Tyr Ser Gly Leu Asp Ile Leu Ala Lys Tyr
        195                 200                 205

Val Phe Ala Phe Leu Leu Leu Arg Trp Val Ala Thr Asn Glu Gly Thr
    210                 215                 220

Val Ser Gly Ser Gly Met Gly Ile Gly Ser Gly Gly Ala Ala Pro Ala
225                 230                 235                 240

Asp Asp


<210> SEQ ID NO 11
<211> LENGTH: 819
<212> TYPE: DNA
<213> ORGANISM: Artificial Sequence
<220> FEATURE:
<223> OTHER INFORMATION: Mammalian-codon optimized sequence

<400> SEQUENCE: 11

atgtccgcca ccacaactct gctgcaggct actcagtctg aggctgtgac cgccatcgaa     60

aacgacgtgc tgctgagctc ctctctgtgg gctaatgtgg ctctggccgg cctggctatc    120
```

```
ctgctgttcg tgtatatggg aaggaacgtg gaggctccaa gagccaagct gatttgggga    180

gccaccctga tgatcccccct ggtgagtatt agtagctatc tgggactgct gagcggactg    240

acagtgggct tcatcgaaat gcctgctgga cacgctctgg ccggagagga agtgatgagt    300

cagtggggca ggtacctgac ttgggccctg tccaccccaa tgatcctgct ggctctggga    360

ctgctggccg acgtggatat tggggacctg ttcgtggtca tcgccgctga tattggaatg    420

tgcgtgacag ggctggccgc tgccctgatc acttcctctt acggcctgcg gtgggccttt    480

tatctggtgt cttgtgcttt ctttctggtg gtgctgtacg ctatcctggt ggagtggcca    540

cagagcgcca ccgctgctgg gacagacgaa attttcggca cactgcgcgc cctgactgtg    600

gtgctgtggc tgggatatcc tatcatttgg gctgtgggaa tcgagggact ggctctggtg    660

cagtccgtgg gcctgaccag ttggggatac agcgccctgg atattggggc caaatatctg    720

ttcgcttttc tgctgctgcg gtgggtggct gccaatcagg acgtggtggg gcagccctcc    780

ctggataccc attctgaagg cacagctcct gccgacgat                           819
```

```
<210> SEQ ID NO 12
<211> LENGTH: 273
<212> TYPE: PRT
<213> ORGANISM: Halomicrobium mukohataei

<400> SEQUENCE: 12

Met Ser Ala Thr Thr Thr Leu Leu Gln Ala Thr Gln Ser Glu Ala Val
1               5                   10                  15

Thr Ala Ile Glu Asn Asp Val Leu Leu Ser Ser Ser Leu Trp Ala Asn
            20                  25                  30

Val Ala Leu Ala Gly Leu Ala Ile Leu Leu Phe Val Tyr Met Gly Arg
        35                  40                  45

Asn Val Glu Ala Pro Arg Ala Lys Leu Ile Trp Gly Ala Thr Leu Met
    50                  55                  60

Ile Pro Leu Val Ser Ile Ser Ser Tyr Leu Gly Leu Leu Ser Gly Leu
65                  70                  75                  80

Thr Val Gly Phe Ile Glu Met Pro Ala Gly His Ala Leu Ala Gly Glu
                85                  90                  95

Glu Val Met Ser Gln Trp Gly Arg Tyr Leu Thr Trp Ala Leu Ser Thr
            100                 105                 110

Pro Met Ile Leu Leu Ala Leu Gly Leu Leu Ala Asp Val Asp Ile Gly
        115                 120                 125

Asp Leu Phe Val Val Ile Ala Ala Asp Ile Gly Met Cys Val Thr Gly
    130                 135                 140

Leu Ala Ala Ala Leu Ile Thr Ser Ser Tyr Gly Leu Arg Trp Ala Phe
145                 150                 155                 160

Tyr Leu Val Ser Cys Ala Phe Phe Leu Val Val Leu Tyr Ala Ile Leu
                165                 170                 175

Val Glu Trp Pro Gln Ser Ala Thr Ala Ala Gly Thr Asp Glu Ile Phe
            180                 185                 190

Gly Thr Leu Arg Ala Leu Thr Val Val Leu Trp Leu Gly Tyr Pro Ile
        195                 200                 205

Ile Trp Ala Val Gly Ile Glu Gly Leu Ala Leu Val Gln Ser Val Gly
    210                 215                 220

Leu Thr Ser Trp Gly Tyr Ser Ala Leu Asp Ile Gly Ala Lys Tyr Leu
225                 230                 235                 240

Phe Ala Phe Leu Leu Leu Arg Trp Val Ala Ala Asn Gln Asp Val Val
```

```
                245                 250                 255

Gly Gln Pro Ser Leu Asp Thr His Ser Glu Gly Thr Ala Pro Ala Asp
            260                 265                 270

Asp
```

<210> SEQ ID NO 13
<211> LENGTH: 873
<212> TYPE: DNA
<213> ORGANISM: Artificial Sequence
<220> FEATURE:
<223> OTHER INFORMATION: Mammalian-codon optimized sequence

<400> SEQUENCE: 13

```
atgactgaga ccctcccacc cgtgactgaa agcgccgtcg ctctgcaagc agaggttacc     60

cagcgggagc tgttcgagtt cgtcctcaac gaccccctcc tggcttctag cctctacatc    120

aacattgctc tggcaggcct gtctatactg ctgttcgtct tcatgaccag gggactcgat    180

gaccctaggg ctaaactgat tgcagtgagc acaattctgg ttcccgtggt ctctatcgct    240

tcctacactg ggctggcatc tggtctcaca atcagtgtcc tggaaatgcc agctggccac    300

tttgccgaag ggagttctgt catgctggga ggcgaagagg tcgatggggt tgtcacaatg    360

tggggtcgct acctcacctg ggctctcagt acccccatga tcctgctggc actcggactc    420

ctggccggaa gtaacgccac caaactcttc actgctatta cattcgatat cgccatgtgc    480

gtgaccgggc tcgcagctgc cctcaccacc agcagccatc tgatgagatg gttttggtat    540

gccatctctt gtgcctgctt tctggtggtg ctgtatatcc tgctggtgga gtgggctcag    600

gatgccaagg ctgcagggac agccgacatg tttaatacac tgaagctgct cactgtggtg    660

atgtggctgg gttaccctat cgtttgggca ctcggcgtgg agggaatcgc agttctgcct    720

gttggtgtga caagctgggg ctactccttc ctggacattg tggccaagta tatttttgcc    780

tttctgctgc tgaattatct gacttccaat gagtccgtgg tgtccggctc catactggac    840

gtgccatccg ccagcggcac acctgccgat gac                                 873
```

<210> SEQ ID NO 14
<211> LENGTH: 291
<212> TYPE: PRT
<213> ORGANISM: Natromonas pharaois

<400> SEQUENCE: 14

```
Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125
```

```
Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp
    290


<210> SEQ ID NO 15
<211> LENGTH: 60
<212> TYPE: DNA
<213> ORGANISM: Mus musculus

<400> SEQUENCE: 15

gtcccgtgca cgctgctcct gctgttggca gccgccctgg ctccgactca gacgcgggcc     60


<210> SEQ ID NO 16
<211> LENGTH: 21
<212> TYPE: PRT
<213> ORGANISM: Mus musculus

<400> SEQUENCE: 16

Met Val Pro Cys Thr Leu Leu Leu Leu Leu Ala Ala Ala Leu Ala Pro
1               5                   10                  15

Thr Gln Thr Arg Ala
            20


<210> SEQ ID NO 17
<211> LENGTH: 96
<212> TYPE: DNA
<213> ORGANISM: Mus musculus

<400> SEQUENCE: 17

gacagcaaag gttcgtcgca gaaagggtcc cgcctgctcc tgctgctggt ggtgtcaaat     60

ctactcttgt gccagggtgt ggtctccacc cccgtc                               96


<210> SEQ ID NO 18
<211> LENGTH: 29
<212> TYPE: PRT
<213> ORGANISM: Mus musculus

<400> SEQUENCE: 18

Met Asp Ser Lys Gly Ser Ser Gln Lys Gly Ser Arg Leu Leu Leu Leu
1               5                   10                  15
```

```
Leu Val Val Ser Asn Leu Leu Leu Cys Gln Val Val Ser
            20                  25


<210> SEQ ID NO 19
<211> LENGTH: 21
<212> TYPE: DNA
<213> ORGANISM: Mus musculus

<400> SEQUENCE: 19

ttctgctacg agaatgaagt g                                             21


<210> SEQ ID NO 20
<211> LENGTH: 7
<212> TYPE: PRT
<213> ORGANISM: Mus musculus

<400> SEQUENCE: 20

Phe Cys Tyr Glu Asn Glu Val
1               5


<210> SEQ ID NO 21
<211> LENGTH: 60
<212> TYPE: DNA
<213> ORGANISM: Mus musculus

<400> SEQUENCE: 21

aaatccagaa ttacttctga aggggagtat atccctctgg atcaaataga catcaatgtt     60


<210> SEQ ID NO 22
<211> LENGTH: 20
<212> TYPE: PRT
<213> ORGANISM: Mus musculus

<400> SEQUENCE: 22

Lys Ser Arg Ile Thr Ser Glu Gly Glu Tyr Ile Pro Leu Asp Gln Ile
1               5                   10                  15

Asp Ile Asn Val
            20


<210> SEQ ID NO 23
<211> LENGTH: 1605
<212> TYPE: DNA
<213> ORGANISM: Artificial Sequence
<220> FEATURE:
<223> OTHER INFORMATION: Synthetic Halo-GFP fusion sequence

<400> SEQUENCE: 23

atgactgaga ccctcccacc cgtgactgaa agcgccgtcg ctctgcaagc agaggttacc     60

cagcgggagc tgttcgagtt cgtcctcaac gaccccctcc tggcttctag cctctacatc    120

aacattgctc tggcaggcct gtctatactg ctgttcgtct tcatgaccag gggactcgat    180

gaccctaggg ctaaactgat tgcagtgagc acaattctgg ttcccgtggt ctctatcgct    240

tcctacactg ggctggcatc tggtctcaca atcagtgtcc tggaaatgcc agctggccac    300

tttgccgaag ggagttctgt catgctggga ggcgaagagg tcgatggggt tgtcacaatg    360

tggggtcgct acctcacctg ggctctcagt acccccatga tcctgctggc actcggactc    420

ctggccggaa gtaacgccac caaactcttc actgctatta cattcgatat cgccatgtgc    480

gtgaccgggc tcgcagctgc cctcaccacc agcagccatc tgatgagatg gttttggtat    540

gccatctctt gtgcctgctt tctggtggtg ctgtatatcc tgctggtgga gtgggctcag    600
```

```
gatgccaagg ctgcagggac agccgacatg tttaatacac tgaagctgct cactgtggtg     660

atgtggctgg gttaccctat cgtttgggca ctcggcgtgg agggaatcgc agttctgcct     720

gttggtgtga caagctgggg ctactccttc ctggacattg tggccaagta tatttttgcc     780

tttctgctgc tgaattatct gacttccaat gagtccgtgg tgtccggctc catactggac     840

gtgccatccg ccagcggcac acctgccgat gaccgaccgg tagtagcagt gagcaagggc     900

gaggagctgt tcaccggggt ggtgcccatc ctggtcgagc tggacggcga cgtaaacggc     960

cacaagttca gcgtgtccgg cgagggcgag ggcgatgcca cctacggcaa gctgaccctg    1020

aagttcatct gcaccaccgg caagctgccc gtgccctggc ccaccctcgt gaccaccctg    1080

acctacggcg tgcagtgctt cagccgctac cccgaccaca tgaagcagca cgacttcttc    1140

aagtccgcca tgcccgaagg ctacgtccag gagcgcacca tcttcttcaa ggacgacggc    1200

aactacaaga cccgcgccga ggtgaagttc gagggcgaca ccctggtgaa ccgcatcgag    1260

ctgaagggca tcgacttcaa ggaggacggc aacatcctgg ggcacaagct ggagtacaac    1320

tacaacagcc acaacgtcta tatcatggcc gacaagcaga agaacggcat caaggtgaac    1380

ttcaagatcc gccacaacat cgaggacggc agcgtgcagc tcgccgacca ctaccagcag    1440

aacaccccca tcggcgacgg ccccgtgctg ctgcccgaca accactacct gagcacccag    1500

tccgccctga gcaaagaccc caacgagaag cgcgatcaca tggtcctgct ggagttcgtg    1560

accgccgccg ggatcactct cggcatggac gagctgtaca agtaa                    1605
```

```
<210> SEQ ID NO 24
<211> LENGTH: 533
<212> TYPE: PRT
<213> ORGANISM: Artificial Sequence
<220> FEATURE:
<223> OTHER INFORMATION: Synthetic Halo-GFP sequence

<400> SEQUENCE: 24

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Tyr Ala Ile Ser Cys Ala Cys Phe Leu Val Val Leu Tyr Ile
            180                 185                 190
```

```
Leu Leu Val Glu Trp Ala Gln Asp Ala Lys Ala Ala Gly Thr Ala Asp
        195                 200                 205

Met Phe Asn Thr Leu Lys Leu Leu Thr Val Val Met Trp Leu Gly Tyr
    210                 215                 220

Pro Ile Val Trp Ala Leu Gly Val Glu Gly Ile Ala Val Leu Pro Val
225                 230                 235                 240

Gly Val Thr Ser Trp Gly Tyr Ser Phe Leu Asp Ile Val Ala Lys Tyr
                245                 250                 255

Ile Phe Ala Phe Leu Leu Leu Asn Tyr Leu Thr Ser Asn Glu Ser Val
            260                 265                 270

Val Ser Gly Ser Ile Leu Asp Val Pro Ser Ala Ser Gly Thr Pro Ala
        275                 280                 285

Asp Asp Arg Pro Val Val Ala Val Ser Lys Gly Glu Glu Leu Phe Thr
    290                 295                 300

Gly Val Val Pro Ile Leu Val Glu Leu Asp Gly Asp Val Asn Gly His
305                 310                 315                 320

Lys Phe Ser Val Ser Gly Glu Gly Glu Gly Asp Ala Thr Tyr Gly Lys
                325                 330                 335

Leu Thr Leu Lys Phe Ile Cys Thr Thr Gly Lys Leu Pro Val Pro Trp
            340                 345                 350

Pro Thr Leu Val Thr Thr Leu Thr Tyr Gly Val Gln Cys Phe Ser Arg
        355                 360                 365

Tyr Pro Asp His Met Lys Gln His Asp Phe Phe Lys Ser Ala Met Pro
    370                 375                 380

Glu Gly Tyr Val Gln Glu Arg Thr Ile Phe Phe Lys Asp Asp Gly Asn
385                 390                 395                 400

Tyr Lys Thr Arg Ala Glu Val Lys Phe Glu Gly Asp Thr Leu Val Asn
                405                 410                 415

Arg Ile Glu Leu Lys Gly Ile Asp Phe Lys Glu Asp Gly Asn Ile Leu
            420                 425                 430

Gly His Lys Leu Glu Tyr Asn Tyr Asn Ser His Asn Val Tyr Ile Met
        435                 440                 445

Ala Asp Lys Gln Lys Asn Gly Ile Lys Val Asn Phe Lys Ile Arg His
    450                 455                 460

Asn Ile Glu Asp Gly Ser Val Gln Leu Ala Asp His Tyr Gln Gln Asn
465                 470                 475                 480

Thr Pro Ile Gly Asp Gly Pro Val Leu Leu Pro Asp Asn His Tyr Leu
                485                 490                 495

Ser Thr Gln Ser Ala Leu Ser Lys Asp Pro Asn Glu Lys Arg Asp His
            500                 505                 510

Met Val Leu Leu Glu Phe Val Thr Ala Ala Gly Ile Thr Leu Gly Met
        515                 520                 525

Asp Glu Leu Tyr Lys
    530


<210> SEQ ID NO 25
<211> LENGTH: 534
<212> TYPE: PRT
<213> ORGANISM: Artificial Sequence
<220> FEATURE:
<223> OTHER INFORMATION: Synthetic Halo-GFP sequence

<400> SEQUENCE: 25

Met Thr Glu Thr Leu Pro Pro Val Thr Glu Ser Ala Val Ala Leu Gln
1               5                   10                  15
```

```
Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
    50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
    130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
    210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp Arg Pro Val Val Ala Val Ser Lys Gly Glu Glu Leu Phe
    290                 295                 300

Thr Gly Val Val Pro Ile Leu Val Glu Leu Asp Gly Asp Val Asn Gly
305                 310                 315                 320

His Lys Phe Ser Val Ser Gly Glu Gly Glu Gly Asp Ala Thr Tyr Gly
                325                 330                 335

Lys Leu Thr Leu Lys Phe Ile Cys Thr Thr Gly Lys Leu Pro Val Pro
            340                 345                 350

Trp Pro Thr Leu Val Thr Thr Leu Thr Tyr Gly Val Gln Cys Phe Ser
        355                 360                 365

Arg Tyr Pro Asp His Met Lys Gln His Asp Phe Phe Lys Ser Ala Met
    370                 375                 380

Pro Glu Gly Tyr Val Gln Glu Arg Thr Ile Phe Phe Lys Asp Asp Gly
385                 390                 395                 400

Asn Tyr Lys Thr Arg Ala Glu Val Lys Phe Glu Gly Asp Thr Leu Val
                405                 410                 415

Asn Arg Ile Glu Leu Lys Gly Ile Asp Phe Lys Glu Asp Gly Asn Ile
            420                 425                 430
```

```
Leu Gly His Lys Leu Glu Tyr Asn Tyr Asn Ser His Asn Val Tyr Ile
        435                 440                 445

Met Ala Asp Lys Gln Lys Asn Gly Ile Lys Val Asn Phe Lys Ile Arg
    450                 455                 460

His Asn Ile Glu Asp Gly Ser Val Gln Leu Ala Asp His Tyr Gln Gln
465                 470                 475                 480

Asn Thr Pro Ile Gly Asp Gly Pro Val Leu Leu Pro Asp Asn His Tyr
                485                 490                 495

Leu Ser Thr Gln Ser Ala Leu Ser Lys Asp Pro Asn Glu Lys Arg Asp
            500                 505                 510

His Met Val Leu Leu Glu Phe Val Thr Ala Ala Gly Ile Thr Leu Gly
        515                 520                 525

Met Asp Glu Leu Tyr Lys
    530


<210> SEQ ID NO 26
<211> LENGTH: 276
<212> TYPE: PRT
<213> ORGANISM: Artificial Sequence
<220> FEATURE:
<223> OTHER INFORMATION: Sequence of Halo57 with K200R + W214F double
      substitution

<400> SEQUENCE: 26

Met Thr Ala Val Ser Thr Thr Ala Thr Thr Val Leu Gln Ala Thr Gln
1               5                   10                  15

Ser Asp Val Leu Gln Glu Ile Gln Ser Asn Phe Leu Leu Asn Ser Ser
            20                  25                  30

Ile Trp Val Asn Ile Ala Leu Ala Gly Val Val Ile Leu Leu Phe Val
        35                  40                  45

Ala Met Gly Arg Asp Leu Glu Ser Pro Arg Ala Lys Leu Ile Trp Val
    50                  55                  60

Ala Thr Met Leu Val Pro Leu Val Ser Ile Ser Ser Tyr Ala Gly Leu
65                  70                  75                  80

Ala Ser Gly Leu Thr Val Gly Phe Leu Gln Met Pro Pro Gly His Ala
                85                  90                  95

Leu Ala Gly Gln Glu Val Leu Ser Pro Trp Gly Arg Tyr Leu Thr Trp
            100                 105                 110

Thr Phe Ser Thr Pro Met Ile Leu Leu Ala Leu Gly Leu Leu Ala Asp
        115                 120                 125

Thr Asp Ile Ala Ser Leu Phe Thr Ala Ile Thr Met Asp Ile Gly Met
    130                 135                 140

Cys Val Thr Gly Leu Ala Ala Ala Leu Ile Thr Ser Ser His Leu Leu
145                 150                 155                 160

Arg Trp Val Phe Tyr Gly Ile Ser Cys Ala Phe Phe Val Ala Val Leu
                165                 170                 175

Tyr Val Leu Leu Val Gln Trp Pro Ala Asp Ala Glu Ala Ala Gly Thr
            180                 185                 190

Ser Glu Ile Phe Gly Thr Leu Arg Ile Leu Thr Val Val Leu Trp Leu
        195                 200                 205

Gly Tyr Pro Ile Leu Phe Ala Leu Gly Ser Glu Gly Val Ala Leu Leu
    210                 215                 220

Ser Val Gly Val Thr Ser Trp Gly Tyr Ser Gly Leu Asp Ile Leu Ala
225                 230                 235                 240

Lys Tyr Val Phe Ala Phe Leu Leu Leu Arg Trp Val Ala Ala Asn Glu
                245                 250                 255
```

```
Gly Thr Val Ser Gly Ser Gly Met Gly Ile Gly Ser Gly Gly Ala Ala
            260                 265                 270

Pro Ala Asp Asp
        275


<210> SEQ ID NO 27
<211> LENGTH: 32
<212> TYPE: PRT
<213> ORGANISM: Mus musculus

<400> SEQUENCE: 27

Asp Ser Lys Gly Ser Ser Gln Lys Gly Ser Arg Leu Leu Leu Leu Leu
1               5                   10                  15

Val Val Ser Asn Leu Leu Leu Cys Gln Gly Val Val Ser Thr Pro Val
            20                  25                  30
```